(12) United States Patent
Hurley

(10) Patent No.: US 9,320,722 B2
(45) Date of Patent: Apr. 26, 2016

(54) REGULATORS OF ALDEHYDE DEHYDROGENASE ALDH3A1 AND RELATED THERAPEUTIC METHODS

(71) Applicant: Indiana University Research and Technology Corporation, Indianapolis, IN (US)

(72) Inventor: Thomas D. Hurley, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/498,618

(22) Filed: Sep. 26, 2014

(65) Prior Publication Data
US 2015/0202169 A1    Jul. 23, 2015

Related U.S. Application Data

(60) Provisional application No. 61/883,393, filed on Sep. 27, 2013.

(51) Int. Cl.
| | | |
|---|---|---|
| *A61K 38/00* | (2006.01) |
| *A61P 35/00* | (2006.01) |
| *A61K 31/145* | (2006.01) |
| *A61K 45/06* | (2006.01) |
| *A61K 31/167* | (2006.01) |
| *A61K 31/63* | (2006.01) |
| *A61K 31/635* | (2006.01) |
| *A61K 31/4184* | (2006.01) |
| *A61K 31/136* | (2006.01) |
| *A61K 31/381* | (2006.01) |
| *A61K 31/426* | (2006.01) |
| *A61K 31/4436* | (2006.01) |
| *A61K 31/4439* | (2006.01) |
| *A61K 31/4468* | (2006.01) |
| *A61K 31/5377* | (2006.01) |
| *A61K 31/5386* | (2006.01) |
| *A61K 31/553* | (2006.01) |

(52) U.S. Cl.
CPC ............. *A61K 31/145* (2013.01); *A61K 31/136* (2013.01); *A61K 31/167* (2013.01); *A61K 31/381* (2013.01); *A61K 31/4184* (2013.01); *A61K 31/426* (2013.01); *A61K 31/4436* (2013.01); *A61K 31/4439* (2013.01); *A61K 31/4468* (2013.01); *A61K 31/5377* (2013.01); *A61K 31/5386* (2013.01); *A61K 31/553* (2013.01); *A61K 31/63* (2013.01); *A61K 31/635* (2013.01); *A61K 45/06* (2013.01)

(58) Field of Classification Search
None
See application file for complete search history.

(56) References Cited

U.S. PATENT DOCUMENTS 2,466,010 A  *  4/1949  Dickey .................... C09B 51/00
549/495

* cited by examiner

*Primary Examiner* — Patrick Lewis
(74) *Attorney, Agent, or Firm* — Quarles & Brady, LLP

(57) ABSTRACT

Described herein are compositions and methods for the treatment of cancer, and in particular cancers characterized by a high level of ALD3H1 activity, which is associated with chemoresistance to cancer chemotherapeutic agents that are degraded by ALD3H1. The compositions described herein act as competitive inhibitors of ALD3H1 and thereby reduce breakdown of chemotherapeutics by this enzyme, and increase their efficacy for cancer treatment.

16 Claims, 25 Drawing Sheets

N-(4-((4-(methylsulfonyl)-2-nitrophenyl)amino)phenyl)acetamide

Daidzin

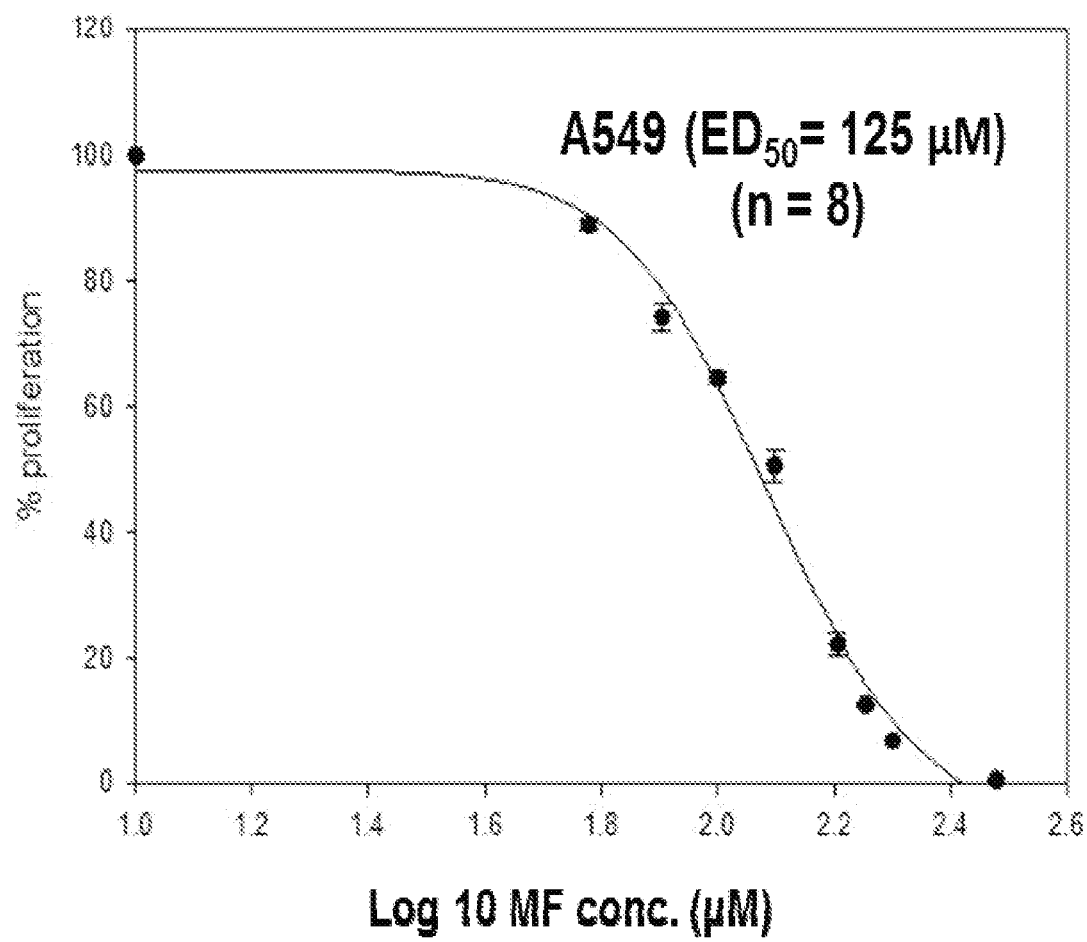

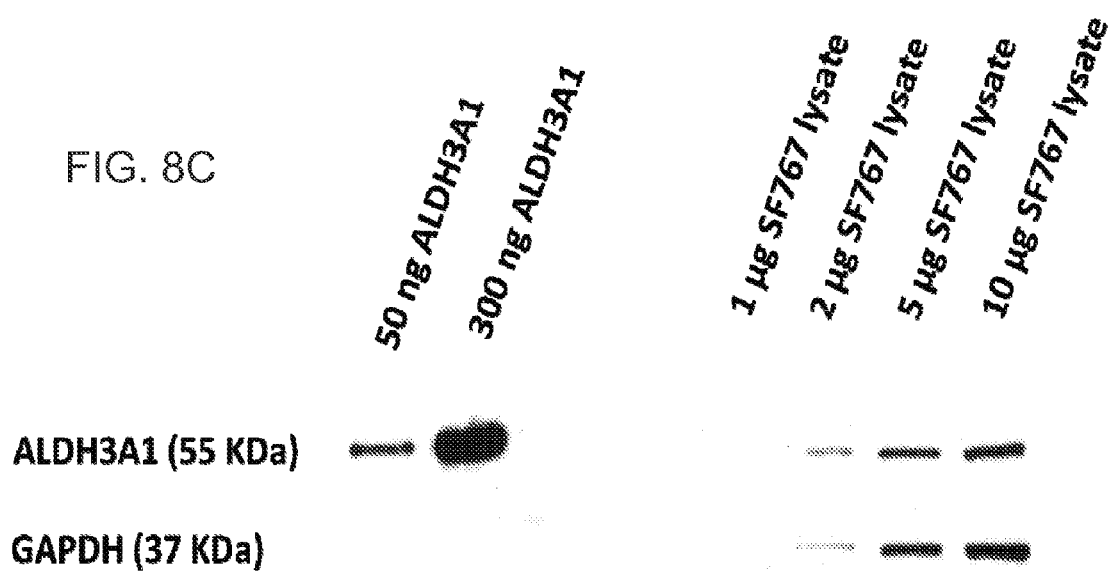

1-((4-fluorophenyl)sulfonyl)-2-methyl-1*H*-benzo[*d*]imidazole

REGULATORS OF ALDEHYDE DEHYDROGENASE ALDH3A1 AND RELATED THERAPEUTIC METHODS

CROSS-REFERENCE TO RELATED APPLICATIONS

This application claims the benefit of U.S. provisional Application No. 61/883,393 filed on Sep. 27, 2013, which is incorporated by reference herein in its entirety.

STATEMENT REGARDING FEDERALLY SPONSORED RESEARCH

This invention was made with government support under AA018123 awarded by the National Institutes of Health. The government has certain rights in the invention.

BACKGROUND OF THE INVENTION

A major challenge for the effective treatment of cancer and related conditions is resistance to chemotherapeutic agents ("chemoresistance"). A major mechanism for resistance to certain chemotherapeutics, e.g., Paclitaxel, is degradation via the aldehyde dehydrogenase 3A1 (ALDH3A1), which is often specifically overexpressed in cancer cells relative to non-cancerous tissues. Thus, there is an ongoing need to find reagents and methods for treating cancer that selectively reduce ALDH3A1 activity, which will thereby enhance the efficacy of ALDH3A1-sensitive chemotherapeutics by limiting their breakdown in cancer cells.

SUMMARY OF THE INVENTION

Described herein are compositions and methods for the treatment of cancer, and in particular cancers characterized by a high level of ALD3H1 activity, which is associated with chemoresistance to cancer chemotherapeutic agents that are degraded by ALD3H1. The compositions described herein act as competitive inhibitors of ALD3H1 and thereby reduce breakdown of chemotherapeutics by this enzyme, and increase their efficacy for cancer treatment.

Accordingly, in a first aspect, described herein is a pharmaceutical composition for cancer treatment comprising a pharmaceutically acceptable excipient and a therapeutically effective amount of a compound having the structure of Formula (I):

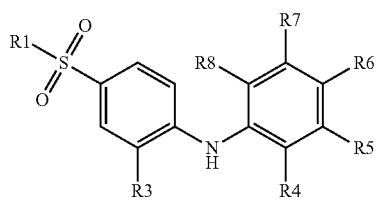

wherein:
R1 is selected from the R1 groups listed for the following compounds of Table 1A: CB29, Compound 2, Compound 5, Compound 9, and Compound 10;
R3 is —NO$_2$; —F, —Cl, —OH, or —O-Me;
R4 is —H;
R5 is selected from the R5 groups listed for the following compounds of Table 1A: CB29, Compound 8, and Compound 9;
R6 is selected from the R6 groups listed for the following compounds of Table 1A: CB29, Compound 5, Compound 8, Compound 10, and Compound 11;
R7 is —H; and
R8 is —H.

In some embodiments, the compound in the pharmaceutical composition has the structure of Formula (Ia) (Compound CB29):

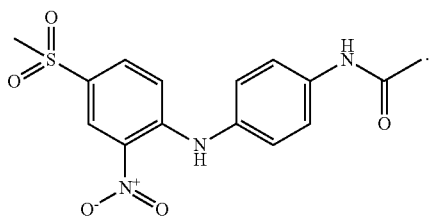 [SMILES: CC(=O)Nc1ccc(Nc2ccc(S(C)(=O)=O)cc2[N+](=O)[O-])cc1]

In some embodiments the pharmaceutical composition comprising the compound having the structure of Formula (I) further comprises one or more chemotherapeutic agents that are substrates for ALDH3A1. In some embodiments the one or more chemotherapeutic agents comprise paclitaxel, doxorubicin, or 4-hydroxycyclophosphamide.

In a second aspect, described herein is a method for treating cancer comprising administering to a subject in need thereof a pharmaceutical composition comprising a therapeutically effective amount of a compound having the structure of Formula (I):

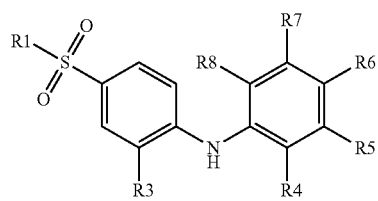

wherein:
R1 is selected from the R1 groups listed for the following compounds of Table 1A: CB29, Compound 2, Compound 5, Compound 9, and Compound 10;
R3 is —NO$_2$; —F, —Cl, —OH, or —O-Me;
R4 is —H;
R5 is selected from the R5 groups listed for the following compounds of Table 1A: CB29, Compound 8, and Compound 9;
R6 is selected from the R5 groups listed for the following compounds of Table 1A: CB29, Compound 5, Compound 8, Compound 10, and Compound 11;
R7 is —H; and
R8 is —H; and wherein the subject is treated with one or more chemotherapeutic agents that are substrates for ALDH3A1.

In some embodiments, the compound used in the method of treatment has the structure of Formula (Ia) Compound CB29:

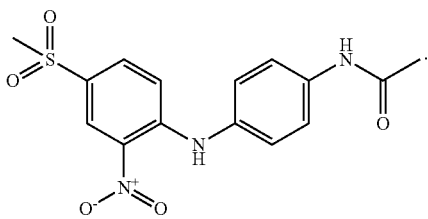 [SMILES: CC(=O)Nc1ccc(Nc2ccc(S(C)(=O)=O)cc2[N+](=O)[O-])cc1]

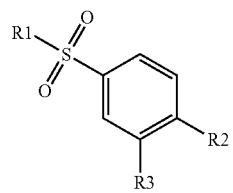

wherein:
- R1 is selected from the R1 groups listed for the following compounds of Table 1B: CB29 and Compound 18;
- R2 is selected from the R2 groups listed for the following compounds of Table 1B: CB29, Compound 17, and Compound 19; and
- R3 is —NO$_2$ and wherein the subject is treated with one or more chemotherapeutic agents that are substrates for ALDH3A1.

In some embodiments, the one or more chemotherapeutic agents used to treat the subject comprise paclitaxel, doxorubicin, 4-hydroxycyclophosphamide, or a combination thereof. In some embodiments, the one or more chemotherapeutic agents are administered to the subject before the administration of the pharmaceutical composition. In other embodiments, the one or more chemotherapeutic agents are administered to the subject after the administration of the pharmaceutical composition. In further embodiments, the one or more chemotherapeutic agents are co-administered with the pharmaceutical composition comprising the compound having the structure of Formula (I).

In some embodiments, the pharmaceutical composition to be used in the method of treatment comprises, in combination, the therapeutically effective amount of the compound having the structure of Formula (I), and the one or more chemotherapeutic agents.

In some embodiments, the subject to be treated is suffering from a cancer characterized by overexpression of ALDH3A1. In some embodiments the subject the subject to be treated is suffering from hepatoma, lung adenocarcinoma, myeloma, breast cancer, colon cancer, or glioblastoma.

In some embodiments the method also includes the step of obtaining, from the subject to be treated, a biological sample comprising cancer cells and determining an ALDH3A1 mRNA, protein expression, or enzymatic activity level before, during, or after treatment with the pharmaceutical composition.

In a third aspect provided herein is a pharmaceutical composition for cancer treatment comprising a pharmaceutically acceptable excipient and a therapeutically effective amount of a compound having the structure of Formula (II):

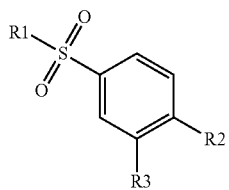

wherein:
- R1 is selected from the R1 groups listed for the following compounds of Table 1B: CB29 and Compound 18;
- R2 is selected from the R2 groups listed for the following compounds of Table 1B: CB29, Compound 17, and Compound 19; and
- R3 is —NO$_2$.

In a fourth aspect, provided herein is a method for treating cancer comprising administering to a subject in need thereof a pharmaceutical composition comprising a therapeutically effective amount of a compound having the structure of Formula (II):

In some embodiments, the one or more chemotherapeutic agents are administered to the subject before the administration of the pharmaceutical composition. In other embodiments, the one or more chemotherapeutic agents are administered to the subject after the administration of the pharmaceutical composition. In further embodiments, the one or more chemotherapeutic agents are co-administered with the pharmaceutical composition comprising the compound having the structure of Formula (II).

In some embodiments, the subject to be treated is suffering from a cancer characterized by overexpression of ALDH3A1. In some embodiments, the subject the subject to be treated is suffering from hepatoma, lung adenocarcinoma, myeloma, breast cancer, colon cancer, or glioblastoma.

In some embodiments, the method also includes the step of obtaining, from the subject to be treated, a biological sample comprising cancer cells and determining an ALDH3A1 mRNA, protein expression, or enzymatic activity level before, during, or after treatment with the pharmaceutical composition.

In a fifth aspect, described herein is a pharmaceutical composition for cancer treatment comprising a pharmaceutically acceptable excipient and a therapeutically effective amount of a compound having the structure of Formula (III):

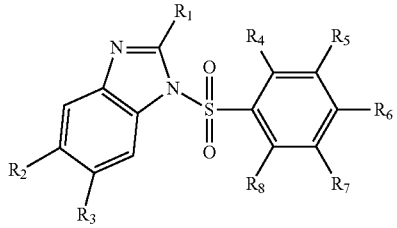

wherein:
- R1 is selected from the R1 groups listed for the following compounds of Table 6: CB7, Compound A10; Compound B36, and Compound B37;
- R2 is —H;
- R3 is —H;
- R4 is —H;
- R5 is selected from the R5 groups listed for the following compounds of Table 6: CB7, Compound A53, and Compound A64;

R6 is selected from the R6 groups listed for the following compounds of Table 6: CB7, Compound A21, Compound A10, and Compound A62;
R7 is —H; and
R8 is —H.

In some embodiments the pharmaceutical composition further comprises one or more chemotherapeutic agents that are substrates for ALDH3A1. In some embodiments the one or more chemotherapeutic agents comprise paclitaxel, doxorubicin, 4-hydroxycyclophosphamide, or a combination thereof.

In a sixth aspect provided herein is a method for treating cancer comprising administering to a subject in need thereof a pharmaceutical composition comprising a therapeutically effective amount of a compound having the structure of Formula (III):

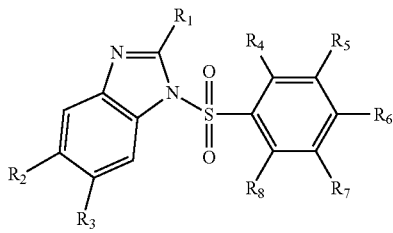

wherein:
R1 is selected from the R1 groups listed for the following compounds of Table 6: CB7, Compound A10; Compound B36, and Compound B37;
R2 is —H;
R3 is —H;
R4 is —H;
R5 is selected from the R5 groups listed for the following compounds of Table 6: CB7, Compound A53, and Compound A64;
R6 is selected from the R6 groups listed for the following compounds of Table 6: CB7, Compound A21, Compound A10, and Compound A62;
R7 is —H; and
R8 is —H; and wherein the subject is treated with one or more chemotherapeutic agents that are substrates for ALDH3A1.

In some embodiments, the one or more chemotherapeutic agents are administered to the subject before the administration of the pharmaceutical composition. In other embodiments, the one or more chemotherapeutic agents are administered to the subject after the administration of the pharmaceutical composition. In further embodiments, the one or more chemotherapeutic agents are co-administered with the pharmaceutical composition comprising the compound having the structure of Formula (III).

In some embodiments, the subject to be treated is suffering from a cancer characterized by overexpression of ALDH3A1. In some embodiments, the subject to be treated is suffering from hepatoma, lung adenocarcinoma, myeloma, breast cancer, colon cancer, or glioblastoma.

In some embodiments the method also includes the step of obtaining, from the subject to be treated, a biological sample comprising cancer cells and determining an ALDH3A1 mRNA, protein expression, or enzymatic activity level before, during, or after treatment with the pharmaceutical composition.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

FIG. 7A. Calculation of ED50 for A549, SF767 and CCD13Lu cell lines A549 (ALDH1A1 and ALDH3A1 expressing).

FIG. 8C. Quantitation of ALDH3A1 expression in SF767 cell line. Serial dilutions of SF767 cell lysates (1 µg-10 µg) were compared against serial dilutions of recombinantly purified ALDH3A1 (50 ng-300 ng). Purified recombinant His-tagged ALDH3A1 protein served as positive control and GAPDH served as a loading control.

DETAILED DESCRIPTION OF THE INVENTION

Figure 1A:
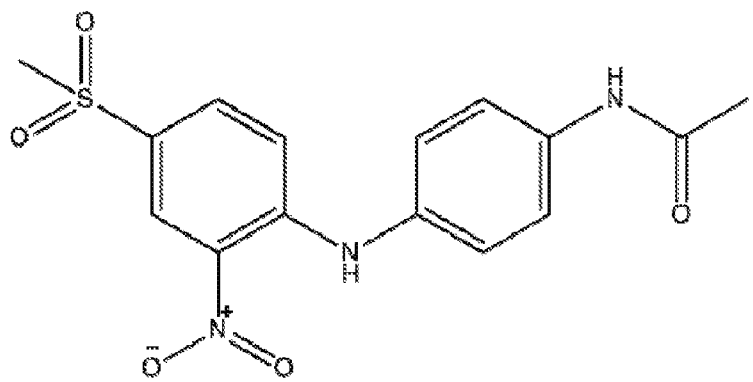
FIG. 1A. CB29 and its mode of inhibition. The structure of CB29; N-[4-{(4-(methylsulfonyl)-2-nitrophenyl) 4amino} phenyl]acetamide.

Described herein are compositions and methods for the treatment of cancer based on the discovery of specific inhibitors of ALD3H1, an enzyme responsible for chemoresistance to a number of commonly used cancer chemotherapeutic agents.

Definitions:

Bioavailability" refers to the percentage of the weight of compounds disclosed herein, such as, compounds of any of Formula (I), Formula (Ia), Formula (II), or Formula (III), dosed that is delivered into the general circulation of the animal or human being studied. The total exposure ($AUC_{(0-\infty)}$) of a drug when administered intravenously is usually defined as 100% bioavailable (F %).

"Oral bioavailability" refers to the extent to which compounds disclosed herein, such as, compounds of any of Formula (I), Formula (Ia), Formula (II), or Formula (III), are absorbed into the general circulation when the pharmaceutical composition is taken orally as compared to intravenous injection.

"Blood plasma concentration" refers to the concentration of compounds disclosed herein, such as, compounds of any of Formula (I), Formula (Ia), Formula (II), or Formula (III), in the plasma component of blood of a subject. It is understood that the plasma concentration of compounds of any of Formula (I), Formula (Ia), Formula (II), or Formula (III), may vary significantly between subjects, due to variability with respect to metabolism and/or possible interactions with other therapeutic agents. Likewise, values such as maximum plasma concentration (Cmax) or time to reach maximum plasma concentration (Tmax), or total area under the plasma concentration time curve ($AUC_{(0-\infty)}$) may vary from subject to subject. Due to this variability, the amount necessary to constitute "a therapeutically effective amount" of a compound of any of Formula (I), Formula (Ia), Formula (II), or Formula (III), may vary from subject to subject.

The term "ALDH3A1" as used herein, refers to ALDH3A1 from *Homo sapiens* (GenBank Accession No. AAH04102.1).

The terms "co-administration," "co-administered," or the like, as used herein, are meant to encompass administration of the selected therapeutic agents to a single patient and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (I), Formula (Ia), Formula (II), or Formula (III), other agents with which a subject is treated (e.g., a chemotherapeutic agent), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of ALDH3A1, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Compositions:

In some embodiments, provided herein is a pharmaceutical composition for cancer treatment comprising a pharmaceutically acceptable excipient and a therapeutically effective amount of a compound having the structure of Formula (I):

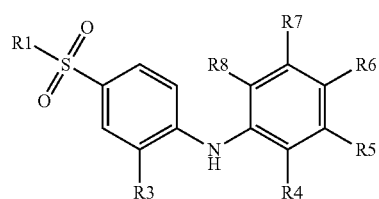

where:

R1 is selected from the R1 groups listed for the following compounds of Table 1A: CB29, Compound 2, Compound 5, Compound 9, and Compound 10;

R3 is —NO₂, —F, —OH, or —O-Me;

R4 is —H;

R5 is selected from the R5 groups listed for the following compounds of Table 1A: CB29, Compound 8, and Compound 9;

R6 is selected from the R6 groups listed for the following compounds of Table 1A: CB29, Compound 5, Compound 8, Compound 10, and Compound 11;

R7 is —H; and

R8 is —H.

In some embodiments, the pharmaceutical composition comprises a therapeutically effective amount of the compound having the structure of Formula (Ia), also referred to herein as Compound CB29:

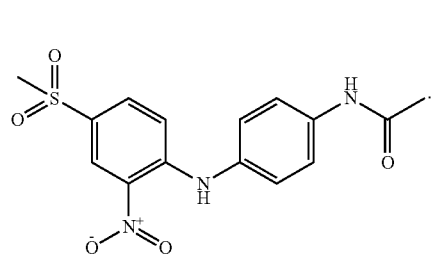

In other embodiments, the pharmaceutical composition for treating cancer includes a therapeutically effective amount of a compound having the structure of Formula (II):

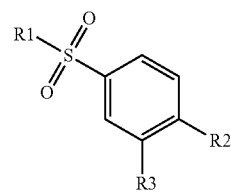

wherein:

R1 is selected from the R1 groups listed for the following compounds of Table 1B: CB29 and Compound 18;

R2 is selected from the R2 groups listed for the following compounds of Table 1B: CB29, Compound 17, and Compound 19; and R3 is —NO₂.

In further embodiments, a pharmaceutical composition for treating cancer comprises a therapeutically effective amount of a compound having the structure of Formula (III):

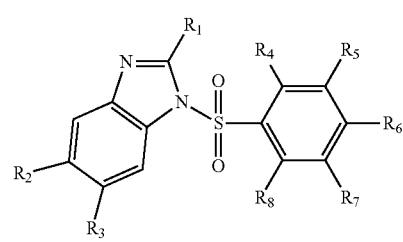

wherein:

R1 is selected from the R1 groups listed for the following compounds of Table 6: CB7, Compound A10; Compound B36, and Compound B37;

R2 is —H;

R3 is —H;

R4 is —H;

R5 is selected from the R5 groups listed for the following compounds of Table 6: CB7, Compound A53, and Compound A64;

R6 is selected from the R6 groups listed for the following compounds of Table 6: CB7, Compound A21, Compound A10, and Compound A62;

R7 is —H; and

R8 is —H; and wherein the subject is treated with one or more chemotherapeutic agents that are substrates for ALDH3A1.

Any combination of the groups for the compounds described above is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of a cancer or any other condition, disorder, or disease in which the efficacy of a therapeutic agent is reduced due to degradation of the therapeutic agent by ALD3HA1 activity. The effective amounts and concentrations are effective for ameliorating any of the symptoms of a cancer when administered to a subject treated with a therapeutic agent (e.g., a chemotherapeutic agent) that is degraded by ALDH3A1.

In some embodiments, any of the above-described pharmaceutical compositions may further include one or more chemotherapeutic agents that are substrates for ALDH3A1. Such chemotherapeutic agents that are substrates for ALDH3A1 (GenBank AAH04102.1) include, but are not limited to, paclitaxel, doxorubicin, or 4-hydroxycyclophosphamide.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

A pharmaceutical composition, as used herein, refers to a mixture of a compound described herein, such as, for example, compounds of any of Formula (I), Formula (Ia), Formula (II), or Formula (III), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the ALDH3A1-sensitive chemotherapeutic agent used to treat the subject in combination with a pharmaceutical composition described herein, severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Methods:

Described herein is a method for treating cancer comprising administering to a subject in need thereof a pharmaceutical composition comprising a therapeutically effective amount of a compound having the structure of

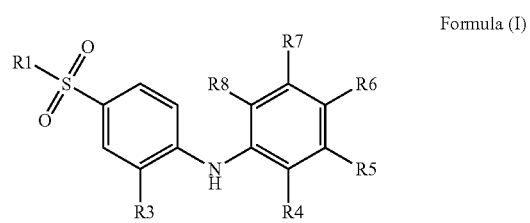

Formula (I)

wherein:
R1 is selected from the R1 groups listed for the following compounds of Table 1A: CB29, Compound 2, Compound 5, Compound 9, and Compound 10;
R3 is —NO$_2$, —F, —OH, or —O-Me;
R4 is —H;

R5 is selected from the R5 groups listed for the following compounds of Table 1A: CB29, Compound 8, and Compound 9;

R6 is selected from the R5 groups listed for the following compounds of Table 1A: CB29, Compound 5, Compound 8, Compound 10, and Compound 11;

R7 is —H; and

R8 is —H; and wherein the subject is treated with one or more chemotherapeutic agents that are substrates for ALDH3A1.

In some embodiments, the compound to be administered has the structure of Formula Ia (also referred to herein as CB29):

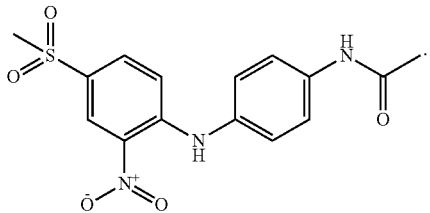

Also described herein is a method for treating cancer comprising administering to a subject in need thereof a pharmaceutical composition comprising a therapeutically effective amount of a compound having the structure of Formula (II):

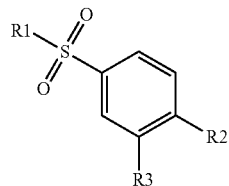

wherein

R1 is selected from the R1 groups listed for the following compounds of Table 1B: CB29 and Compound 18;

R2 is selected from the R2 groups listed for the following compounds of Table 1B: CB29, Compound 17, and Compound 19; and R3 is —NO₂.

Also described herein is a method for treating cancer comprising administering to a subject in need thereof a pharmaceutical composition comprising a therapeutically effective amount of a compound having the structure of Formula (III):

Formula (III)

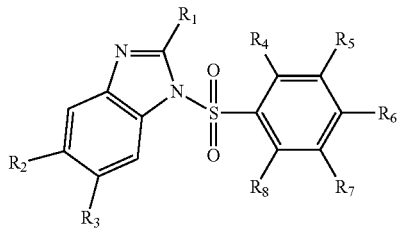

wherein:

R1 is selected from the R1 groups listed for the following compounds of Table 6: CB7, Compound A10; Compound B36, and Compound B37;

R2 is —H;

R3 is —H;

R4 is —H;

R5 is selected from the R5 groups listed for the following compounds of Table 6: CB7, Compound A53, and Compound A64;

R6 is selected from the R6 groups listed for the following compounds of Table 6: CB7, Compound A21, Compound A10, and Compound A62;

R7 is —H; and

R8 is —H; and wherein the subject is treated with one or more chemotherapeutic agents that are substrates for ALDH3A1.

In some embodiments, the subject to be treated was treated with one or more ALDH3A1-sensitive chemotherapeutic agents before administration of a pharmaceutical composition comprising any of the above-compounds disclosed herein. In other embodiments, the one or more-chemotherapeutic agents are administered to the subject after administration of any of the above-mentioned pharmaceutical compositions containing a compound disclosed herein. In other embodiments, the one or more chemotherapeutic agents are co-administered with one of the above-described pharmaceutical compositions (e.g., as a combination pharmaceutical composition).

In some embodiments, the one or more chemotherapeutic agents used to treat the subject, in combination with the pharmaceutical compositions disclosed herein, include one or more of paclitaxel, doxorubin, or 4-hydroxycyclophosphamide.

In some embodiments, the subject to be treated by one of the methods described herein, is suffering from a cancer known to overexpress ALDH3A1 relative to a corresponding non-cancerous tissue. In some embodiments the subject to be treated is suffering from hepatoma, lung adenocarcinoma, myeloma, breast cancer, colon cancer, or glioblastoma.

In some cases the treatment methods described herein also include obtaining from a subject to be treated a biological sample comprising cancer cells and determining an ALDH3A1 mRNA, protein expression, or enzymatic activity level before, during, or after treatment with the pharmaceutical composition. When done before treatment this is useful in assessing the likelihood that the cancer being treated has a high level of ALDH3A1 activity. Assessment of ALDH3A1 activity during treatment. Assessment during or soon after a treatment may be useful to confirm a reduction in ALDH3A1 activity. Optionally, a plasma level of a chemotherapeutic agent may be determined before and after co-administration of any of the pharmaceutical compositions described herein with the chemotherapeutic agent to assess the effectiveness of the pharmaceutical composition in reducing chemotherapeutic agent degradation by ALDH3A1 in the subject.

In any of the aforementioned methods, administration of a pharmaceutical composition can be oral, enteral, parenteral, or a combination of routes for administration wherein (a) the effective amount of the compound is systemically administered to the subject; (b) the effective amount of the compound is administered orally to the subject; (c) the effective amount of the compound is intravenously administered to the subject; (d) the effective amount of the compound administered by inhalation; (e) the effective amount of the compound is administered by nasal administration; or (f) the effective amount of the compound is administered by injection to the subject; (g) the effective amount of the compound is administered topically (dermal) to the subject; (h) the effective amount of the compound is administered by ophthalmic administration; or (i) the effective amount of the compound is administered rectally to the subject.

In any of the aforementioned aspects are further embodiments comprising single administrations of the effective amount of the compound, including further embodiments in which (i) the compound is administered once; (ii) the compound is administered to the subject multiple times over the span of one day; (iii) continually; or (iv) continuously.

In any of the aforementioned aspects are further embodiments comprising multiple administrations of the effective amount of the compound, including further embodiments in which (i) the compound is administered in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

The compounds described herein can be used in the preparation of medicaments for the inhibition of ALDH3A1 or for the treatment of diseases or therapeutic regimens that would benefit, at least in part, from inhibition of ALDH3A1, e.g., treatment of a cancer with an ALDH3A1-sensitive chemotherapeutic agent.

In addition, a method for treating any of the diseases or conditions described herein in a subject in need of such treatment, involves administration of pharmaceutical compositions containing at least one compound of any of Formula (I), Formula (Ia), Formula (II), or Formula (III), described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions, are administered, in combination with an ALDH3A1-sensitive therapeutic agent, to a patient already suffering from a disease or condition in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more subdoses per day.

The pharmaceutical compositions described herein may be in unit dosage forms suitable for single administration of precise dosages. In unit dosage form the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

The invention will be more fully understood upon consideration of the following non-limiting Examples.

EXAMPLES

Example 1

Development of Selective Inhibitors for Human Aldehyde Dehydrogenase 3A1 (ALDH3A1) for the Enhancement of Cyclophosphamide Cytotoxicity Aldehyde dehydrogenase 3A1 (ALDH3A1) plays an important role in many cellular oxidative processes, including cancer chemo-resistance by metabolically inactivating oxazaphosphorine drugs such as cyclophosphamide (CP) and its analogs such as mafosfamide (MFM), ifosfamide (IFM), 4-hydroperoxycyclophosphamide (4-HPCP). Compounds that can selectively target ALDH3A1 may permit delineation of its roles in these processes and could restore chemosensitivity in cancer cells that express this isoenzyme. Here we report the detailed kinetic and structural characterization of an ALDH3A1 selective inhibitor, CB29, previously identified in a high throughput screen. Kinetic and crystallographic studies demonstrate that CB29 binds within the aldehyde substrate-binding site of ALDH3A1. Cellular proliferation of ALDH3A1-expressing lung adenocarcinoma (A549) or glioblastoma (SF767) cell lines, as well as the ALDH3A1 non-expressing cell line CCD13Lu, is unaffected by treatment with CB29 and its analogs alone. However, the sensitivity toward the anti-proliferative effects of mafosfamide is enhanced by treatment with CB29 and its analog in the A549 and SF767 cells. In contrast, the sensitivity of CCD13Lu cells toward mafosfamide was unaffected by the addition of these same compounds. CB29 is chemically distinct from the previously reported small molecule inhibitors of ALDH isozymes and does not inhibit either ALDH1A1 or ALDH2, two other ALDH superfamily members with broad and overlapping substrate specificities, up to 250 µM concentration. Thus, CB29 is a novel small molecule inhibitor of ALDH3A1 which may be useful as a chemical tool to delineate the role of ALDH3A1 in numerous metabolic pathways, including sensitizing ALDH3A1 positive cancer cells toward cyclophosphamide.

Introduction.

Aldehyde dehydrogenases (ALDH) comprise a family of $NAD(P)^+$ dependent isoenzymes that catalyze the oxidation of aldehydes to their corresponding carboxylic acids. These enzymes participate in cellular homeostasis by metabolizing endogenous as well as exogenous aldehydes. Humans possess at least 19 functional members of the ALDH gene family[1]. Some important functions of these diverse enzymes include ethanol oxidation, production of retinoic acid, folate metabolism, GABA biosynthesis, as well as proline and branched-chain amino acid metabolism[1]. Several family members possess polymorphisms that impact human health. For instance, the inactive form of ALDH2 (ALDH2*2; E487K or E504K) that is present in the East Asian population is associated with impaired ethanol metabolism[2] as well as lower efficacy for nitroglycerin[3,4,5]. Modulation of ALDH2 activity can also influence cocaine addiction[6] and ischemia reperfusion injury following myocardial infarction[7,8,9]. Sjogren-Larson syndrome (SLS) is associated with an underlying genetic deficiency of ALDH3A2[10] and mutation of ALDH4A1 is associated with type II hyperprolinemia[11,12]. ALDH family members are also implicated in cancer biology, with ALDH1A1 identified as a biomarker for cancer stem cells[13,14,15]. In addition, extensive research has linked the expression of ALDH3A1 and ALDH1A1 to cancer cell proliferation, as well as to reduced sensitivity toward cyclophosphamide[16,17,18]. ALDH expression in cancer cells render these cells resistant to cyclophosphamide and its derivatives by metabolizing the intermediate, aldophosphamide, to the less toxic compound, carboxyphosphamide[17,18,19].

ALDH3A1 is a cytosolic enzyme involved in the oxidation of a variety of endogenous aldehydes, such as peroxidic and fatty aldehydes. ALDH3A1 was originally designated as the tumor ALDH as it was found highly expressed in some human tumors such as hepatoma, lung adenocarcinoma, myeloma, breast cancer and stem cell populations[20,21,22,23]. It is also expressed in some normal human tissues such as cornea and keratinocytes[18,24] Despite being present in normal cells, studies have shown that Aldh3a1(−/−) knockout mice are viable[25]. High ALDH3A1 activity in normal cells protects these cells from the products of lipid peroxidation[26], but can lead to drug resistance in tumor cells[27]. Indeed, RNAi-mediated knockdown of ALDH1A1 and ALDH3A1 in the lung adenocarcinoma cell line (A549) revealed that both enzymes contribute to the resistance against 4-hydroperoxy-cyclophosphamide, an analog of cyclophosphamide[17]. Earlier studies in cultured human colon carcinoma cell lines showed that the high ALDH3A1 expressing colon C cancer cell line is 10-fold less sensitive to mafosfamide than either the RCA or HCT 116b colon cancer cell lines. However, all three cell lines were equally sensitive to the final activated DNA alkylating agent; phosphoramide mustard[22]. Colon C cancer cells were more sensitive when mafosfamide treatment was performed in the presence of the competitive substrate, benzaldehyde[22]. When ALDH3A1 expression was induced in MCF-7 cells by treatment with 30 µM catechol for 5 days (MCF-7/CAT), the cells were over 35-fold more resistant to mafosfamide compared to control (MCF-7) cells[20], but sensitivity toward mafosfamide could be restored by inhibition of ALDH3A1 with analogs of chlorpropamide[23]. Another study showed that MCF-7 cells electroporated with ALDH3A1 were 16-fold less sensitive toward mafosfamide than control cells[28].

Recently, ALDH3A1 was identified as one of the downstream targets of metadherin (MTDH), a gene involved in multidrug chemoresistance[29]. In this study, authors showed that LM2 cells engineered to express an inducible shRNA for conditional knockdown of ALDH3A1 were more sensitive to chemotherapeutic agents such as paclitaxel, doxorubicin and 4-hydroxycyclophosphamide when ALDH3A1 was knocked down. Interestingly, overexpression of ALDH3A1 in these cells increased the chemoresistance to paclitaxel, doxorubicin and 4-hydroxycyclophosphamide[29]. Some antineoplastic agents induce apoptosis in cancer cells by producing oxidative stress through generation of lipid peroxidation products. ALDH3A1 can detoxify the products of lipid peroxidation and facilitate drug resistance under those circumstances as well. These studies highlight the role of ALDH3A1 in a broad-spectrum of cancer chemoresistance and support the development of selective and potent small molecule inhibitors.

Our laboratory recently showed that non-selective inhibition of ALDH isoenzymes enhances mafosfamide sensitivity in A549 cells[30]. However, the extent to which ALDH3A1 contributed to the observed resistance remains unknown and somewhat controversial[17,22,28,31,32,33]. We reasoned that selective inhibition of ALDH3A1 could enhance the sensitivity of chemotherapeutic agents such as cyclophosphamide as well as determine its contributions to aldophosphamide metabolism in tumor cells. In this study, we report the detailed characterization of a highly selective inhibitor for ALDH3A1, designated CB29, previously identified through the use of chemical library screening[34]. Kinetic and crystallographic studies indicate that this compound binds only to ALDH3A1 through its aldehyde binding site and does not inhibit either ALDH1A1 or ALDH2. Treatment of the ALDH3A1 expressing lung adenocarcinoma (A549) or glioblastoma (SF767) cell lines with mafosfamide in the presence of CB29, or closely related analogs, enhanced the killing effects of mafosfamide, while treatment with the compounds alone had little effect on cell proliferation. In contrast, treatment of normal lung cells (CCD13Lu) which do not express ALDH3A1 with mafosfamide in the presence of CB29 and its analogs did not increase sensitivity toward mafosfamide.

Results.

CB29 is a selective inhibitor of ALDH3A1 and does not inhibit ALDH1A1 or ALDH2.

Figure 1B:
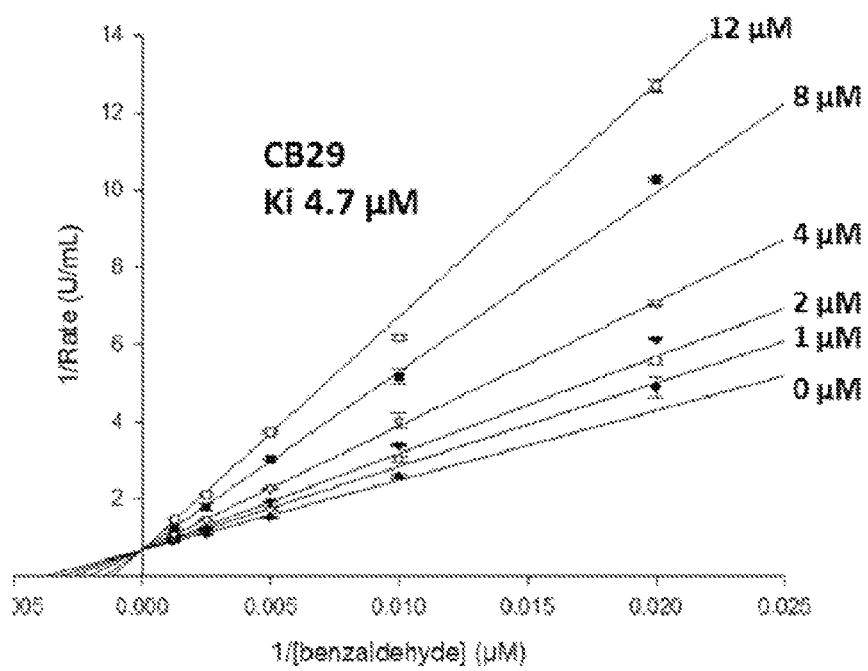
FIG. 1B. CB29 and its mode of inhibition. Lineweaver-Burk representation of the non-linear fit to the competitive inhibition equation for CB29 (1-12 μM) towards varied benzaldehyde (50-800 μM) at fixed saturating NADP+ concentration (1.5 mM). The plot is a representative single experiment of three separate experiments that were performed.

Among all the 101,000 compounds that were screened and tested for selectivity, CB29 was one of the two selective inhibitors of ALDH3A1 from the screen (Table 1A and Table 3)[34]. The chemical name for this small molecule is N-[4-{(4-(methylsulfonyl)-2-nitrophenyl)-4-amino}-phenyl]-acetamide (FIG. 1A). CB29 has a molecular mass of 349 Daltons and has little structural similarity to any known inhibitors of aldehyde dehydrogenase isoenzymes. The compound has reasonable potency for an initial hit compound against ALDH3A1 ($IC_{50}$ is 16 µM) and good selectivity toward ALDH3A1 demonstrating no inhibition (<5%) toward ALDH1A1 or ALDH2 up to 250 µM. Steady-state kinetic experiments are consistent with CB29 binding competitively to the aldehyde binding site, with a $K_i$ of 4.7±0.3 µM (FIG. 1B).

Structure of the ALDH3A1-CB29 Complex.

Figure 2A:
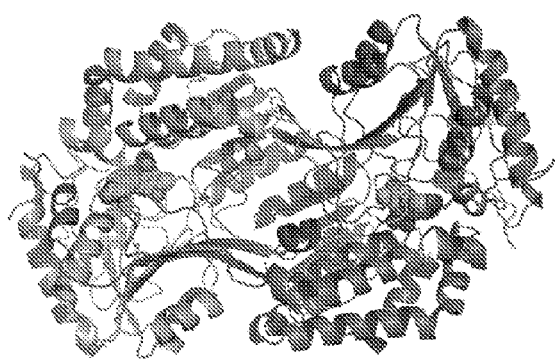
FIG. 2A. Structure of human ALDH3A1 with CB29. A ribbons representation of the ALDH3A1 dimer with the individual subunits colored orange and magenta. CB29 is shown using van der Waals spheres.
Figure 2B:
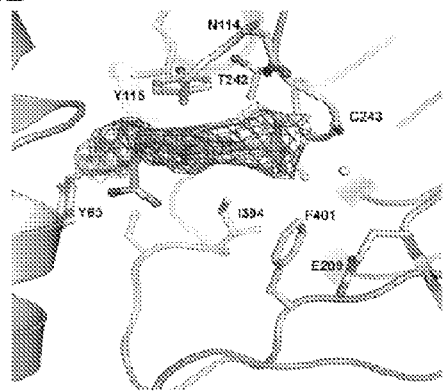
FIG. 2B. Structure of human ALDH3A1 with CB29. The active site of ALDH3A1. The electron density maps displayed are the original figure-of-merit, σ-A weighted, Fo-Fc map contoured at 2.5 standard deviations (green) and the original figure-of-merit, σ-A weighted, 2Fo-Fc map contoured at 1 standard deviation (blue) superimposed on the final refined model of CB29 bound within the ALDH3A1 substrate site. Figure was generated using PyMol for Windows, version 0.99.
Figure 2C:
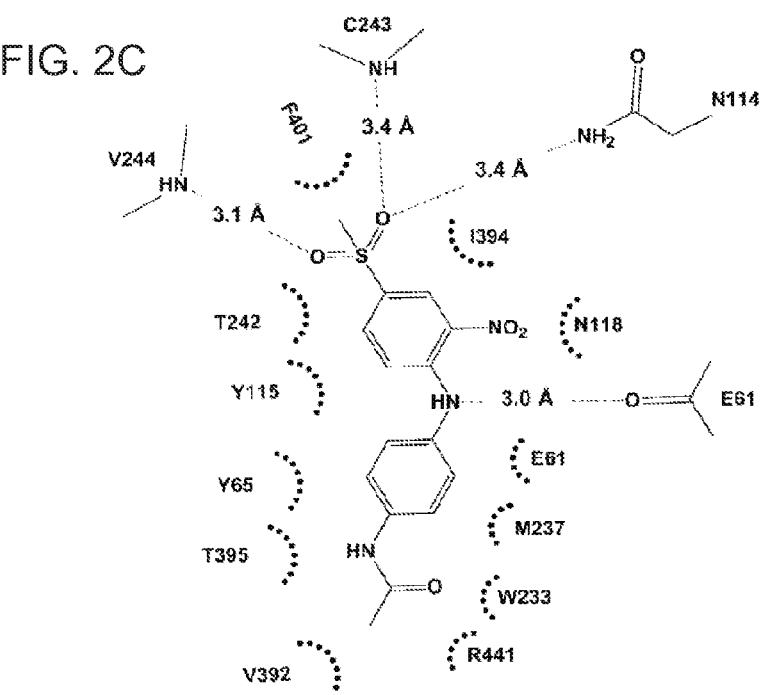
FIG. 2C. Two dimensional representation of the molecular contacts between CB29 and amino acid residues within the substrate-binding site of ALDH3A1. The red dotted lines represent potential hydrogen bonding interactions. The distance shown is the average of the distances observed in the eight subunits of the asymmetric unit. Hydrophobic contacts are represented by black arcs radiating towards the ligand.

In order to understand the specificity for ALDH3A1 and provide a structural context for the kinetic studies, we determined the crystal structure of CB29 bound to ALDH3A1. Triclinic crystals were obtained that diffracted up to 2.5 Å resolution (Table 2). Four independent dimers are present in the asymmetric unit (FIG. 2A). The presence of CB29 within the active site of ALDH3A1 was confirmed through examination of the original figure-of-merit, $\sigma_A$-weighted, electron density maps (FIG. 2B). The active site of each subunit of ALDH3A1 in the asymmetric unit is fully occupied by CB29. A Ramachandran plot of the final model demonstrates greater than 97% of all residues in the most favored regions. There are four residues Cys243, Val244, Glu61 and Asn114 that contribute hydrogen bonding interactions with CB29 (FIG. 2C). The two sulfonyl oxygens and the amino group linking the two benzene rings mediate these hydrogen bonds whereas the terminal benzylacetamide moiety contribute mostly hydrophobic and Van der Waals interactions (FIG. 2C). One of the sulfonyl oxygens forms a hydrogen bond with the peptide nitrogen of Val244. The second sulfonyl oxygen is positioned similar to the oxyanion formed during catalysis and lies in proximity to the peptide nitrogen of Cys243 and the side chain amide nitrogen of Asn114. The nitrogen linking the two substituted benzene rings in CB29 donates a hydrogen bond to the peptide carbonyl oxygen of Glu61. The methyl associated with the sulfonyl group forms a hydrophobic interaction with Phe401 and the nitro-benzene ring forms hydrophobic pi-stacking interactions with Tyr115. The side chains of Ile394 and Thr242 also contribute hydrophobic interactions with the nitro-benzene ring. The benzylacetamide ring forms hydrophobic interactions with Tyr65 and Thr395 on one side, while the opposing face interacts with the Cβ and Cγ side chain atoms of Glu61 and the side chain of Met237. The terminal acetamide group is within van der Waals contact distance to Tyr65, Trp233, Thr395, Val 392 and Arg441 (FIG. 2C).

Structure Activity Relationship of CB29 Derivatives on ALDH3A1.

We purchased 64 different compounds that showed at least 90% structural similarity in their atomic positions with CB29. These compounds were tested for their potency as inhibitors of ALDH3A1 and for their selectivity versus ALDH1A1 and ALDH2 (Tables 1A and 1B). Our results showed that only those CB29 derivatives with smaller subgroups, such as methyl or methylamine, at the R1 position were inhibitory toward ALDH3A1 (Table 1A). Substitution of the R1 position with larger substituent, such as diethylamine or morpholine, eliminated inhibitory potency for ALDH3A1, but showed weak activation of ALDH1A1 activity [Table 1A, compare CB29 ($IC_{50}$=16 µM) with 1 (NI) and 2 ($IC_{50}$=26 µM) with 3 (NI) and 4 (NI)].

Since larger substitutions were deleterious to potency, we examined whether substitution of the $CH_3$ with $CF_3$ improved potency. Replacement of the methyl group with a trifluoromethyl group ($CF_3$) at the R1 position generated an equally potent compound [Table 1A, compare CB29 ($IC_{50}$=16 µM) with 5 ($IC_{50}$=17 µM)]. We concluded that a methyl substituent was optimal at the R1 position. As our structural data (FIG. 2) indicated that the nitro group at the R3 position forms only van der Waals interactions, we examined whether analogs with a methyl sulfonyl group at this position were possible. However, this substitution yields both lower solubility (by more than 5-fold) and lower potency [Table 1A, compare CB29 ($IC_{50}$=16 µM) with 6 ($IC_{50}$=40 µM)]. In addition, this compound was less selective and inhibited both ALDH1A1 and ALDH3A1. Based on these results, we believe that the nitro group is advantageous for solubility and selectivity.

Since CB29 had a substituted aniline group at the R2 position (Table 1B), we explored a number of different substituted anilines to test their contribution to the potency and selectivity of CB29. Our results showed that an aniline at the R2 position was required for inhibition of ALDH3A1 [Table 1B, compare 15 (NI), 16 (NI) with CB29 ($IC_{50}$=16 µM), 17 ($IC_{50}$=27 µM) and 18 ($IC_{50}$=30 µM)]. Even the substitution of an ether linkage greatly reduced potency [Table 1B, compare CB29 ($IC_{50}$=16 µM) with 20 ($IC_{50}$=100 µM)]. We evaluated a series of anilines at the R2 position with substitutions at the ortho, meta and para positions. Compounds with substituents at the ortho position (R4/R8) lost all activity toward ALDH3A1 [Table 1A, 7 (NI)]. Compounds with substitutions at the meta positions (R5/R7) showed similar potencies to CB29 [Table 1A, 8 ($IC_{50}$=10 µM) and 9 ($IC_{50}$=26 µM)]. Finally, we examined substitutions at the para (R6) position.

Since our parent compound CB29 had an acetamide at this position, we looked for analogs with an ester instead of amide linkage at the corresponding position (10 and 11). This substitution yielded compounds with similar potencies [10 ($IC_{50}$=31 µM), 11 ($IC_{50}$=24 µM)], which is consistent with the structural data that shows no hydrogen bonding from this nitrogen to the enzyme. We next looked larger amide substitutions at the R6 position. Here a surprising pattern was seen, when the acetamide was substituted with isobutyramide (12) or isopentanamide (13), these two compounds were inhibitory towards both ALDH1A1 and ALDH3A1 (Table 1A). In addition, analogs with larger amides at the R6 position and larger substitutions at the R1 position (14) showed greater potency toward ALDH1A1 than toward ALDH3A1 (Table 1A). In contrast, as mentioned above when the acetamide group was held constant and the larger morpholine was introduced at the R1 position (1), the compound lost all inhibitory potency toward either ALDH1A1 or ALDH3A1.

Expression and Activity of ALDH3A1 and ALDH1A1 in Cancer Cell Lines.

Figure 3A:
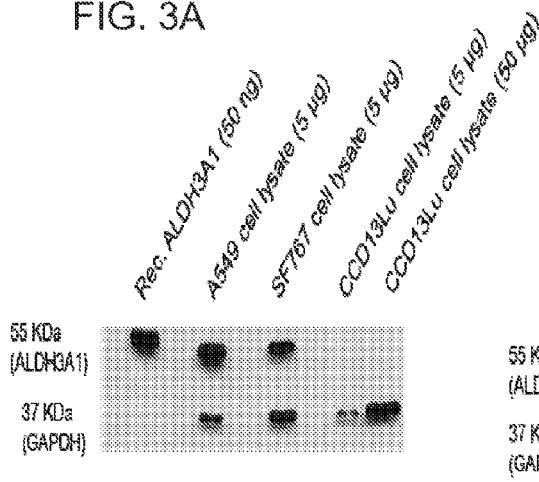
FIG. 3A. Expression and activity of ALDH1A1 and ALDH3A1 in A549, SF767, and CCD13Lu cells. Lysates from various cancer cell lines (A549, SF767 and CCD13Lu) were examined for ALDH3A1 expression.
Figure 3B:
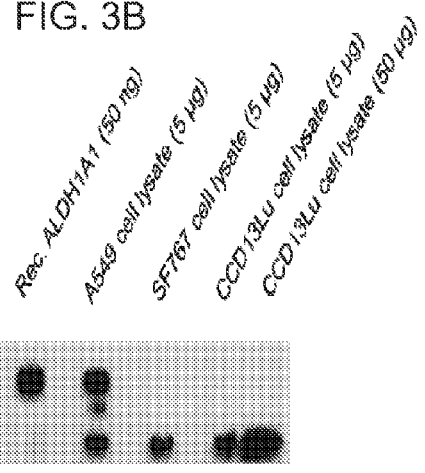
FIG. 3B. Expression and activity of ALDH1A1 and ALDH3A1 in A549, SF767, and CCD13Lu cells. Lysates from various cancer cell lines (A549, SF767 and CCD13Lu) were examined for ALDH1A1 expression.

We examined various cancer cell lines to determine the level of ALDH1A1 and ALDH3A1 expression as potential cell models for assessing the contributions of ALDH3A1 toward aldophosphamide metabolism. As previously reported[17], we found A549 cells express both ALDH1A1 and ALDH3A1 (FIGS. 3A and 3B). When we quantitated the relative expression levels of each isoenzyme by reference to purified recombinant enzyme, we find that A549 cells express ALDH1A1 and ALDH3A1 at about 1% of total cellular protein. SF767 cells also demonstrated robust ALDH3A1 expression, but lacked detectable expression of ALDH1A1 (FIGS. 3A & 3B). CCD13Lu cells had no detectable expression of either ALDH1A1 or ALDH3A1 by immunoblot.

Figure 3C:
FIG. 3C. Western blot of purified human ALDH1 and ALDH2 isoenzymes using the Abcam (ab-23375) ALDH1A1 antibody. Each lane was loaded with between 50 and 70 ng of the purified recombinant human ALDH1A1, ALDH1A2, ALDH1A3, ALDH1B1 and ALDH2 isoenzymes respectively.
Figure 3D:
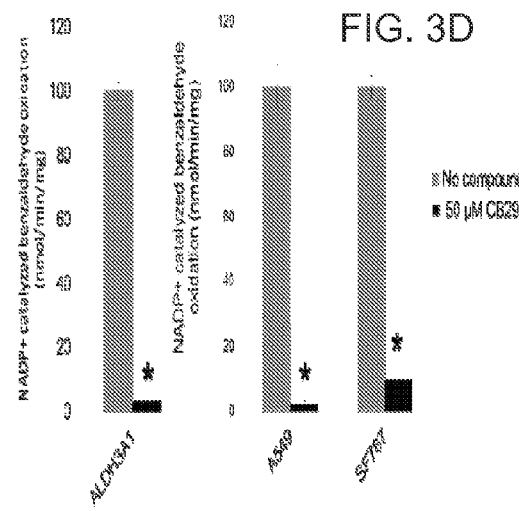
FIG. 3D. Recombinant ALDH3A1, and cell lysates from A549, SF767 and CCD13Lu cells were measured for their ability to oxidize benzaldehyde (1 mM) using NADP+ (1.5 mM) as the cofactor in the presence or absence of 50 μM CB29. CCD13Lu cell lysate did not have significant activity. The p values were calculated using the Student's t test comparing activity in the absence and presence of inhibitor (CB29) (*, p<0.001, n=3).

To confirm that protein expression correlates with ALDH activity, we performed activity assays. While benzaldehyde is a substrate for many ALDH isoenzymes, only ALDH3A1 uses $NADP^+$ as a cofactor to oxidize benzaldehyde (FIG. 3D). Enzyme activity assays on A549 cell lysates using $NADP^+$ and benzaldehyde had an activity of 282 nmol/min/mg. Based on the specific activity of recombinantly ALDH3A1 purified in our lab (32 µmol/min/mg), the activity assay confirmed the immunoblot and demonstrated that ALDH3A1 is active and present at ~1% of total lysate protein. Similarly, in SF767 cells, western blot analysis and enzyme assays show that ALDH3A1 is expressed at 1% of total cellular protein (FIG. 3D). Finally, CCD13Lu cells had no detectable ALDH1A1 or ALDH3A1 activity (FIGS. 3A, 3B and 3D). The three cell lines provide a convenient system to investigate the potentiation of mafosfamide by ALDH3A1 inhibition as A549 express both ALDH3A1 and ALDH1A1, SF767 express predominantly ALDH3A1, and CCD13Lu cell line do not express detectable levels of several ALDH isoforms.

The ability of CB29 to inhibit ALDH3A1 activity in the mixed milieu of cell lysates was examined using this activity assay (FIG. 3D). When CB29 is added to the cell lysates, the ALDH3A1 activity is diminished significantly: (>95% in A549; >90% in SF767, right panel). The activity of the recombinant ALDH3A1 also decreased by ~97% with 50 µM CB29 (FIG. 3D, left panel). CCD13Lu lysate did not exhibit ALDH3A1 associated activity (<2 nmol/min/mg). This is consistent to our western blot results that showed no expression of ALDH1A1 or ALDH3A1 on CCD13Lu cell line (FIGS. 3A and 3B). These data suggest that ALDH3A1 possess robust activity in tumor cell extracts, and that CB29 can inhibit the activity of ALDH3A1 in the context of tumor whole cell lysates.

Evaluation of the Contribution of ALDH3A1 Toward Aldophosphamide Metabolism.

Next we needed a model cell system with which to evaluate the ability of CB29 and selected analogs to penetrate the cell and influence an observable phenotype that is ALDH3A1-dependent. ALDH3A1 has been shown to directly influence cellular sensitivity to the effects of cyclophosphamide treatment[17,22,27]. We used the A549 (ALDH1A1 and ALDH3A1 expressing), SF767 (ALDH3A1 expressing) and CCD13Lu (ALDH non-expressing) cell lines to assess the overall toxicity and their ability of CB29 analogs to enhance their sensitivity toward derivatives of cyclophosphamide[20,24]. The $ED_{50}$ values for mafosfamide on the A549 and SF767 cells were 125 µM and 150 µM, respectively, while CCD13Lu cell was more sensitive to mafosfamide with an $ED_{50}$ of 40 µM. CB29 as well as compounds 17, 2, 18, 19, 11, 8, 9 and 10 were chosen because they were selective toward ALDH3A1 and showed no inhibitory potential toward ALDH1A1 and ALDH2 activity in vitro. In addition, these compounds had high solubility and could easily form a homogenous 100 µM solution in the presence of 0.25% DMSO and demonstrated the lowest general cytotoxicity at concentration as high as 100 µM. Treatment of all cell lines with mafosfamide decreased cell proliferation (FIGS. 4A and 4B, DMSO control vs. mafosfamide, 100% vs. 59±14% (A549), p<0.001, 100% vs. 68±4% (SF767), p<0.001). ALDH3A1 inhibitors 17, 2, 18, 19, 11, 8, 10 and CB29 had little effect on cell proliferation (FIGS. 4A and 4B, grey bars) as single agents. However, compound 9 was cytotoxic in both cancer cell lines (66±7% in A549, and 69±3% in SF767) at 50 µM concentration, suggesting that it may have off-target effects at this concentration and was not pursued further.

Figure 4A:
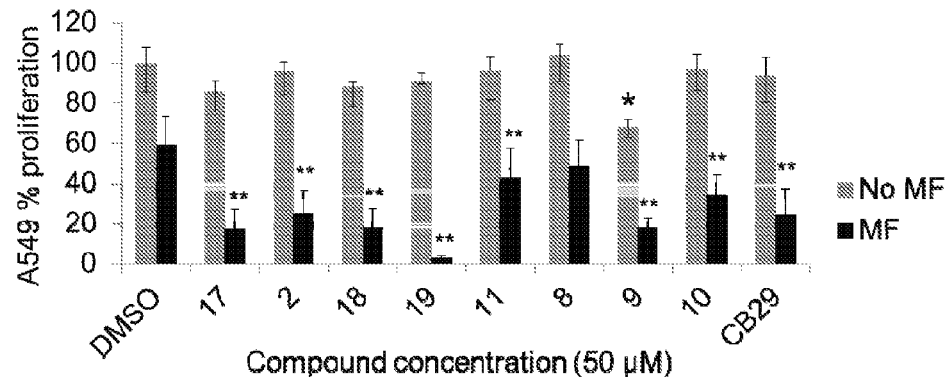
FIG. 4A. Sensitization of A549 cells to mafosfamide with ALDH3A1 inhibitors. Cells were simultaneously treated with mafosfamide (MF) in combination with ALDH3A1 inhibitors (50 μM). A549 cells treated with mafosfamide.
Figure 4B:
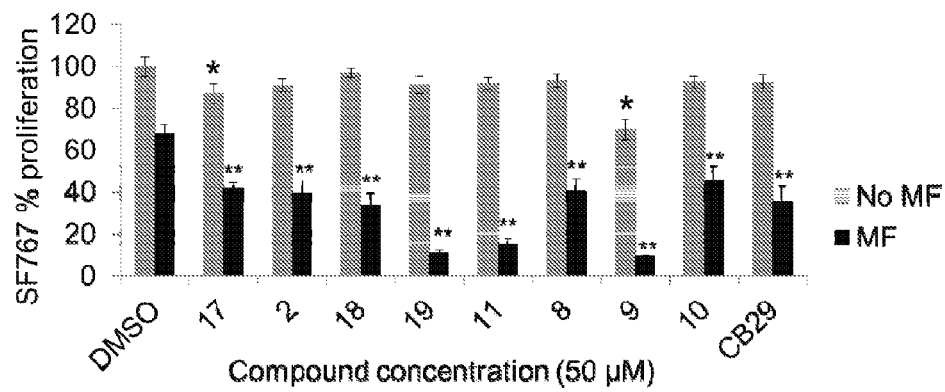
FIG. 4B. SF767 cells treated with mafosfamide (125 μM) for 19 hours.
Figure 4C:
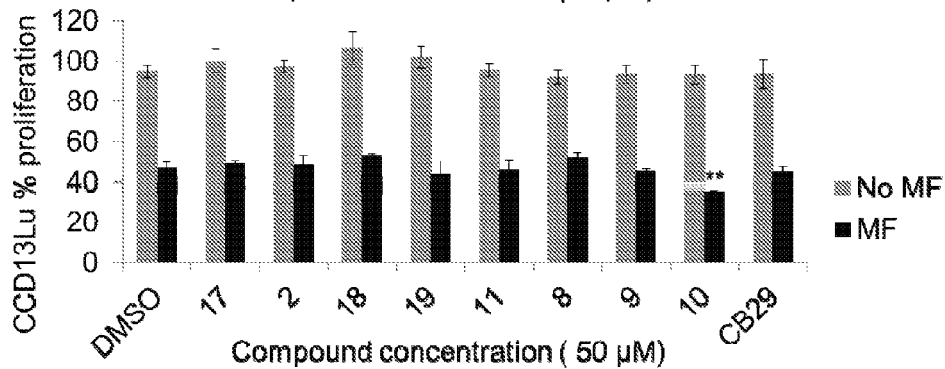
FIG. 4C. CCD13Lu cells treated with 40 μM mafosfamide for 19 hours. Cell proliferation was determined was determined using the MTT assay. The DMSO concentration was limited to 0.25% (v/v). P values were calculated by comparing the cellular proliferation of DMSO treated cells versus inhibitor treated cells (*, p<0.05, n=15) or mafosfamide (MFM) treated cells versus (MFM+50 µM Inhibitor) treated cells (**, p<0.005, n=15). Grey bars represent compound treatment alone and black bars represent compound and mafosfamide treatment. Each bar represents the mean value±SE.
Figure 5A:
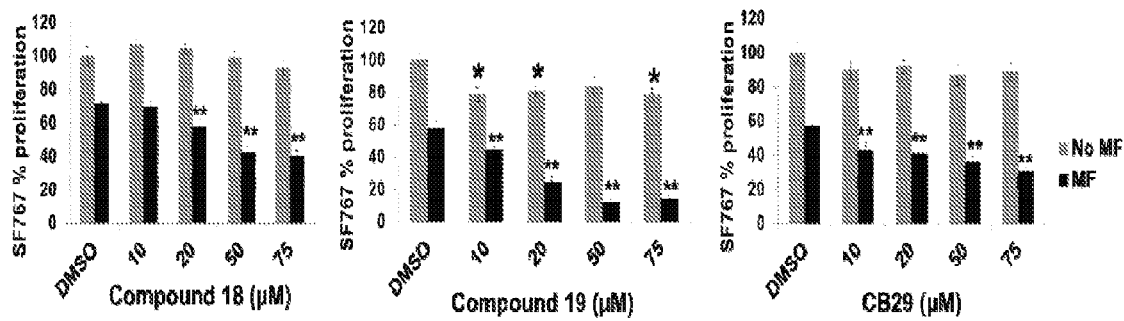
FIG. 5A. SF767 cells treated with increasing concentrations of 18, 19, and CB29 and either the presence or absence of 125 µM mafosfamide (n=10-15). P values were calculated by comparing the cellular proliferation of DMSO treated cells versus inhibitor treated cells (*, p<0.05, n=15) or mafosfamide (MFM) treated cells versus (MFM+Inhibitor) treated cells (**, p<0.005, n=15). Grey bars represent compound treatment alone and black bars represent compound and mafosfamide treatment. Each bar represents the mean value±SE.
Figure 5B:
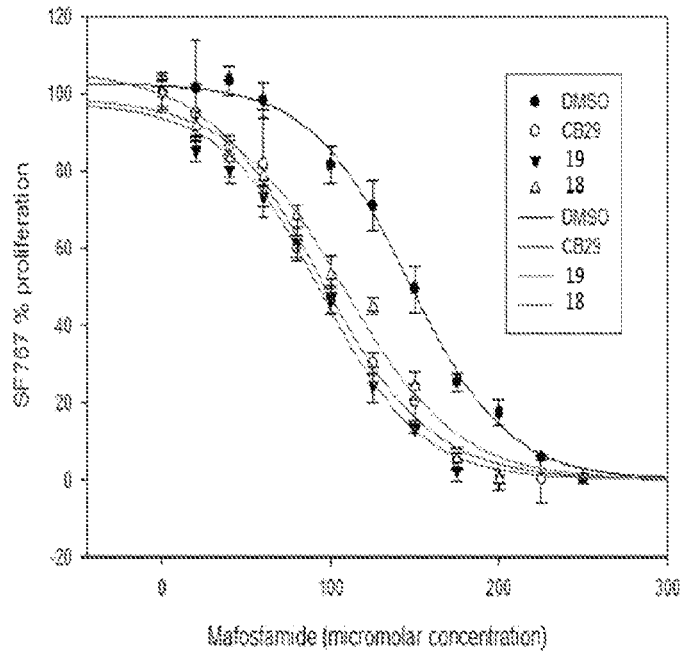
FIG. 5B. SF767 cells (10,000 cells/well) were treated with 50 µM CB29, 18 and 19 with increasing concentration of mafosfamide (0 µM-250 µM). Cell proliferation was determined using MTT assay and plot for percent (%) proliferation was created using the SigmaPlot (v11, StatSys). The DMSO concentration was limited to 0.25% (v/v) in all experiments (n=15). (Legend for figure here—circles, triangles, squares; solid lines represent the fits to the 3-parameter logistics equation; SigmaPlot, v 11.0).

Co-treatment of cells with compounds 17, 2, 18, 19, 11, 8, and CB29 increased sensitivity to mafosfamide (FIGS. 4A and 4B). Similar experiments were performed with CCD13Lu cell line and the ALDH3A1 inhibitors were neither cytotoxic nor did they significantly enhance mafosfamide sensitivity (FIG. 4C). Since SF767 cells only express ALDH3A1, we performed a dose-dependent study for sensitization toward mafosfamide in this cell line using the parent compound CB29 and the 18 and 19 analogs that also demonstrate good single dose efficacy in the A549 and SF767 cell lines (FIGS. 4A and 4B). We observed a dose-dependent enhancement in mafosfamide sensitivity as the concentration of compounds 18, 19 and CB29 increase (FIG. 5A). To calculate the shift in $ED_{50}$ value of mafosfamide in the presence of ALDH3A1 inhibitors, we conducted mafosfamide $ED_{50}$ experiment in the presence or absence of CB29, 18 and 19 in SF767 cells. Results showed that in the presence of 50 µM concentration of CB29, 18 and 19, the $ED_{50}$ value of mafosfamide drops from 146±2 µM to 92±4 µM, 108±6 µM, 94±5 µM respectively (FIG. 5B). This experiment confirmed that by using ALDH3A1 inhibitors, we can increase mafosfamide chemosensitivity.

Figure 7B:
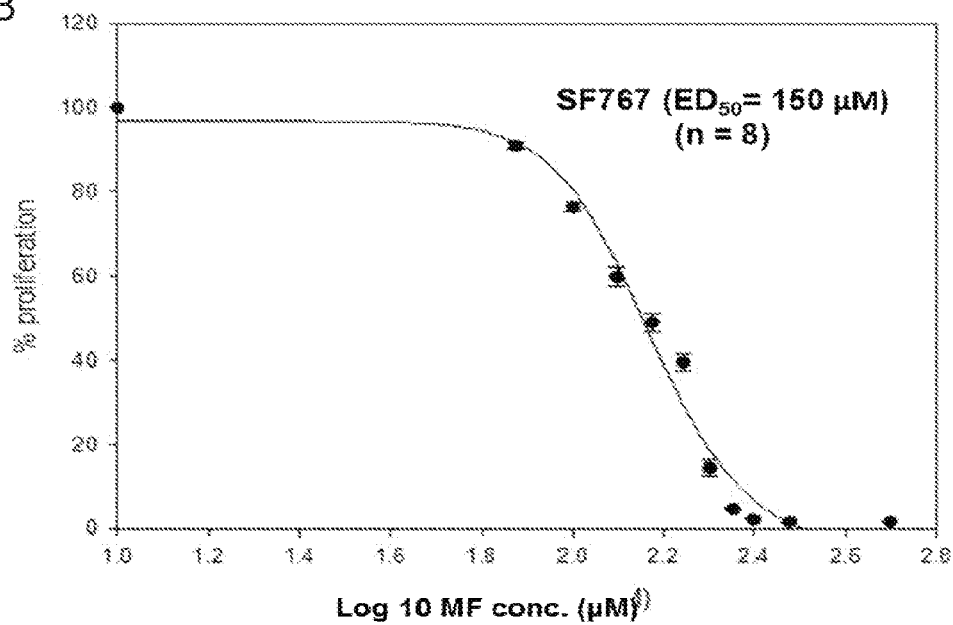
FIG. 7B. Calculation of ED50 for A549, SF767 and CCD13Lu cell lines SF767 (ALDH3A1 expressing).
Figure 7C:
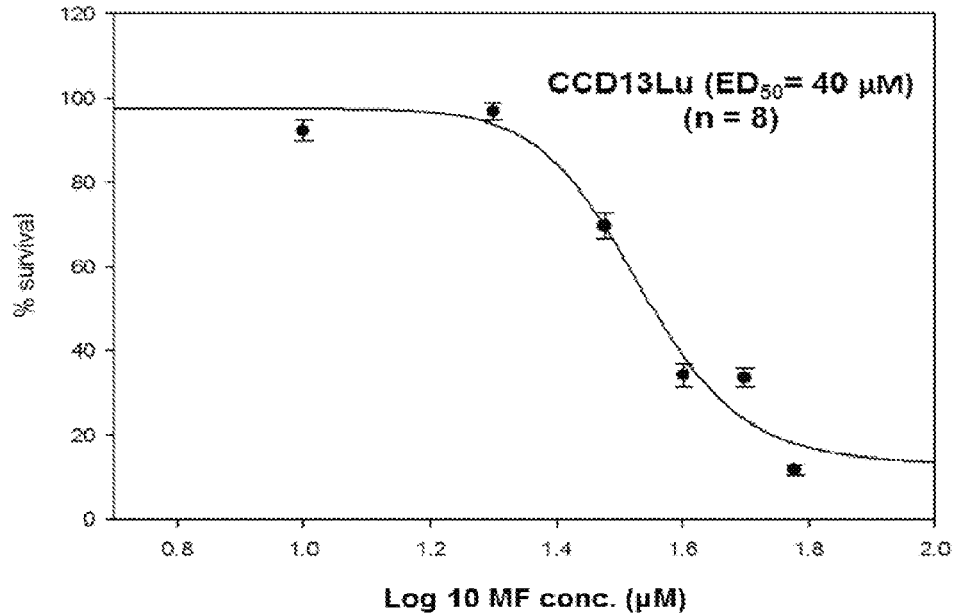
FIG. 7C. CCD13Lu (ALDH non-expressing) cell lines were used to assess the overall toxicity of CB29 analogs and their ability to enhance the sensitivity of ALDH3A1-exprdessing cell lines toward derivatives of cyclophosphamide. The ED50 values for mafosfamide on the A549 (A) and SF767 (B) cells were 125 µM and 150 µM, respectively, while CCD13Lu cell (C) was more sensitive to mafosfamide with an ED50 of 40 µM.
Figure 8A:
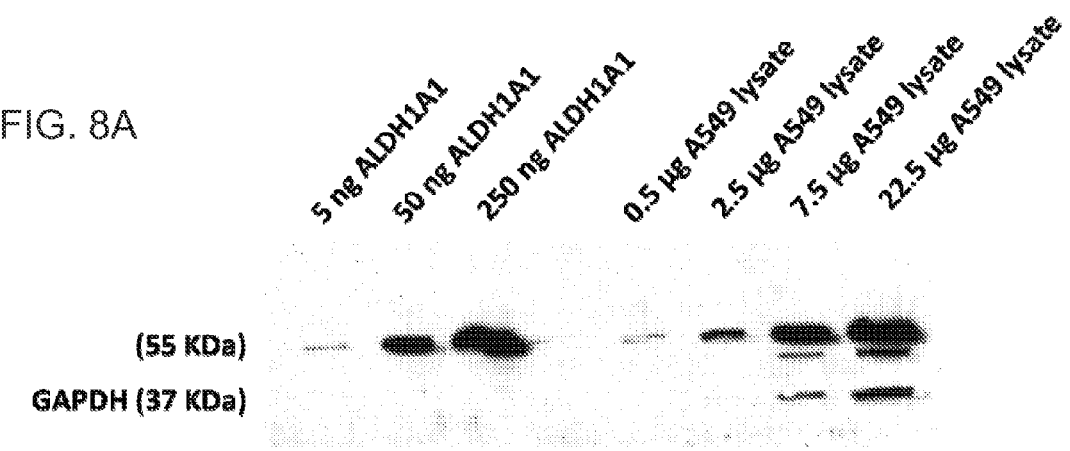
FIG. 8A. Quantitation of ALDH3A 1 Expression in A549 and SF767 Cell Lines. Quantitation of ALDH1A1 expression in A549 cell line. Serial dilutions of A549 cell lysates (0.5 µg-22.5 µg) were compared against serial dilutions of recombinantly purified ALDH1A1 (5 ng-250 ng). Purified recombinant ALDH1A1 protein served as positive control and GAPDH served as a loading control.
Figure 8B:
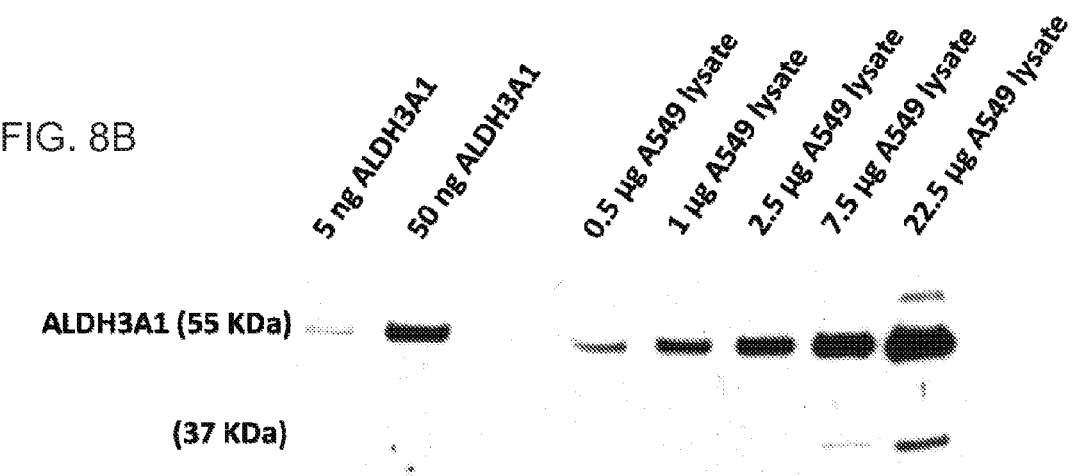
FIG. 8B. Quantitation of ALDH3A1 expression in A549 cell line. Serial dilutions of A549 cell lysates (0.5 µg-22.5 µg) were compared against serial dilutions of recombinantly purified ALDH1A1 (5 ng-50 ng). Purified recombinant His-tagged ALDH3A1 protein served as positive control and GAPDH served as a loading control.

FIG. 7 shows the $ED_{50}$ curves of mafosfamide on A549 (A), SF767 (B) and CCD13Lu (C) cells FIGS. 8A-C show immunoblots quantitating the amount of ALDH1A1 and ALDH3A1 on A549 and SF767 cells.

Discussion.

During the last decade there has been renewed interest in aldehyde dehydrogenases as their contributions to underlying biological phenotypes have been illuminated. Of particular interest has been the association of ALDH1 and ALDH3 with particular neoplastic characteristics, such as metastatic propensity[29] and stem-cell properties[13,15]. However, it is also clear that the field lacks selective and potent chemical probes with which to determine if these associations are functional or simply a consequence of a general switch in gene expression. Compounds such as DEAB are not selective for ALDH1A1 versus 1A2 or 1A3 or even ALDH3A1, for that matter. Consequently, the discovery and development of novel and selective inhibitors for ALDH isoenzymes would be of tremendous value for investigators seeking to determine the roles of these ALDH isoenzymes in these biological outcomes.

One of the most well characterized roles for both ALDH1A1 and ALDH3A1 is their involvement in the metabolic inactivation of cyclophosphamide derivatives[17,22,27]. Cyclophosphamide is an oxazaphosphorine prodrug used in the treatment of a spectrum of cancers. The action of cytochrome P450 forms 4-hydroxycyclophosphamide, which is in tautomeric equilibrium with aldophosphamide. Spontaneous beta-elimination of aldophosphamide forms acrolein and phosphoramide mustard, the latter compound is the DNA-alkylating agent that targets rapidly dividing cells. ALDH isoenzymes and ALDH1A1, in particular, are known for their ability to confer resistance to derivatives of cyclophosphamide by oxidizing aldophosphamide to the considerably less toxic compound, carboxyphosphamide[17,18,19]. The contribution of ALDH3A1 toward cyclophosphamide resistance is more controversial, with some studies supporting a role and others refuting[17,22,28,31,32,33]. We have previously shown that non-selective covalent inhibitors of ALDH family members can sensitize A549 cells to the cytotoxic effects of aldophosphamide[30], which is consistent with earlier studies in which siRNA knockdown of both ALDH1A1 and ALDH3A1 were required for maximal sensitivity to aldophosphamide[17]. What is clear from both in vitro and cell-based work is that ALDH1A1 exhibits greater catalytic efficiency toward aldophosphamide than ALDH3A1, although purified recombinant ALDH3A1 (identical to that used in these studies) exhibited "considerable activity" toward aldophosphamide[33]. These authors concluded that only upon high level of expression, does ALDH3A1 play a significant role in conferring resistance to derivatives of cyclophosphamide[33], something that both A549 and SF767 cells exhibit.

Consequently, identification of cell permeable selective inhibitors for ALDH3A1, and/or ALDH1A1, may provide a means to understand their individual contributions toward aldophosphamide metabolism. Consistent with the ability of ALDH3A1 to metabolize aldophosphamide, several of the ALDH3A1 selective inhibitors reported here enhance the anti-proliferative effects of mafosfamide in SF767 cells, which express only ALDH3A1. In fact, in the presence of ALDH3A1 inhibitors—CB29, 18, and 19, the $ED_{50}$ value of mafosfamide dropped from 146±2 µM to 92±4 µM, 108±6 µM, and 94±5 µM respectively (FIG. 5B). Of more interest is that fact that selective inhibition of ALDH3A1 in A549 cells also enhances mafosfamide sensitivity, even with the contributions of ALDH1A1 intact. This result is consistent with the RNA-knockdown studies in these same cells, where both isoenzymes appear to contribute equally to resistance[17]. In SF767 cells, where ALDH3A1 appears to the sole target, this enhancement of sensitivity increases in a dose-dependent manner (FIG. 5A). In our hands, the antibodies utilized for detection of ALDH1A1 also detect ALDH1A2, ALDH1A3, ALDH1B1, and ALDH2 (FIG. 3c), therefore SF767 appears devoid of all ALDH1 subtypes, as well as ALDH2, and is thus a good model system to study the role of ALDH3A1 in aldophosphamide metabolism. Lastly, the dose-response in SF767 cells matches reasonably the in vitro $IC_{50}$ data in which both assays produced values between 15 and 50 µM (Table 1 and FIG. 5A).

Figure 6A:
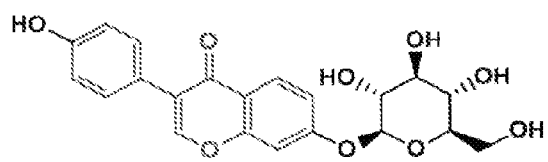
FIG. 6A. Comparison of ALDH3A1 inhibitor CB29 to ALDH2 inhibitors. Structure of daidzin. Blue region shows the planar isoflavone ring.
Figure 6B:
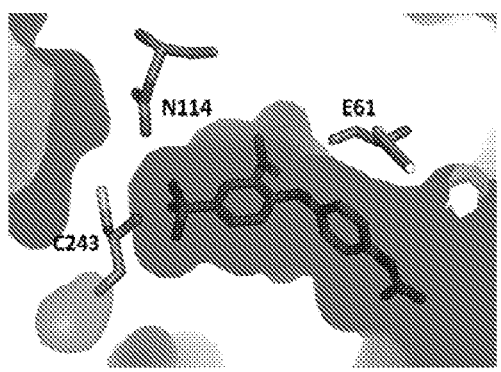
FIG. 6B. Comparison of ALDH3 A1 inhibitor CB29 to ALDH2 inhibitors. CB29 (sky-blue) bound within the substrate-binding pocket of ALDH3A1.
Figure 6C:
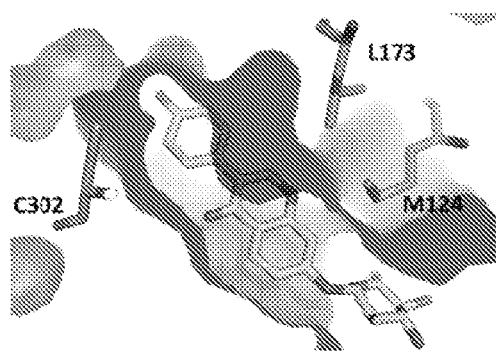
FIG. 6C. Comparison of ALDH3A1 inhibitor CB29 to ALDH2 inhibitors. Daidzin (yellow) bound within the cylindrical substrate-binding pocket of ALDH2.
Figure 6D:
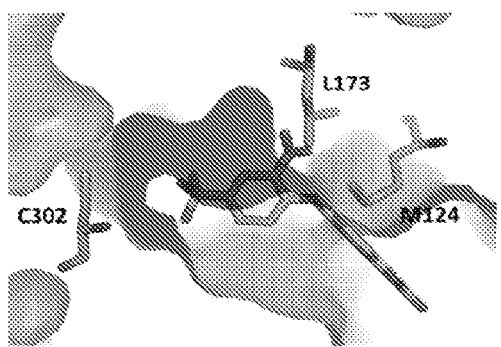
FIG. 6D. Comparison of ALDH3A1 inhibitor CB29 to ALDH2 inhibitors. Position of CB29 within the ALDH2 substrate site when the structure of ALDH3A1 is superimposed onto the structure of ALDH2 (RCSB code 1000) showing the potential steric clashes that would occur between CB29 (sky-blue) and residues within the ALDH2 substrate site.

Our steady state kinetic experiments showed that CB29 is a competitive inhibitor with respect to benzaldehyde, which is consistent with our crystallographic data where CB29 is found within the substrate-binding site. We compared the structure of ALDH3A1 catalytic site to that of ALDH2 and sheep ALDH1A1 by structural alignment to understand the selectivity of CB29 toward ALDH3A1. In particular, the structure of ALDH2 bound to daidzin (PDB accession code 2vle) provides a good basis for comparison[35]. Daidzin has a central planar isoflavone ring (FIG. 6A) linked by a single bond to a phenol moiety. This scaffold is optimal for the nearly cylindrical substrate site in ALDH2 (FIG. 6C), whereas the bent conformation conferred by the amine linkage between the two aromatic rings in CB29 is better suited to the curved nature of the ALDH3A1 site (FIG. 6B). In fact, the amine nitrogen linking the two substituted benzene rings in CB29 donates a hydrogen bond to the peptide carbonyl oxygen of Glu61 (FIG. 6D). It is interesting that substitution of the linking amine group in CB29 with an ether linkage is deleterious to potency. This difference confirms that the angle and distance geometry of the amine linkage is critical for CB29 selectivity as well contributing to its potency through hydrogen bond donation.

Figure 6E:
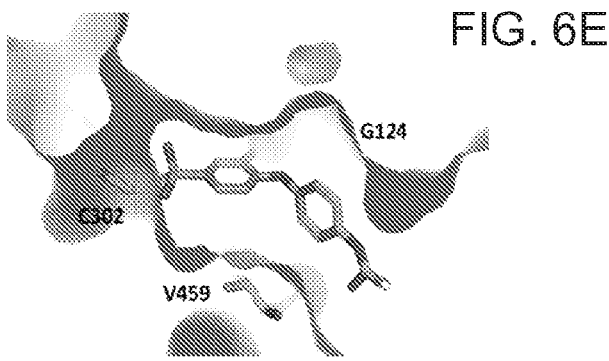
FIG. 6E. Comparison of ALDH3A1 inhibitor CB29 to ALDH2 inhibitors. Position of CB29 within the sheep ALDH1A1 substrate site when the structure of ALDH3A1 is superimposed onto the structure of sheep ALDH1A1 (RCSB code 1BXS) showing the larger available space for CB29 (sky-blue) within the ALDH1A1 substrate-binding site.

In order to understand the specificity of CB29 for ALDH3A1 over ALDH1A1, we examined the substrate-binding site of sheep liver ALDH1A1 (PDB accession code lbxs) and superimposed this structure with the human ALDH3A1 structure. Based on this alignment, we found that the substrate-binding site in human ALDH1A1 is much larger than either ALDH3A1 or ALDH2 due to the substitution of Phe459 by Val and Met124 by Gly, which widens the entrance to the substrate site considerably (FIG. 6E). We surmise that this larger substrate binding site does not sufficiently constrain CB29 for stable binding. However, analogs of CB29 with larger substituents at the R1 and R2 positions, such as 12, 13, 14 and 6, showed inhibitory activity toward ALDH1A1. Unlike ALDH1A1, ALDH3A1 cannot tolerate larger substituents at the R1 position without decreasing inhibitory potency [4, 3, 14, 1]. This trend is likely due to steric clashes that would occur with the side chains of Leu119, Tyr412 and Phe401 in this region. Our structure demonstrates that all the hydrogen bonding interactions are contributed by the substituents on the nitrobenzene ring, while the latter half of the molecule contributes primarily hydrophobic interactions (FIG. 2c). We propose that the development of more potent compounds should exploit potential hydrogen bonding interactions with the side chains of Asn118, Gln122, and His413, which would create a more even distribution of hydrogen bonding interactions along the length of the substrate-binding site.

Conclusion.

Since many exogenously administered drugs are active in their aldehyde form, identification of isozyme selective inhibitors for various ALDH isozymes will help us investigate their individual contribution toward drug metabolism. It will also help us understand the individual contribution of different forms of ALDH towards metabolism of numerous cytotoxic aldehydes, including those linked to cellular differentiation, detoxication of peroxidic aldehydes, as well as metabolism of neurotransmitters. In this study, we characterized a selective inhibitor of ALDH3A1, an enzyme implicated in aldophosphamide metabolism. Even though, the catalytic efficiency of ALDH3A1 is $1/7^{th}$ than that of ALDH1A1 for aldophosphamide in vitro[33], the expression levels in some cancer cell lines are such that its impact on aldophosphamide metabolism cannot be ignored. Indeed, some cells such as the (SF767) glioblastoma cell line only express ALDH3A1 and have $ED_{50}$ values similar to those cells in which both enzymes are expressed in similar levels (A549). Our study showed that cancer cell lines that express ALDH3A1 (SF767 and A549) can be sensitized to mafosfamide in the presence of our inhibitors whereas normal cell lines that lack ALDH3A1 expression (CCD13Lu) are not. Our current inhibitor is of modest potency ($K_i$ of 4 µM) and required higher concentration of inhibitor in our cell based assays (50 µM).

Similar results are seen for the structurally unrelated class of compound, CB7 that inhibits ALDH3A1[36]. These compounds were more potent than the CB29 class with $K_i$ values in the range of 0.1-1 µM in vitro. Interestingly, mafosfamide chemosensitivity experiments required a higher relative dosage (100-fold over $K_i$, versus 10-fold over $K_i$ for CB29) which clearly demonstrates that in vitro potency does not always predict potency in cells. Our structural data and kinetic data will facilitate the design and synthesis of more potent compounds that may eventually permit a similar phenotypic effect at lower concentrations. These selective inhibitors can be used to manipulate the contributions of ALDH3A1 toward aldophosphamide metabolism, as well as other biologically relevant aldehydes.

Methods and Materials.

Materials.

Benzaldehyde, propionaldehyde, para-nitrophenylacetate, $NAD^+$, $NADP^+$ and buffers were all purchased from Sigma Aldrich unless otherwise stated. The chemical libraries for performing high throughput screening were purchased from ChemDiv Corp. and ChemBridge Corp. Mafosfamide was bought from Niomech-IIT GmbH, Bielefeld, Germany. Primary ALDH3A1 antibody was purchased from Santa Cruz Biotechnology (sc-67310); primary ALDH1A1 antibody was purchased from Abcam (ab-23375) and primary GAPDH antibody was purchased from Abcam (ab9484).

Cloning, Protein Purification and Activity Measurement.

Human ALDH1A1, ALDH2 and ALDH3A1 were expressed and purified as described elsewhere[30,34,37]. The enzymatic activity of ALDH1A1, ALDH2 and ALDH3A1 were monitored by calculating the increase in absorbance at 340 nm due to NAD(P)H formation (molar extinction coefficient of 6220 $M^{-1}$ $cm^{-1}$) in 100 mM sodium hydrogen phosphate buffer, pH 7.5 as described elsewhere[30,34,38]. The enzymatic activity of ALDH1A1, ALDH2 and ALDH3A1 were measured as described previously[30,34,37,39]. The specific activities of the purified proteins were 1.9, 3.8 and 32 μmole/min/mg for ALDH1A1, ALDH2 and ALDH3A1 respectively.

Inhibitors.

CB29, one of the selective ALDH3A1 inhibitors discovered in our initial chemical screen[34], was purchased from ChemBridge Corp. A structural search was performed using Pubchem in order to identify commercially available analogs with at least 90% structural similarity to CB29. Over 60 compounds were purchased from ChemBridge Corp. and ENAMINE Ltd., Kiev, Ukraine and Indiana University Chemical Synthesis and Organic Drug Lead Development Core. The purity of the compounds according to the vendor was >95%. Compounds were dissolved and diluted in 100% DMSO and stored at −20° C. The analogs were tested for their selectivity against ALDH1A1 and ALDH2 and ALDH3A1 at 100 μM. Compounds that showed selectivity for ALDH3A1 were designated as follows; 1—(ENAMINE-T05126153), 2—(ENAMINE-T5477154), 3—(ENAMINE-T6032083), 4—(ENAMINE-T5237743), 5—IUSC12415, 6—IUSC12416, 7—(ENAMINE-T6036772), 8—(ENAMINE-T6241917), 9—(ENAMINE-T6560452), 10—(ENAMINE-T5477155), 11—(ENAMINE-T5655673), 12—(ENAMINE-T6245968), 13—(ENAMINE-T6053724), 14—(ENAMINE-T6536700), 15—(Chembridge Corp.—5119656), 16—(Chembridge Corp.—6809058), 17—(ENAMINE-T56333437), 18—(ENAMINE-T5395179), 19—(ENAMINE-T5804455) and 20—IUSC12417.

$IC_{50}$ Determination and Competition Experiments.

$IC_{50}$ values were determined for CB29 and its analogs using propionaldehyde as the substrate for ALDH1A1 and ALDH2 or benzaldehyde as the substrate for ALDH3A1. The assays were performed on a Beckman DU-640 spectrophotometer at various concentrations of inhibitors ranging from 50 nM to 250 μM following a 1 minute pre-incubation. There was no pre-incubation time-dependence to the inhibition. All reactions were initiated by the addition of the aldehyde substrate. The inhibition curves were fit to the Logistic four parameter $IC_{50}$ equation using the SigmaPlot (v11, StatSys). We characterized the mode of inhibition using steady-state kinetics through co-variation of inhibitor and substrate concentrations. The steady state kinetic measurements were performed in 100 mM $Na_2HPO_4$ buffer, pH 7.5. The reaction mixture contained 10 nM ALDH3A1, varied benzaldehyde (50 μM-800 μM; fixed $NADP^+$, 1.5 mM) and varied inhibitor concentrations. In all cases—including the control reactions lacking inhibitors, the final reaction mixture contained 2% (v/v) DMSO. The reaction was initiated by addition of substrate and the initial rate of product formation was determined on a Beckman DU-640. All data were fit to the non-linear velocity expressions for competitive, non-competitive, mixed-type non-competitive and uncompetitive inhibition[40]. Appropriateness of the inhibition model was determined through analysis of goodness-of-fit and the residuals of those fits. Lineweaver-Burke plots were created using SigmaPlot (v11, StatSys) to visualize the inhibition patterns. All data represent the average of three independent experiments utilizing triplicate assays at each concentration point.

Preparation and Crystallization of ALDH3A1 with CB29.

ALDH3A1 crystals were grown from solutions containing 0.2 M potassium acetate, 20% PEG 3350 at 25° C. The enzyme concentration was between 3 and 3.5 mg/mL in 10 mM HEPES buffer, pH 7.5. Two crystal morphologies form under these conditions; orthorhombic plates and triclinic parallel-pipeds. The triclinic ALDH3A1 crystals were initially soaked with 2% DMSO for 24 hours followed by another 24 hour soak with 500 μM CB29 [2% (v/v) DMSO final]. Crystals were frozen directly in gaseous nitrogen stream at 100K without additional cryoprotectant. Datasets were collected at a wavelength of 0.9869 Å at 100 K at the Advanced Photon Source using the GM/CA-CAT beamline 23-ID located at Argonne National Laboratory. The diffraction data was indexed, integrated and scaled using the HKL3000 program[41]. All refinements were performed using the program package Refmac5 as implemented in the CCP4 program suite[41] and model inspection and building was accomplished using Coot[42]. Structure of CB29 bound to ALDH3A1 was solved using the apo-form of ALDH3A1 structure as the search model (RCSB code 3SZA). Molecular replacement was performed using MolRep program provided by CCP4 Interface software. Initial maps showed clear electron density for the CB29 ligand bound on the active site of each monomer in the asymmetric unit. Atomic co-ordinate of CB29 was included in later stages of refinement. Water molecules were added after the addition of ligands in order to obtain an unbiased map for ligands. Ligand maps were sketched in Sketcher (provided by CCP4). This structure was used to create library description file and a coordinate file for the ligand, which were later used for refinement.

Cell Culture and Western Blot Analysis.

A549, CCD13Lu and SF767 cell lines were provided by Dr. Hua Lu, Dr. Melissa L. Fishel, and Dr. Karen Pollok, respectively. Cells were cultured under same conditions as described earlier[36]. Cells (A549, SF767 and CCD13Lu) were washed with ice cold PBS to remove residual media. 400 μL of RIPA buffer (Cell signaling technologies) containing 1 mM PMSF (Sigma Aldrich) was added to each 10 cm dish. Plates were incubated on ice for 5 minutes, scraped and lysates were collected. Lysates were centrifuged for 10 minutes at 16,000×G in a micro-centrifuge at 4° C. Protein concentrations were measured using the Bradford reagent (Biorad Laboratories). A549, SF767 and CCD13Lu cell lysates were resolved in 10% SDS-PAGE. ALDH3A1 antibody was used at a dilution of 1:5000 and ALDH1A1 antibody was used at a dilution of 1:1000. GAPDH (1:5000) was used as a loading control. Proteins bound to antibodies were visualized using a HRP chemiluminescence blot detection solution prepared in our lab.

Cell Lysate Activities in the Presence and Absence of CB29.

A549, SF767 and CCD13Lu cell lysates were collected exactly the same way as described before and 50 μg of cell lysate was used in the activity assay. ALDH3A1 activity in cell lysates were measured in 100 mM $Na_2HPO_4$ buffer at pH 7.5, with 1.5 mM $NADP^+$, 1 mM benzaldehyde. Activity assay was also performed with 1 μg of recombinant ALDH3A1 in the presence and absence of CB29. All assays contained 1% (v/v) DMSO. CB29 was tested at 50 μM concentration to monitor the extent of ALDH inhibition in these cell lysates and purified ALDH3A1. Lysates were treated with CB29 for 1 minute before the substrate was added.

Colorimetric MTT Assay for Mafosfamide Sensitivity.

The MTT assay was used to measure the extent of mafosfamide chemosensitivity. Mafosfamide was used for this study primarily because it is an analog of cyclophosphamide that does not require cytochrome P450 for its activation which is ideal for cell based studies[43]. The MTT assay was optimized for three cell line such that the number of cells utilized for the experimental treatments corresponded to the linear range of the assay measurements. Three cell lines, A549, SF767 and CCD13Lu were chosen for this study. These cell lines were chosen because our western blot results showed that A549 expresses ALDH1A1 and ALDH3A1, SF767 express only ALDH3A1 whereas CCD13Lu express neither of these enzymes. CCD13Lu was also relevant for this study because it is normal lung cell line which serves as a proper control for A549, which is a carcinogenic cell line from lung. The results of these standardization measurements indicated that 5000 cells/well was optimal for A549 and CCD13Lu and 10,000 cells/well was optimal for the SF767 cell line.

An optimization trial was performed for lung adenocarcinoma (A549), glioblastoma (SF767) and normal lung cell line (CCD13Lu) to find the approximate $ED_{50}$ value of mafosfamide; 125 µM for A549 cells, 150 µM for SF767 cells and 40 µM for CCD13Lu cells. Following optimization, A549 (5,000 cells/well), SF767 (10,000 cells/well) and CCD13Lu (5,000 cells/well) cells were seeded in 96 well plates. After 29 hours, A549 and SF767 cells were treated with ALDH3A1 inhibitors (17, 2, 18, 19, 11, 8, 9, 10, CB29) in the absence or in the presence of 125 µM mafosfamide. The MTT assay was carried out following 19 hours of incubation with the inhibitors (0.25% DMSO) and/or mafosfamide[36]. The relative percentage of cell proliferation was calculated in comparison to DMSO (0.25%) treated controls. The time points for treatment were chosen based on similar experiments performed earlier[30,36].

Table 1. SAR for CB29-based compounds. (A) SAR study for analogs having aniline at R3 position but with ortho, meta and para substitutions at various positions (R4, R5, R6, R7 and R8). Also included are compounds with substitutions at R1 and R3 positions. (B) SAR showing the effect of first set of analogs that had substitutions other than aniline at R3 position (such as halogen, glycine and ethers). Values in parentheses are S.D. for three independent assays. NI stands for no inhibition at 100 µM inhibitor concentration. WA represents (30-50) % activation shown by 100 µM compound to respective enzymes. Shaded are the residues of ALDH3A1 that are in close proximity with of CB29.

TABLE 1A

| Name | R1 | R3 | R4 | R5 | R6 | R7 | R8 | ALDH3A1 | ALDH2 | ALDH1A1 |
|---|---|---|---|---|---|---|---|---|---|---|
| CB29 | $CH_3$ | $NO_2$ | H | H | NHC(O)CH₃ | H | H | 16 (0.5) | NI | NI |
| 1 | morpholino | $NO_2$ | H | H | NHC(O)CH₃ | H | H | NI | NI | NI |
| 2 | $NHCH_3$ | $NO_2$ | H | H | F | H | H | 26 (1.2) | NI | NI |
| 3 | diethylamino | $NO_2$ | H | H | F | H | H | NI | NI | WA |
| 4 | diethylamino | $NO_2$ | H | H | $CH_2CH_3$ | H | H | NI | NI | WA |
| 5 | $CF_3$ | $NO_2$ | H | H | N(CH₃)₂ | H | H | 17 (0.8) | WA | NI |
| 6 | $CH_3$ | $SO_2CH_3$ | H | H | NHCH₂-cyclopentyl | H | H | 40 | NI | 32 (3) |
| 7 | $CH_3$ | $NO_2$ | $CH_3$ | H | H | $CH_3$ | H | NI | NI | WA |
| 8 | $CH_3$ | $NO_2$ | H | F | $CH_3$ | H | H | 10.8 (0.1) | NI | WA |

TABLE 1A-continued

[Structure: sulfonyl-phenyl-NH-phenyl scaffold with residue labels V243, C242, W233, F401, Y115, E209, N114, N118, E61, Y65 and positions R1, R3, R4, R5, R6, R7, R8]

| Name | R1 | R3 | R4 | R5 | R6 | R7 | R8 | IC$_{50}$ (micromolar) ALDH3A1 | ALDH2 | ALDH1A1 |
|---|---|---|---|---|---|---|---|---|---|---|
| 9 | HN-iPr (NH-isopropyl) | NO$_2$ | H | HN-iPr (NH-isopropyl) | H | H | H | 26.3 (4) | NI | WA |
| 10 | NHCH$_3$ | NO$_2$ | H | H | OCH$_3$ | H | H | 31.7 (2.6) | NI | NI |
| 11 | NHCH$_3$ | NO$_2$ | H | H | OCHF$_2$ | H | H | 24.7 (1.2) | NI | NI |
| 12 | CH$_3$ | NO$_2$ | H | H | NHC(O)CH(CH$_3$)$_2$ | H | H | 19.6 (3.3) | NI | 16.8 (2) |
| 13 | NHCH$_3$ | NO$_2$ | H | H | NHC(O)CH$_2$CH(CH$_3$)$_2$ | H | H | 42.3 (1.5) | NI | 11.6 (6) |
| 14 | N(CH$_2$CH$_3$)$_2$ | NO$_2$ | H | H | NHC(O)CH(CH$_3$)$_2$ | H | H | 100 | NI | 8.3 (3) |

TABLE 1B

[Structure: R1-SO$_2$-phenyl with R2 and R3 substituents]

| Name | R1 | R2 | R3 | IC$_{50}$ (micromolar) ALDH3A1 | ALDH2 | ALDH1A1 |
|---|---|---|---|---|---|---|
| 15 | CH$_3$ | Br | NO$_2$ | NI | NI | NI |
| 16 | CH$_3$ | NH-CH(CH$_3$)-COOH | NO$_2$ | NI | NI | 50 (6.6) |
| CB29 | CH$_3$ | NH-C$_6$H$_4$-NHC(O)CH$_3$ | NO$_2$ | 16.0 (0.5) | NI | NI |

TABLE 1B-continued

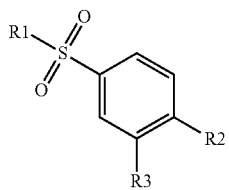

| Name | R1 | R2 | R3 | IC$_{50}$ (micromolar) ALDH3A1 | ALDH2 | ALDH1A1 |
|------|----|----|----|-------|-------|---------|
| 17 | CH$_3$ | (indanyl-NH-) | NO$_2$ | 26.9 (6.0) | NI | NI |
| 18 | (isopropyl-NH-) | (indanyl-NH-) | NO$_2$ | 30.5 (3.5) | NI | NI |
| 19 | (isopropyl-NH-) | (piperidinyl-acetamide-phenyl) | NO$_2$ | 25.6 (2.3) | NI | NI |
| 20 | CF$_3$ | (4-acetamidophenoxy) | NO$_2$ | 100 | NI | NI |

TABLE 2

X-ray data collection and refinement statistics for ALDH3A1 soaked with CB29.

| Data collection | ALDH3A1 (CB29 soak) |
|---|---|
| Space group | P1 |
| Cell dimensions | a = 89.1 Å, b = 95.4 Å, and c = 117.2 Å |
|  | α = 112.4°, β = 91.7°, and γ = 91.0° |
| Resolution (Å) | 50 – 2.50 (2.5) |
| R$_{merge}$ | 0.067 (0.25) |
| I/σ$_I$ | 10.4 (3.1) |
| Completeness | 93.6% |
| Redundancy | 2.2 |
| Refinement |  |
| Resolution (Å) | 50.0 – 2.5 |
| No. of reflections | 109,547 |
| R$_{work}$/R$_{free}$ | 0.23/0.25 |
| No. of atoms |  |
| Protein | 28003 |
| Ligand/Ion | 192 |
| Water | 218 |
| B-factor (overall) | 25.2 |
| RMSD Bond angles (°) | 1.15° |
| RMSD Bond lengths (Å) | 0.008 Å |

TABLE 3

Steps for High Throughput Screen

| S. No. | Steps for screening | Compounds |
|---|---|---|
| 1 | In-vitro absorbance based kinetic screen using esterase assay | 101,000 |
| 2 | Compounds with >60% inhibition | 436 |
| 3 | Secondary screen by cherry-picking the initial hits | 71 |
| 4 | Validation of inhibitors using dehydrogenase assay | 55 |
| 5 | Structural classification of compounds | 55 |
| 6 | Testing specificity against ALDH1A1 and ALDH2 | 55 |
| 7 | IC$_{50}$ determination for selective inhibitors | 2 |
| 8 | Selective inhibitors | 2 |

TABLE 4

Screening Hit Compounds:
(A) Hits from ChemDiv Screen:

| | | IC$_{50}$ (micromolar) | | |
|---|---|---|---|---|
| | | ALDH1A1 | ALDH2 | ALDH3A1 |
| CD4 | | 21.2 | 1.4 | 2.5 |
| CD5 | | 8.2 | 1.2 | 1.5 |
| CD7 | | 0.7 | NI | 25.5 |
| CD8 | | 0.8 | 11.1 | 6.3 |
| CD10 | | 4.0 | 2.2 | 3.4 |
| CD11 | | 5.9 | 6.5 | 10.2 |

TABLE 4-continued
Screening Hit Compounds:
(A) Hits from ChemDiv Screen:
| | | IC$_{50}$ (micromolar) | | |
| --- | --- | --- | --- | --- |
| | | ALDH1A1 | ALDH2 | ALDH3A1 |
| CD12 | (structure) | 4.2 | 5.3 | 5.6 |
| CD3 | (structure) | 6.5 | 41.8 | 38.5 |
| CD13 | (structure) | 6.3 | 7.3 | 60 |
| CD14 | (structure) | 10.4 | 13.7 | 71.5 |
| CD20 | (structure) | 33 | NI | 41 |
TABLE 4(B)
Hits from ChemBridge Screen:
| | | Inhibition patterns | | |
| --- | --- | --- | --- | --- |
| | | % inhibition @ 10 micromolar concentration | | |
| | | ALDH1A1 | ALDH2 | ALDH3A1 IC$_{50}$ (micromolar) |
| CB1 |  | >50% | NI | 3.7 |

TABLE 4(B)-continued

| | Hits from ChemBridge Screen: | | | |
|---|---|---|---|---|
| CB2 | 3,4-difluorophenyl-NH-CH2-(2-nitrophenyl) | <20% | NI | 5.2 |
| CB12 | 1-(benzo[d][1,3]dioxol-5-yl)-3-(diethylamino)propan-1-one | NI | >50% | 3.2 |
| CB13 | 1-(2,3-dihydrobenzo[b][1,4]dioxin-6-yl)-3-morpholinopropan-1-one | <20% | NI | 11.7 |

| | | % activity left after treating with 10 micromolar inhibitor | | |
|---|---|---|---|---|
| | | ALDH1A1 | ALDH2 | ALDH3A1 |
| CB41 | (E)-3-bromo-N,N-dimethyl-4-(2-nitrovinyl)aniline | 100% (NI) | 90% (NI) | 45% (I) |
| CB35 | (E)-1-(allyloxy)-2-methoxy-4-(2-nitrovinyl)benzene | 100% (NI) | 86% (NI) | 46% (I) |
| CB36 | (E)-1-(2-nitrovinyl)-4-(prop-2-yn-1-yloxy)benzene | 93% (NI) | 76% (NI) | 30% (I) |
| CB38 | (E)-2-bromo-1-methoxy-4-(2-nitrovinyl)benzene | 90% (NI) | 83% (NI) | 40% (I) |
| CB40 | (E)-2-iodo-1-methoxy-4-(2-nitrovinyl)benzene | 95% (NI) | 67% (NI) | 30% (I) |

TABLE 4(B)-continued

Hits from ChemBridge Screen:

| ID | Structure | | | |
|---|---|---|---|---|
| CB42 | (nitro-methoxy-propargyloxy-chloro styrene) | 100% (NI) | 74% (NI) | 46% (I) |
| CB37 | (nitro-bromo-methyl styrene) | 100% (NI) | 83% (NI) | 30% (I) |
| CB26 | (nitro-ethoxy-hydroxy styrene) | 100% (NI) | 88% (NI) | 45% (I) |
| CB39 | (nitrovinyl-furan-bromomethylphenyl) | 100% (NI) | 82% (NI) | 32% (I) |
| CB11 | (chlorophenyl-imidazobenzimidazole-propanol) | 100% (NI) | 96% (NI) | 61% (I) |
| CB5 | (2-(4-aminophenyl)quinoline-4-carboxylate) | 107% (NI) | 100% (NI) | 34% (I) |
| CB32 | (fluorophenyl-furan-propanoate) | 100% (NI) | 84% (NI) | 36% (I) |
| CB16 | (dimethyl-dihydroquinoxalinone-acetamide) | 100% (NI) | 100% (NI) | 50% (I) |

TABLE 4(B)-continued

Hits from ChemBridge Screen:

| ID | Structure | | | |
|---|---|---|---|---|
| CB3 | 4-chloro-5-methyl-2-nitrophenoxyacetic acid | 71% (NI) | 100% (NI) | 55% (I) |
| CB21 | N-methyl-N-(6-nitrobenzothiazol-2-yl)glycine | 104% (NI) | 100% (NI) | 58% (I) |
| CB23 | N-(furan-2-ylmethyl)-2-(phenylthio)acetamide | 110% (NI) | 94% (NI) | 65% (I) |
| CB6 | 2-(cyclohexylamino)-4,5-dihydrothiazol-5-yl thiocyanate | 12% (NI) | 44% (NI) | 6% (I) |
| CB14 | 1-(2-fluoro-4-nitrophenyl)pyrrolidine | 91% (NI) | 97% (NI) | 47% (I) |
| CB4 | 4-methyl-6-(2,3-dihydro-1H-indol-3-yl)-2H-pyran-2-one | 71% (NI) | 100% (NI) | 60% (I) |
| CB10 | 2-(1H-benzimidazol-2-yl)-3-[4-(4-chlorophenylsulfonyl)phenyl]propanenitrile | 110% (NI) | 101% (NI) | 58% (I) |
| CB27 | N-benzyl-4-(pyridin-2-yl)thiazol-2-amine | 138% (NI) | 91% (NI) | 43% (I) |

NI-No Inhibition @ 10 micromolar conc.
I-Inhibition @ 10 micromolar conc.

Example 1 References Cited:
(1) V. Vasiliou, D. W. Nerbert, *Human Genomics* 2005, 2, 138-143.
(2) S. Harada, T. Okubo, T. Nakamura, C. Fujii, F. Nomura, S. Higuchi, M. Tsutsumi, *Alcohol Clinical and Experimental Research* 1999, 23, 958-962.
(3) H. N. Larson, J. Zhou, Z. Chen, J. S. Stamler, H. Weiner, T. D. Hurley, *J. Biol. Chem.* 2007, 282 (17), 12940-19950.
(4) Z. Chen, J. Zhang, J. S. Stamler, *PNAS* 2002, 99, 8306-8311.
(5) Z. Chen, M. W. Foster, J. Zhang, L. Mao, H. A. Rockman, T. Kawamoto, K. Kitagawa, K. I. Nakayama, D. T. Hess, J. S. Stamler, *PNAS* 2005, 102, 12159-12164.
(6) L. Yao, P. Fan, M. Arolfo, Z. Jiang, M. F. Olive, J. Zablocki, H. L. Sun, N. Chu, J. Lee, H. Y. Kim, K. Leung, J. Shryock, B. Blackburn, I. Diamond, *Nature Medicine* 2010, 16, 1024-1028.
(7) C. H. Chen, G. R. Budas, E. N. Churchill, M. H. Disatnik, T. D. Hurley, D. M. Rosen, *Science* 2008, 321, 1493-1495.
(8) E. N. Churchill, M. H. Disatnik, D. Mochly-Rosen, *Journal of Molecular and Cellular* Cardiology 2009, 46, 278-284.
(9) G. R. Budas, M. H. Disatnik, C. H. Chen, D. Mochly-Rosen, *Journal of Molecular and* Cellular Cardiology 2010, 48, 757-764.
(10) L. V. De, G. R. Rogers, D. J. Hamrock, L. N. Marekov, P. M. Steinert, J. G. Compton, N. Markova, W. B. Rizzo, *Nature Genetics* 1996, 12, 52-57.
(11) D. Valle, S. I. Goodman, D. A. Applegarth, V. E. Shih, J. M. Phang, *Journal of Clinical* Investigation 1976, 58, 598-603.
(12) M. T. Geraghty, D. Vaughn, A. J. Nicholson, W. W. Lin, G. Jimenez-Sanchez, C. Obie, M. P. Flynn, D. Valle, C. A. Hu, *Human Molecular Genetics* 1998, 7(9), 1411-1415.
(13) P. Marcato, C. A. Dean, C. A. Giacomantonio, P. W. Lee, *Cell Cycle* 2011, 10 (9), 1378-1384.
(14) J. S. Moreb, H. V. Baker, L. J. Chang, M. Amaya, M. C. Lopez, B. Ostmark, W. Chou, *Mol. Cancer* 2008, (7) 87.
(15) J. S. Moreb, *Current Stem Cell Research and Therapy* 2008, 3 (4), 237-246.
(16) L. Sreerama, N. E. Sladek, *Biochemical Pharmacology* 1993, 45(12), 2487-2505.
(17) J. S. Moreb, D. Mohuczy, B. Ostamark, J. R. Zucali, *Cancer Chemotherapy and* Pharmacology 2007, 59, 127-136.
(18) G. Muzio, M. Maggiora, E. Paiuzzi, M. Oraldi, R. A. Canuto, *Free Radical Biology and* Medicine 2012, 52(4), 735-746.
(19) A. Emadi, R. J. Jones, R. A. Brodsky, *Nat. Rev. Clin. Oncology* 2009, 6(11), 638-647.
(20) L. Sreerama, G. K. Rekha, N. E. Sládek, *Biochemical Pharmacology* 1995, 49, 669-675.
(21) L. Sreerama, N. E. Sladek, *Clinical Cancer Research* 1997, 3, 1901-1914.
(22) G. K. Rekha, L. Sreerama, N. E. Sladek, *Biochem. Pharmacol.* 1994, 48(10), 1943-1952.
(23) G. K. Rekha, V. R. Devaraj, L. Sreerama, M. J. Lee, H. T. Nagasawa, N. E. Sladek, *Biochem. Pharmcol.* 1998, 55(4), 465-474.
(24) J. S. Boesch, C. Lee, R. G. Lindahl, *J. Biol. Chem.* 1996, 271, 5150-5157.
(25) N. Lassen, J. B. Bateman, T. Estey, J. R. Kuszak, D. W. Nees, J. Piatigorsky, G. Duester, B. J. Day, J. Huang, L. M. Hines, V. Vasiliou, *J. Biol. Chem.* 2007, 282 (35), 25668-76.
(26) T. Estey, M. Cantore, P. A. Weston, J. F. Carpenter, J. M. Petrash, V. Vasiliou. *J. Biol. Chem.* 2007, 282, 4382-92.
(27) N. E. Sladek, R. Kollander, L. Sreerama, D. T. Kiang. *Cancer Chemotherapy Pharmacology* 2002, 49, 309-21
(28) L. Sreerama, N. E. Sladek, *Drug Metabolism and Disposition* 1995, 23(10), 1080-1084
(29) G. Hu, R. A. Chong, Q. Yang, Y. Wei, M. A. Blanco, F. Li, M. Reiss, J. L. Au, B. G. Haffty, Y. Kang, *Cancer Cell* 2009, 15, 9-20.
(30) M. Khanna, C. H. Chen, A. Kimble-Hill, B. Parajuli, S. Perez-Miller, S. Baskaran, J. Kim, V. Vasiliou, D. Mochly-Rosen, T. D. Hurley, *J. Biol. Chem.* 2011, 286 (50), 43486-43494.
(31) N. E. Sladek, *Current Pharm. Design* 1999, 5, 607-625.
(32) J. S. Moreb, A. Gabr, G. R. Vartikar, S. Gowda, J. R. Zucali, D. Mohuczy, *Journal of Pharm. Exp. Ther.* 2005, 312, 339-345.
(33) F. Giorgianni, P. K. Bridson, B. P. Sorrentino, J. Pohl, R. L. Blakley, *Biochem. Pharmcol.* 2000, 60 (3), 325-338.
(34) B. Parajuli, A. C. Kimble-Hill, M. Khanna, Y. Ivanova, S. Meroueh, T. D. Hurley, *Chem. Biol. Interactions* 2011, 191, 153-158.
(35) E. D. Lowe, G. Y. Gao, L. N. Johnson, W. M. Keung, W. M. *J. Med. Chem.* 2008, 51, 4482-4487.
(36) B. Parajuli, T. D. Hurley, *J. Med. Chem. (Submitted)*, 2013
(37) P. K. Hammen, A. Allali-Hassani, K. Hallenga, T. D. Hurley, H. Weiner, *Biochemistry* 2002, 41, 7156-7168.
(38) S. Perez-Miller, T. D. Hurley, *Biochemistry* 2003, 42, 7100-7109.
(39) H. Weiner, J. H. Hu, C. G. Sanny, *J. Biol. Chem.* 1976, 251 (13), 3853-3855.
(40) I. H. Segel, *Enzyme Kinetics: Behavior and Analysis of Rapid Equilibrium and Steady-State Enzyme Systems*, 1993, 100-159
(41) W. Minor, M. Cymborowski, Z. Otwinowski, M. Chruszcz, *Acta Crystallogr. D. Biol. Crystallography* 2006, 62, 859-866.
(42) P. Emsley, K. Cowtan, *Acta Crystallogr. D. Biol. Crystallography* 2004, 60, 2126-2132.
(43) S. M. Blaney, F. M. Balis, S. Berg, C. A. S. Arndt, R. Heideman, J. R. Geyer, R. Packer, P. C. Adamson, K. Jaeckle, R. Klenke, A. Aikin, R. Murphy, C. McCully, D. G. Poplack, *Journal of Clinical Oncology* 2005, 23(7), 1555-1563.

Example 1 Accession Code:

The atomic coordinates and the crystallographic structure factor of aldehyde dehydrogenase 3A1 in complex with CB29 have been deposited in the Protein Data Bank with accession code 4H80.

Example 2

Structural and Kinetic Characterization of Benzimidazole as a Selective and Potent Inhibitor of ALDH3A1

Introduction.

Aldehyde dehydrogenases (ALDH) are $NAD(P)^+$ dependent enzymes that catalyze the oxidation of aldehydes to their corresponding carboxylic acids. They are involved metabolism of endogenous as well as exogenous aldehydes thus maintaining cellular homeostasis. There are 19 functional members of the ALDH gene family known till date that are involved in variety of functions.[1] These include ethanol oxidation, production of retinoic acid, folate metabolism, GABA biosynthesis, as well as proline and branched-chain amino acid metabolism and many others.[1] Polymorphisms in ALDH gene is associated with several complications. For instance, ALDH2 polymorphisms (E487K or E504K) that is present in the East Asian population is associated with impaired ethanol metabolism[2] and reduced efficacy of nitroglycerin[3,4,5]. Modulation of ALDH2 activity can also influence cocaine addiction[6] and ischemia reperfusion injury following myocardial infarction[7,8,9]. Sjögren-Larson syndrome (SLS) is associated with an underlying genetic deficiency of ALDH3A2[10]. Mutation of ALDH4A1 is associated with type II hyperprolinemia[11,12]. ALDH family members are also implicated in cancer biology, with ALDH1A1 identified as a biomarker for cancer stem cells[13,14]. Extensive research has linked the expression of ALDH3A1 and ALDH1A1 in cancer cell proliferation and resistance to cyclophosphamide derivatives[15,16]. ALDH1A1 and ALDH3A1 expression in cancer cells render these cells resistant to cyclophosphamide by metabolizing its intermediate, aldophosphamide[15,16,17].

ALDH3A1 was originally designated as the tumor ALDH as it was found highly expressed in some human tumors such as hepatoma, lung adenocarcinoma, myeloma, breast cancer and stem cell populations[18,19,20,21,22]. It is a cytosolic enzyme involved mostly in the oxidation of peroxidic and fatty aldehydes. Even though ALDH3A1 is expressed in cornea and keratinocytes[16,23,24], studies have shown that Aldh3a1(-/-) knockout mice are viable25. High ALDH3A1 activity in normal cells protects these cells from lipid peroxidation products whereas contributes to drug resistance in tumor cells. Manipulation of ALDH activity levels, including ALDH3A1, alters the extent of resistance to cyclophosphamide derivatives. RNAi-mediated knockdown of ALDH1A1 and ALDH3A1 in the A549 lung adenocarcinoma cell line revealed that both enzymes contribute equally to the resistance against 4-hydroperoxycyclophosphamide, an analog of cyclophosphamide[15].

Previous studies in cultured human colon carcinoma cell lines have shown that the colon C cell line was 10-fold less sensitive to mafosfamide than the RCA and HCT 116b colon cancer cell lines, which express 200-fold lower levels of ALDH3A120. However, all three cell lines (Colon C, RCA and HCT 116b) were equally sensitive to phosphoramide mustard, the final activated product of cyclophosphamide metabolism that cannot be acted on by ALDH3A120. The same study showed that Colon C cancer cells were more sensitive when the exposure to mafosfamide was performed in the presence of benzaldehyde, which is a good competitive substrate for ALDH3A120. MCF-7 cells electroporated with ALDH3A1 were 16-fold less sensitive toward mafosfamide than control cells[26]. Another study showed that inhibition of human class 3 aldehyde dehydrogenase using chlorpropamide analogues in MCF-7/0/CAT cells, which express high concentration of ALDH3A1, sensitized these cells to mafosfamide[21]. More recently, a non-selective inhibitor of ALDH isoenzymes enhanced sensitivity toward mafosfamide in A549 cells[27]. However, the extent to which ALDH3A1 can contribute to resistance remains controversial[15,28].

Some antineoplastic agents induce apoptosis in cancer cells by producing oxidative stress through generation of lipid peroxidation products. ALDH3A1 can detoxify the products of lipid peroxidation and hence facilitate drug resistance. In fact, a recent study has shown that ALDH3A1 is one of the downstream targets of metadherin (MTDH), an important contributor toward multidrug chemoresistance[29]. LM2 cells engineered to express an inducible shRNA against ALDH3A1 for conditional knockdown were more sensitive to chemotherapeutic agents such as paclitaxel, doxorubicin and 4-hydroxycyclophosphamide when ALDH3A1 was knocked down. In addition, constitutive overexpression of ALDH3A1 in LM2 cells was able to partially rescue the chemoresistance to paclitaxel, doxorubicin and 4-hydroxycyclophosphamide[29]. These studies highlight the role of ALDH3A1 in a broad-spectrum of cancer chemoresistance and support the development of selective, potent small molecule inhibitors.

We reasoned that selective inhibitors of ALDH3A1 could enhance the sensitivity of chemotherapeutic agents such as cyclophosphamide as well as tease out the contributions to aldophosphamide metabolism in tumor cells. In this study, we report the detailed characterization of a highly selective inhibitor for ALDH3A1, designated CB7, previously identified through the use of chemical library screening[30]. Kinetic and crystallographic studies indicate this compound is competitive to aldehyde binding, but not NADP+ binding. CB7 had no inhibitory effect on ALDH1A1 or ALDH2 activity up to 250 µM concentration. Treatment of the lung adenocarcinoma (A549) or glioblastoma (SF767) cell lines, which express ALDH3A1, with mafosfamide in the presence of CB7 or closely related analogs enhanced the killing effects of mafosfamide, whereas treatment of normal lung cells (CCD13Lu), which do not express ALDH3A1, with mafosfamide in the presence of CB7 and its analogs did not enhance the killing effects of mafosfamide.

Materials and Methods.

Materials.

Reagents such as benzaldehyde, propionaldehyde, paranitrophenylacetate, NAD+, NADP+ and buffers were all purchased from Sigma Aldrich unless otherwise stated. PEG3350 for crystallization trial was purchased from Hampton Research.

Cell Lines.

A549, CCD13Lu and SF767 cell lines were provided by Dr. Hua Lu, Dr. Melissa L. Fishel, and Dr. Karen Pollok, respectively. A549 and CCD13Lu cells were cultured in DMEM (Cellgro, Mediatech Inc, Manassa, Va.) supplemented with 10% fetal bovine serum (FBS) (Gibco, Invitrogen Company, Grand Island, N.Y.), 100 units/ml of penicillin and 10 µg/mL of streptomycin. SF767 cell lines were cultured in IMDM (Gibco, Invitrogen Company, Grand Island, N.Y.) supplemented with 10% fetal bovine serum (FBS) (Gibco, Invitrogen Company, Grand Island, N.Y.), 100 Units/mL penicillin and 10 µg/mL streptomycin. Cell viability as assessed by tryphan blue exclusion was consistently >95%. Cells were passaged after reaching 80-90% confluence, which usually took 3-4 days for A549 and SF767 cell lines and 8-12 days for CCD13Lu cells.

Protein Expression and Activity Measurement.

Human ALDH1A1, ALDH2 and ALDH3A1 were expressed and purified as described elsewhere[31,33,44]. Human ALDH1A2, ALDH1A3 and ALDH1B1 were expressed and purified as described elsewhere[36]. The enzymatic activity of ALDH1A1, ALDH2 and ALDH3A1 were monitored by calculating the increase in absorbance at 340 nm due to NAD(P)H formation (molar extinction coefficient of 6220 M-1 cm-1) as described earlier[33,44]. The activity of ALDH1A2, ALDH1A3 and ALDH1B1 were monitored as described elsewhere[36]. The specific activities of the purified proteins were 1.9 (ALDH1A1), 0.8 (ALDH1A2), 0.44 (ALDH1A3), 0.2 (ALDH1B1), 3.8 (ALDH2) and 32 (ALDH3A1) µmole/min/mg for ALDH1A1, ALDH2 and ALDH3A1 respectively.

Inhibitors.

CB7, the most potent and selective ALDH3A1 inhibitor discovered in our initial chemical screen33, was purchased from ChemBridge Corp. This compound had three important moieties—2-methylbenzimidazole, sulfonyl and fluorophenyl groups. In our initial search, we looked for analogs that had two of these three moieties to see which moiety would contribute the most in terms of selectivity and potency. The second round of search was conducted for analogs that had all these three moieties connected the exact same way but that had small substitutions at various positions. All these analogs had at least 95% structural similarity to CB7. Over 118 compounds were purchased from ChemBridge Corp. and ENAMINE Ltd., Kiev, Ukraine, Princeton Biomolecular Research Ltd, Life Chemicals and Vitas M. Laboratories. The purity of the compounds according to the vendor was >95%. Compounds were dissolved and diluted in 100% DMSO and stored at −20° C. The analogs were tested for their selectivity against ALDH1A1, ALDH2 and ALDH3A1 at 100 μM concentration. Compounds discussed in this study with their respective vendor and corresponding catalog numbers are shown in Table 5 below:

TABLE 5

| Compounds | Vendors with catalog numbers |
|---|---|
| A3 | (Chembridge Corp.-5172826) |
| A5 | (Chembridge Corp.-5172831) |
| A6 | (Chembridge Corp.-5175600) |
| A10 | (Chembridge Corp.-5215982) |
| A13 | (Chembridge Corp.-5231103) |
| A16 | (Chembridge Corp.-5243439) |
| A20 | (Chembridge Corp.-5260321) |
| A21 | (Chembridge Corp.-5264371) |
| A22 | (Chembridge Corp.-5284379) |
| A24 | (Chembridge Corp.-5510049) |
| A30 | (Chembridge Corp.-5607189) |
| A38 | (Chembridge Corp.-5648440) |
| A39 | (Chembridge Corp.-5651872) |
| A40 | (Vitas M. Laboratories.-STK354007) |
| A47 | (Chembridge Corp.-6104618) |
| A53 | (Chembridge Corp.-6382505) |
| A62 | (Chembridge Corp.-7224032) |
| A64 | (Chembridge Corp.-7289639) |
| A67 | (Chembridge Corp.-7567094) |
| A70 | (Chembridge Corp.-7928260) |
| B27 | (Vitas M. Laboratories.-STK454495) |
| B36 | (Chemdiv Corp. 6529-0359) |
| B37 | (Chemdiv Corp. K783-5471) |
| CB7 | (Chembridge Corp.-5613645) |

Determination of Kinetic Parameters.

ALDH1A1, ALDH2 and ALDH3A1 activities were measured as described earlier[33,44,45]. IC50 values were determined for CB7 and its analogs using propionaldehyde as the substrate for ALDH1A1 and ALDH2 or benzaldehyde as the substrate for ALDH3A1 on a Beckman DU-640 spectrophotometer at concentrations of inhibitors ranging from 50 nM to 100 μM following a 1 minute pre-incubation. Reaction was initiated by the addition of the aldehyde substrate. There was no pre-incubation time-dependence to the inhibition. The inhibition curves were fit to the Logistic four parameter IC50 equation using the SigmaPlot (v11, StatSys). Steady state kinetic experiments were performed by co-varying inhibitor and substrate concentrations. The steady state kinetic measurements were performed in 100 mM Na2HPO4 buffer, pH 7.5. The reaction mixture contained 6 nM ALDH3A1, varied benzaldehyde (100 μM-800 μM under fixed NADP+, 1.5 mM) at varied inhibitor concentration (0-200 nM) or varied NADP+ (100 μM-500 μM; fixed benzaldehyde, 1 mM) at varied inhibitor concentrations (0-200 nM). All experiments including the controls contained 2% (v/v) DMSO.

The initial rate of product formation was determined on a Beckman DU-640. All data were fit to the non-linear velocity expressions for competitive, non-competitive, mixed-type non-competitive and uncompetitive inhibition[46]. Appropriateness of the inhibition model was determined through analysis of goodness-of-fit and the residuals of those fits. Lineweaver-Burke plots were created using SigmaPlot (v11, StatSys) to visualize the inhibition patterns. All data represent the average of three independent experiments utilizing triplicate assays at each concentration point.

Crystallization of ALDH3A1 with NAD+ and CB7.

ALDH3A1 crystals were grown from solutions containing 0.2 M potassium acetate, 20% PEG 3350 at 25° C. The enzyme concentration was 4 mg/mL in 10 mM HEPES buffer, pH 7.5. The enzyme was mixed with 1 mM NAD+ and 1 mM CB7. Sitting drop experiment was performed with 8 μL drop size and 1000 μLs of mother liquor. Crystals were obtained in about a week. These crystals were frozen directly in gaseous nitrogen stream at 100K without additional cryoprotectant.

Datasets were collected at a wavelength of 0.9869 Å at 100 K at the Advanced Photon Source using the GM/CA-CAT beamline 23-ID located at Argonne National Laboratory. The diffraction data was indexed, integrated and scaled using the HKL3000 program[47]. All refinements were performed using the program package Refmac5 as implemented in the CCP4 program suite[47] and model inspection and building was accomplished using Coot[48]. All these structures were solved by performing molecular replacement using the apo-form of ALDH3A1 structure as the search model (RCSB code 3SZA). Molecular replacement was performed using MolRep program provided by CCP4 Interface software. Initial maps showed clear electron density for the CB7 bound on the active site of two out of four monomers present in the one unit cell. The two other subunits had partial occupancy of CB7 in its active site. Ligands were included in later stages of refinement. Water molecules were added after the addition of ligands in order to obtain an unbiased map for ligands. Ligand maps were sketched in Sketcher (provided by CCP4). This structure was used to create library description file, which were later used for refinement. Two independent dimers of ALDH3A1 comprise one asymmetric unit.

Generation of Q122A and Q122W Mutants.

In order to characterize the binding pattern of CB7 to catalytic site of ALDH3A1, two important mutations Q122A and Q122W were made. oint mutations of ALDH3A1 were performed using QuickChange (Qiagen) mutagenesis. LDH3A1 mutants were constructed using forward primer 5'-CTT CAA CCT CAC CAT CGC GCC CAT GGT GGG CGCC-3' (SEQ ID NO:1) for Q122A and forward primer 5'-CCT TCA ACC TCA CCA TCT GGC CCA TGG TGG GCG CCA TC-3' (SEQ ID NO:2) and complement for Q122W mutant. These two mutant proteins were purified exactly the same way as was ALDH3A1. However, the yield was significantly decreased as compared to WT protein. Q122A was stored at 0.9 mg/ml concentration and Q122W was stored at 0.4 mg/ml concentration at −80° C. Kinetic experiments were performed exactly the same way as the wild type (WT) enzyme.

Analysis of ALDH3A1 Catalyzed Dehydrogenase Activities from Cell Lysates.

Cell lysates were obtained from A549, SF767 and CCD13Lu cell lines. In summary, cells (A549, SF767 and CCD13Lu) were washed with ice cold PBS to remove residual media. 400 μL of RIPA buffer (Cell signaling technologies) containing 1 mM PMSF (Sigma Aldrich) was added to each 10 cm dish. Plates were incubated on ice for 5 minutes, scraped and lysates were collected. Lysates were centrifuged for 10 minutes at 16,000×G in a micro-centrifuge at 4° C. Protein concentrations were measured using the Bradford reagent (Biorad Laboratories). 50 μg of cell lysate was used in the activity assay. ALDH3A1 activity in cell lysates were measured in 100 mM Na2HPO4 buffer at pH 7.5, with 1.5 mM NADP+ and 1 mM benzaldehyde. Activity assay was also performed with 1 μg of recombinant ALDH3A1 in the presence and absence of CB7 and its analogs A10, A20, A21, B27, A64, A70 and B37. All assays, including the controls, contained 1% (v/v) DMSO. These compounds were tested at 10 μM concentration to monitor the extent of ALDH inhibition in these cell lysates and purified ALDH3A1. Lysates were treated with these compounds for 1 minute before the substrate was added.

Mafosfamide Sensitivity Experiments.

MTT assay was used for conducting mafosfamide chemosensitivity experiments.

Mafosfamide was used for this study primarily because it is an analog of cyclophosphamide and it does not require cytochrome P450 for its activation which is ideal for cell based studies[49]. Three cell lines, A549, SF767 and CCD13Lu were chosen for this study. These cell lines were chosen because A549 express both ALDH1A1 and ALDH3A115, SF767 express only ALDH3A1, whereas CCD13Lu express neither of these enzymes[36]. CCD13Lu was also relevant for this study because it is normal lung cell line which serves as a proper control for A549, which is a carcinogenic cell line from lung.

Our standardization measurements showed that 5000 cells/well is optimal for A549 and CCD13Lu and 10,000 cells/well is optimal for the SF767 cell line for a linear response of MTT assay. Approximate ED50 values for adenocarcinoma (A549), glioblastoma (SF767) and CCD13Lu cell lines were 125 μM, 150 μM and 40 μM respectively[36]. After optimization experiments, A549 (5,000 cells/well), SF767 (10,000 cells/well) and CCD13Lu (5,000 cells/well) were seeded in 96 well plates. 29 hours later, A549, SF767 and CCD13Lu cells were treated with 10 μM ALDH3A1 inhibitors (A10, A20, A21, A64, A70, B27, B37 and CB7) in the absence or in the presence of mafosfamide corresponding to their ED50 values. These compounds were chosen for chemosensitivity experiments because they showed highest potency and selectivity in our SAR experiments and were closely related to each other. The MTT assay was performed 19 hours after compound treatment to access the cell proliferation[31].

The relative percentage of cell proliferation was calculated in comparison to DMSO (0.25%) treated controls. DMSO concentration was strictly limited to 0.25% for these experiments, which had no significant effect on cell viability by itself (data not shown). The time points for treatment were chosen based on similar experiments performed earlier[31].

Results.

CB7 is a Very Potent and Selective ALDH3A1 Inhibitor that Competes with Aldehyde Binding.

Figure 9:
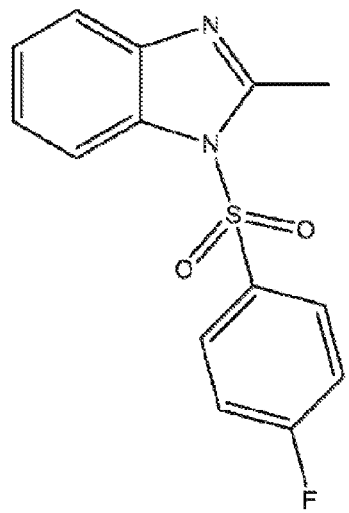
FIG. 9. Chemical structure of CB7 and corresponding IC50 plot for CB7 on ALDH3A1 catalyzed dehydrogenase activity.
Figure 9:
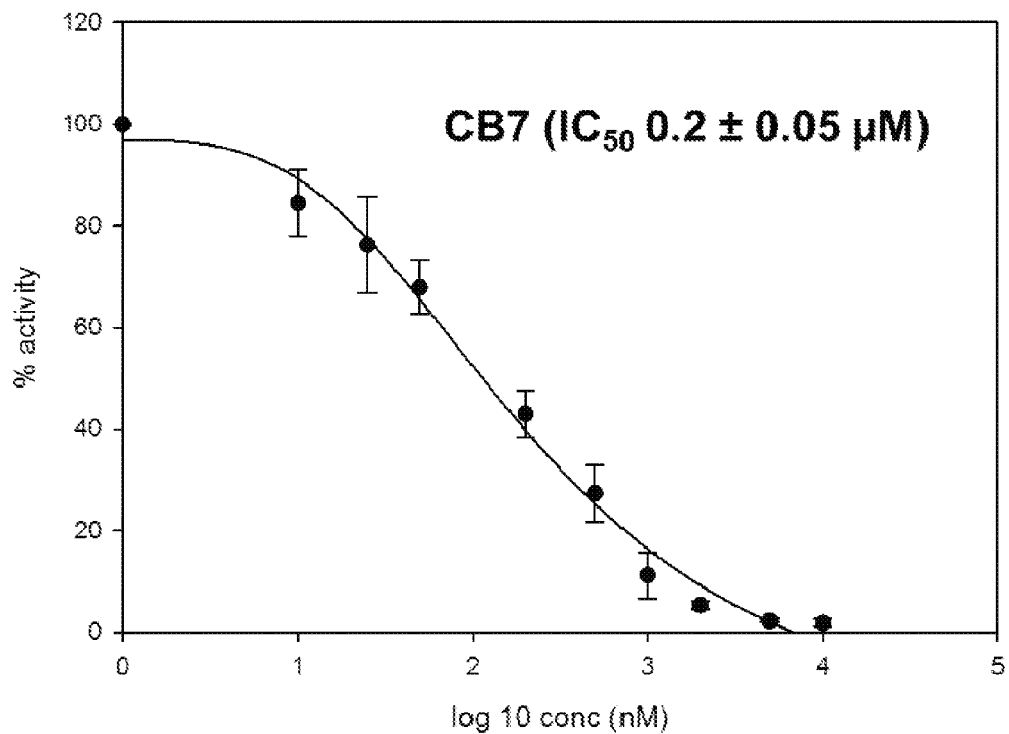
Figure 10A:
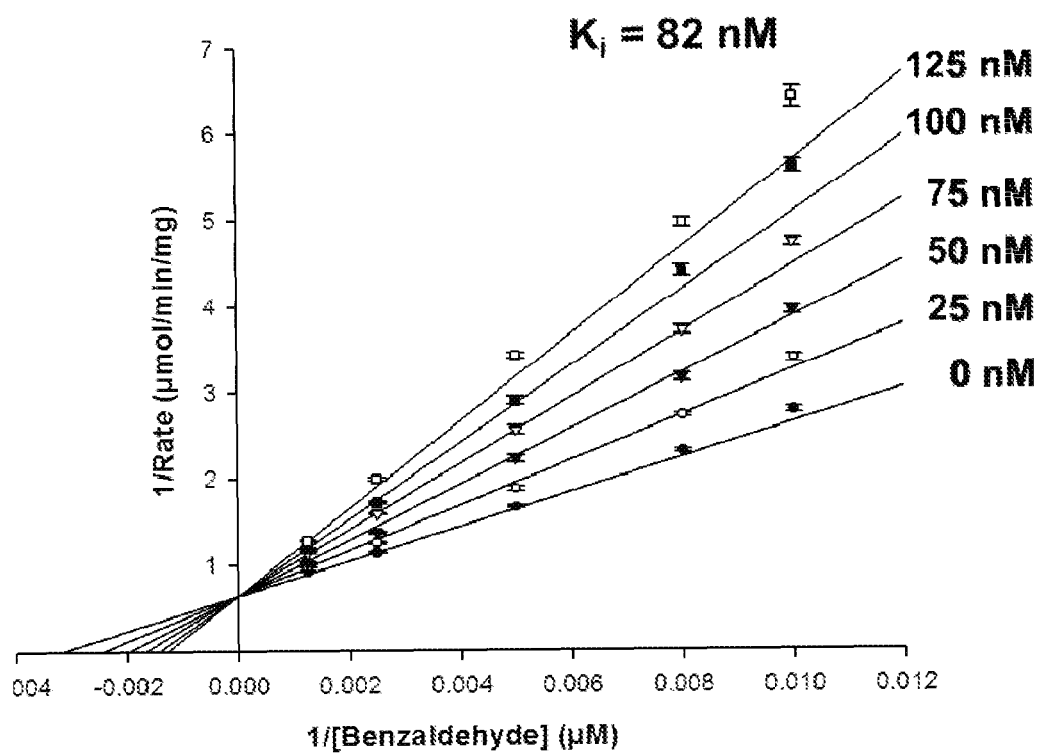
FIG. 10A. Steady state kinetics for determining the mode of inhibition of CB7. Competitive mode of inhibition shown by CB7 towards benzaldehyde. Initial velocities were measured using 10 nM ALDH3A1 and 1.5 mM NADP+ by co-varying benzaldehyde (100-1000 µM) and various CB7 concentrations (0-125 nM). The inset shows 1/v vs. 1/[benzaldehyde] for 0 nM –125 nM CB7 showing intersection at 1/Vmax.
Figure 10B:
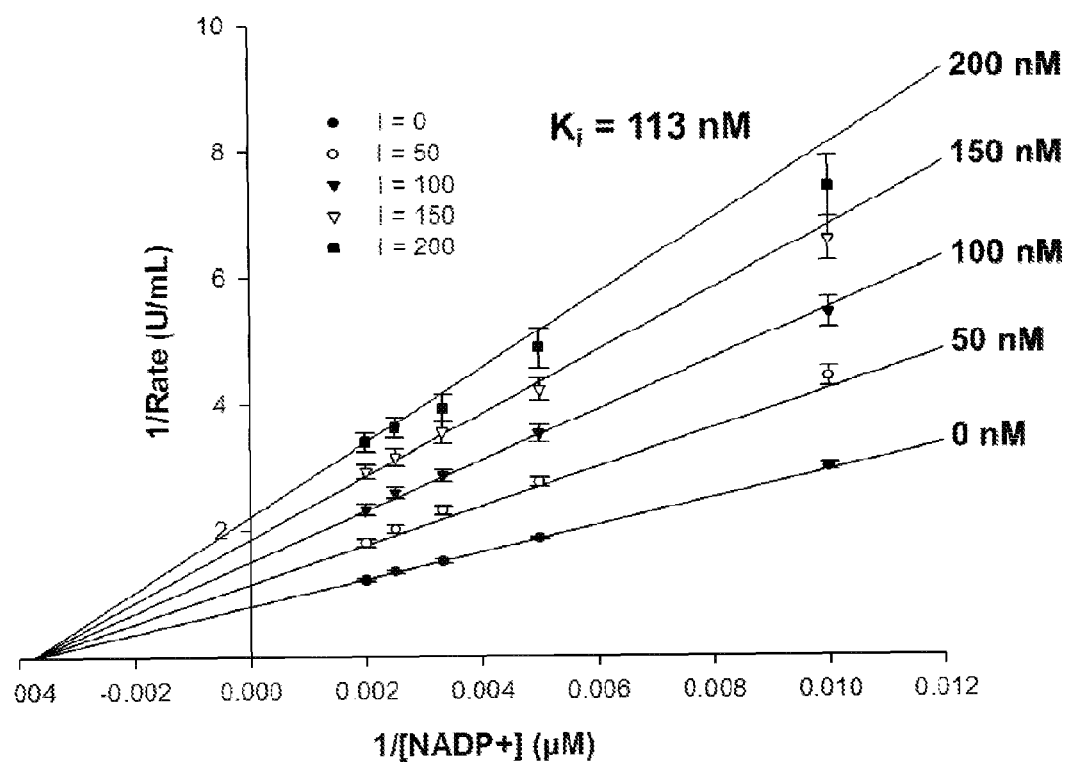
FIG. 10B. Non-competitive mode of inhibition was shown by CB7 towards benzaldehyde. Initial velocities were measured using 10 nM ALDH3A1 and 1 mM benzaldehyde by co-varying NADP+ (100 µM-500 µM) and various CB7 concentrations (0-200 nM). All experiments were done in triplicates and one representative experiment out of three is depicted.
Figure 10C:
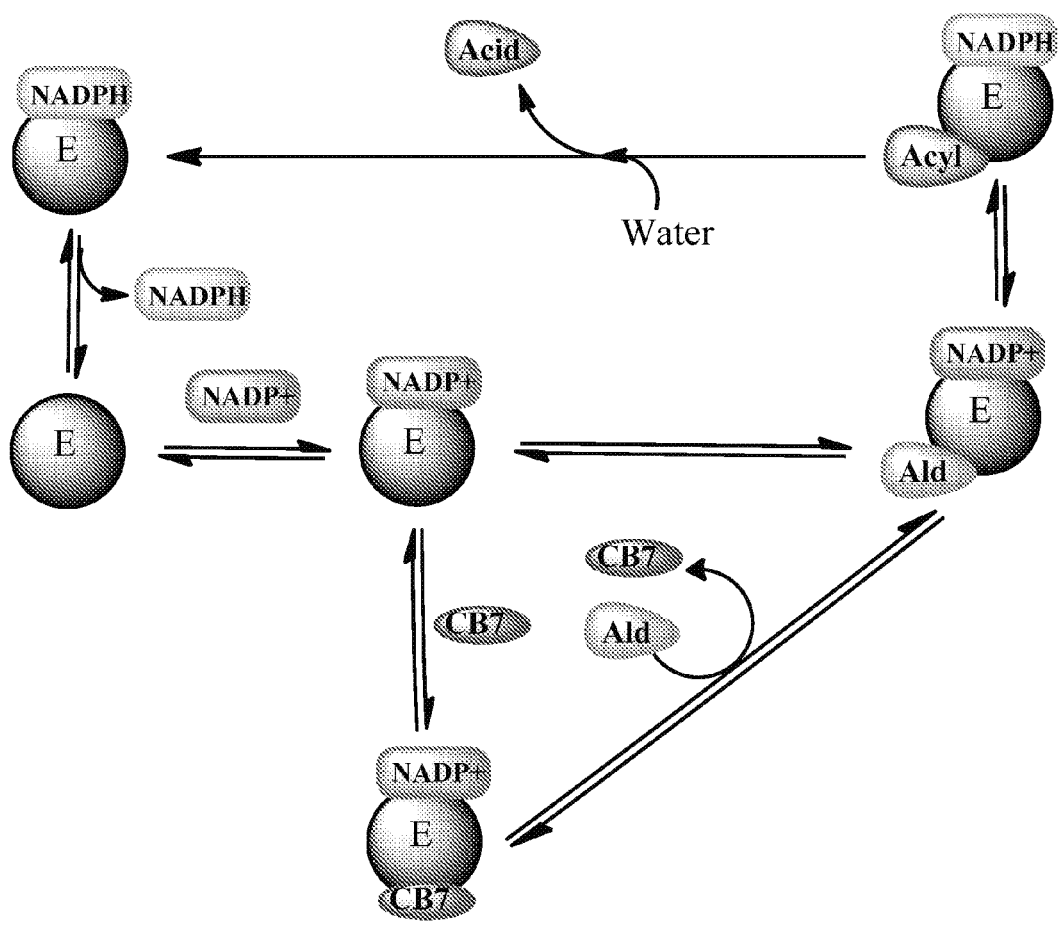
FIG. 10C. Figure showing the catalytic mechanism of how CB7 inhibits ALDH3A1. Reaction initiates with NADP+ binding into the rossman fold subsequently followed by the binding of benzaldehyde. This is followed by thiohemiacetal formation, hydride transfer, hydrolysis and carboxylic acid formation. CB7 competes with aldehyde binding showing no effect on NADP+ binding.

We performed a high throughput screen and reported CB7 as a selective inhibitor of ALDH3A130. The chemical name for this small molecule is 1-[(4-fluorophenyl)sulfonyl]-2-methyl-1H-benzimidazole (FIG. 9, top panel). CB7 has a molecule mass of 290 Daltons and has no structural similarity to any known inhibitors of aldehyde dehydrogenase isoenzymes. The compound has very high potency (IC50 of 0.2±0.05 μM) for an initial hit compound against ALDH3A1 (FIG. 9; bottom panel) and good selectivity toward ALDH3A1, demonstrating no inhibition toward ALDH1A1 or ALDH2 activity at 250 μM concentration. Steady-state kinetic experiments showed that CB7 exhibits a competitive mode of inhibition with respect to benzaldehyde, with a Ki of 82±6 nM and a non-competitive mode of inhibition with respect to NADP+, with a Ki of 113±3 nM (FIGS. 10(a), 10(b) and 10(c)).

Structure Activity Relationship of CB7 Derivatives on ALDH3A1.

We evaluated 118 different structurally related analogs of CB7 with at least 95% structural similarity for their inhibitor potency toward ALDH3A1 and selectivity versus ALDH1A1 and ALDH2 using dehydrogenase assay. Substitutions were made at several different positions. Representative compounds with their selectivity and potency pattern in respective enzymes are shown in Table 6. We initially looked at the contribution of methyl group at R1 position to see if any other substitutions in this region would make this compound more potent. Our SAR study showed that methyl substitution at R1 position is optimal (compare A20 with A21 and A10 with A3). However, aromatic or bigger substitutions were not tolerated (compare A6 and A13 with A20, A21, B36 and B37). These two compounds had no inhibition on ALDH3A1 activity.

Next, compounds having modification in R2 and R3 position were tested for their selectivity and potency. Our study showed that compounds having even a methyl substitution at R2 or R3 position showed no inhibition on ALDH3A1 activity (compare A24 with A38 and A47). We concluded that there is not much modification that could be made at this region to make this compound more potent. One interesting feature of CB7 is the presence of fluorine atom at R6 position. Therefore, we looked at analogs with different charges and sizes at R6 position. Analogs with hydrogen, methyl, isobutyl, acetamide substitution at this position do not inhibit ALDH3A1 whereas fluorine or chlorine substitution was able to inhibit ALDH3A1 (compare A5, A3, A16 and A67 with A21 and A24). Since chlorine and fluorine both are strong electron withdrawing atoms, we believe that these two atoms deactivate and stabilize the benzene ring associated with it and contribute for hydrophobic interactions with the surrounding residues whereas acetamide group being electron donating destabilizes the benzene ring (compare A20 with A22).

Next, we looked at compounds with substitution at either R4 or R8 position. Compounds with methoxy or halogen substitution at these two positions were not inhibitory to ALDH3A1 activity (compare A30 with A20, A39 with A24 and A40 with CB7). Substitutions at either R5 or R7 were not greatly deleterious, but still showed some drop in their inhibitory potency (compare A53 and A64 with A20 and A70 with CB7). Since all the analogs we tested had higher IC50 value than the CB7, we concluded that CB7 possess optimal potency by itself.

ALDH3A1 Crystal Structure with CB7.

Figure 11A:
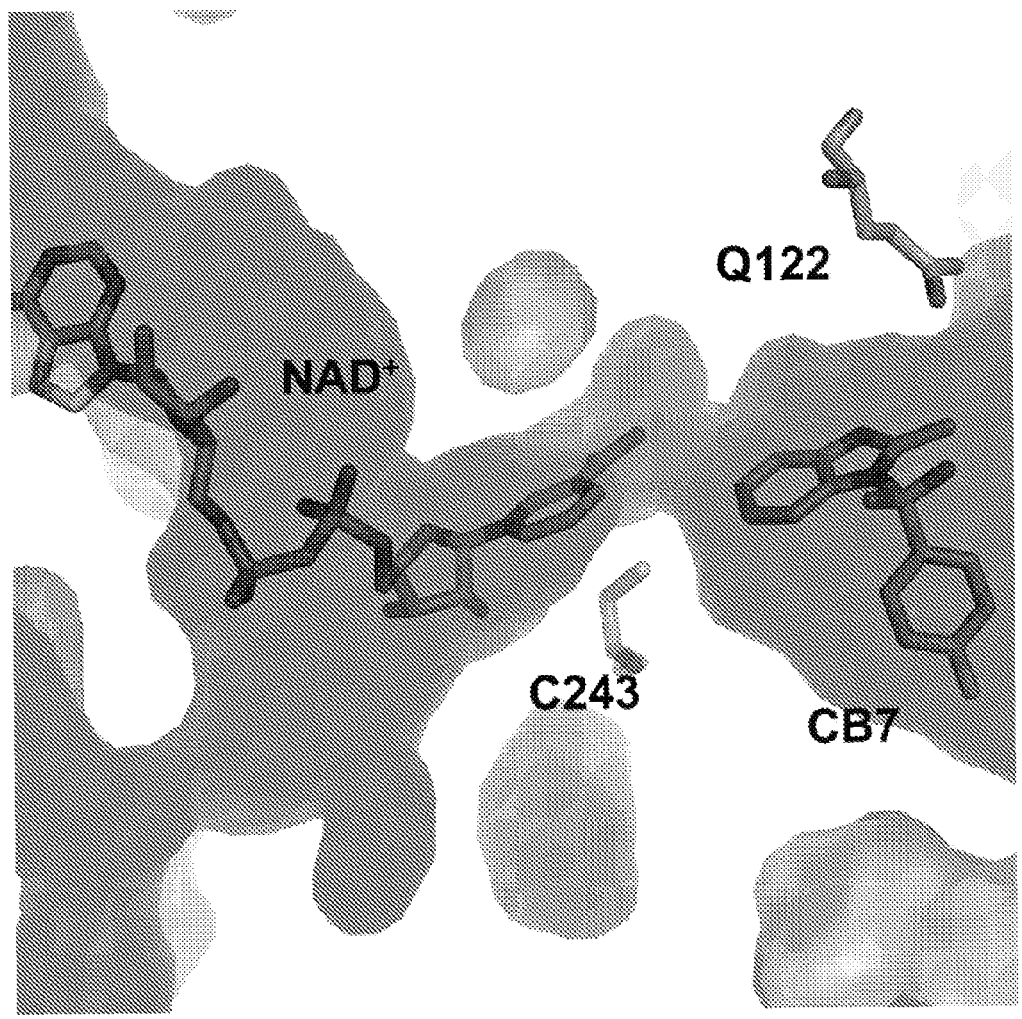
FIG. 11A. Structure of human ALDH3A1 bound to CB7 in the presence of NAD+. Surface representation of catalytic and NAD(P)+ binding site of ALDH3A1. NAD+ is bound on one pocket followed by binding of CB7 into the catalytic pocket. Bound ligands are represented as sticks.
Figure 11B:
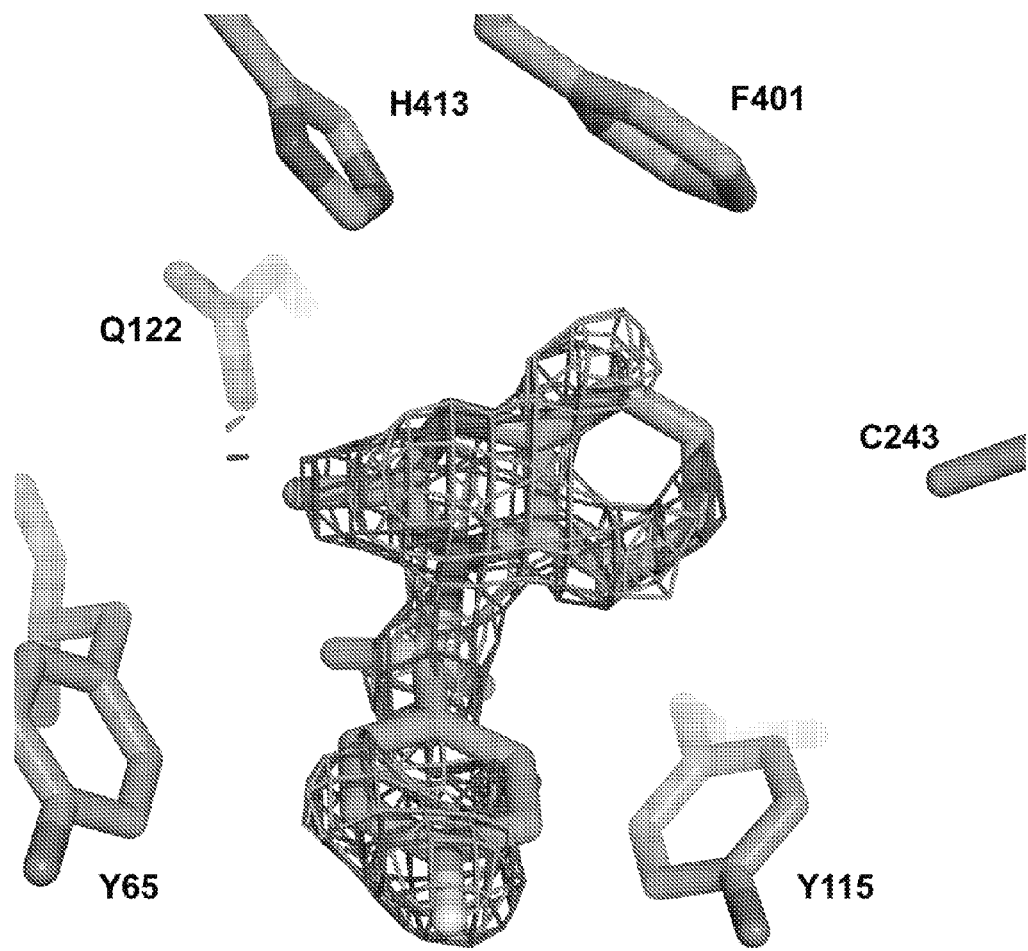
FIG. 11B. The active site of ALDH3A1. The electron density maps displayed are the original figure of merit (σ-A weighted) Fo-Fc map contoured at 2.5 standard deviations (green) and the original figure-of-merit weighted 2Fo-Fc map contoured at 1 standard deviation (blue) superimposed on the final refined model of CB7 bound in the enzyme active site. Residues that contribute to hydrophobic interactions within a distance of 3.4-4.0 Å are represented as sticks.
Figure 11C:
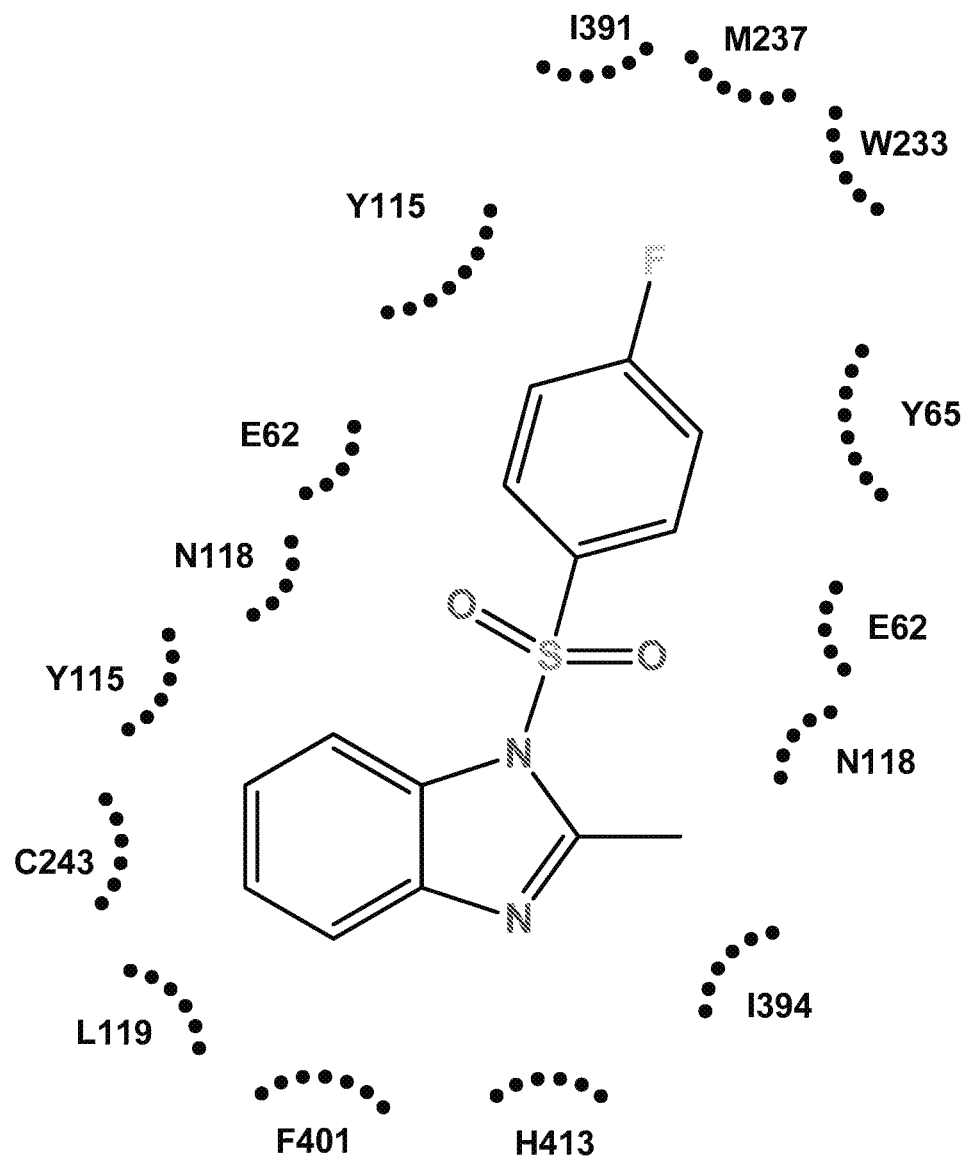
FIG. 11C. Two dimensional representation of the hydrophobic contacts seen between CB7 and residues within the active site of ALDH3A1.

In order to further validate and support our kinetic results as well as to understand the structural basis of inhibition, we wanted to get the crystal structure of CB7 bound to ALDH3A1. CB7 was chosen among all of these compounds because it was the most potent compound (Ki=0.1 μM) among all the analogs tested, exhibited very good solubility, and shared >95% structural similarity to all the other analogs. The presence of CB7 within the active site of ALDH3A1 was confirmed through examination of the original figure-of-merit, σA-weighted, electron density maps (FIG. 11(b)). There are four subunits in one asymmetric unit arranged as two independent dimers. The active site of each subunit is occupied by CB7 (FIG. 11(b)). Detailed refinement statistics are provided in Table 7. In the Ramachandran plot, 97.3% of all residues are in the most favored regions. Interestingly, no hydrogen bonding interaction was observed between CB7 and ALDH3A1. However, we observed a lot of hydrophobic interaction between CB7 and ALDH3A1 (FIG. 11c). Benzene ring from benzimidazole forms hydrophobic contact with Phe401, Tyr115, Leu119 and Cys243. The imidazole ring forms a strong hydrophobic interaction with His 413 and Ile 394. The methyl group associated with imidazole ring forms hydrophobic interaction with Tyr65 and Ile394. One of the sulfonyl oxygen forms hydrophobic interactions with Tyr65, Glu62 and Asn118. The other sulfonyl oxygen forms hydrophobic interactions with Tyr115, Glu62 and Asn118. Benzene ring attached to fluorine forms hydrophobic interaction with two tyrosine residues, Tyr65 and Tyr115 as well as with Thr395 and Glu61. The sulfonyl and attached fluorobenzene subgroup lies symmetrically right in between Tyr115 and Tyr65, creating almost an equivalent hydrophobic interaction between two Tyrosine residues (Tyr65 and Tyr115). Hydrophobic contacts are also seen between fluorine and Ile391, Trp233 and Met237 (FIG. 11c).

Characterization of Q122A and Q122W mutants.

Figure 11D:
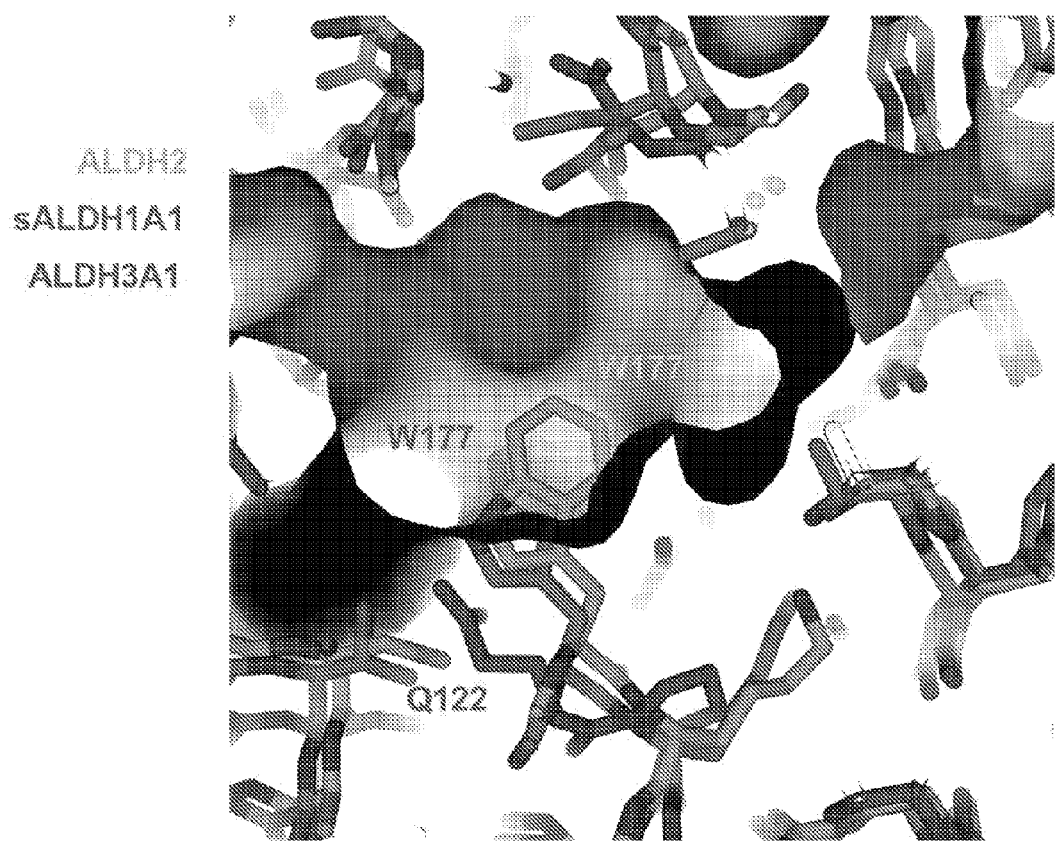
FIG. 11D. Figure showing the structural alignment of sALDH1A1, ALDH2 and ALDH3A1 to compare the important catalytic residues. Catalytic surface of ALDH3A1 is shown in pink color. ALDH1A1, ALDH2 and ALDH3A1 are represented is sky blue, yellow and pink color respectively. Figure shows that ALDH3A1 has a glutamine at 122 position instead of tryptophan, which is present in ALDH2 and sALDH1A1.

We compared the crystal structure of human ALDH3A1 against two other closely related isozymes human ALDH2 and ALDH1A1 from sheep (FIG. 11d) to compare their active site. Upon structural alignment, we found out one important residue, tryptophan that is present in both ALDH1A1 and ALDH2 active site, but not in ALDH3A1. In ALDH3A1 active site, glutamine residue is present in the position corresponding to tryptophan. In order to investigate how much contribution glutamine makes in CB7 binding, we decided to mutate glutamine to either alanine or tryptophan. Kinetic parameters (Kcat, Km, Kcat/Km) were determined for benzaldehyde and propionaldehyde oxidation for mutants and wild type ALDH3A1 (Table 3). Ki was further determined for CB7 against Q122A, Q122W and wild type ALDH3A1 as well (Table 8).

Results showed that alanine mutation did not show drastic effect on enzyme's turnover rate of benzaldehyde (4.91 μM-1 min-1 for wild type ALDH3A1 and 3.2 μM-1 min-1 for Q122A mutant) and propionaldehyde (0.05 μM-1 min-1 for wild type ALDH3A1 and 0.049 μM-1 min-1 for Q122A mutant). The Ki value for CB7 binding was also unchanged (Ki=0.2 μM for WT enzyme and Q122A). However, when glutamine was mutated to tryptophan, CB7 was not inhibitory at all to ALDH3A1 activity up to 250 μM concentration. The turnover rate of benzaldehyde only dropped to approximately 1/3rd (1.7 μM-1 min-1) of the rate of wild type enzyme, whereas that for propionaldehyde dropped to 4/5th (0.039 μM-1 min-1) of the rate of wild type enzyme. This data clearly supported the idea that glutamine was the major amino acid that was responsible for imparting selectivity to CB7.

CB7 and its Analogs Show Inhibition of Dehydrogenase Activity in Cell Lysates.

Figure 12A:
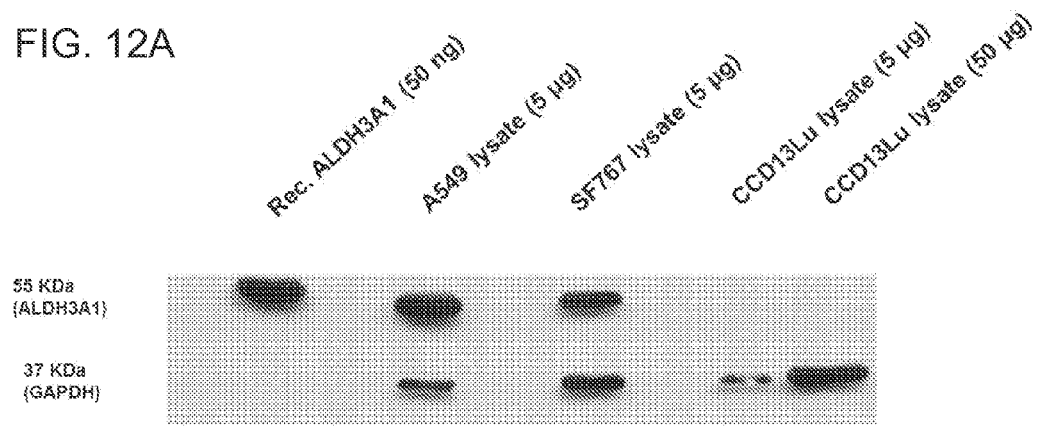
FIG. 12A. Expression and activity of ALDH3A1 and ALDH1A1 in various cell lysates. Lysates from various cancer cell lines (A549, SF767 and CCD13Lu) were examined for ALDH3A1 expression.
Figure 12B:
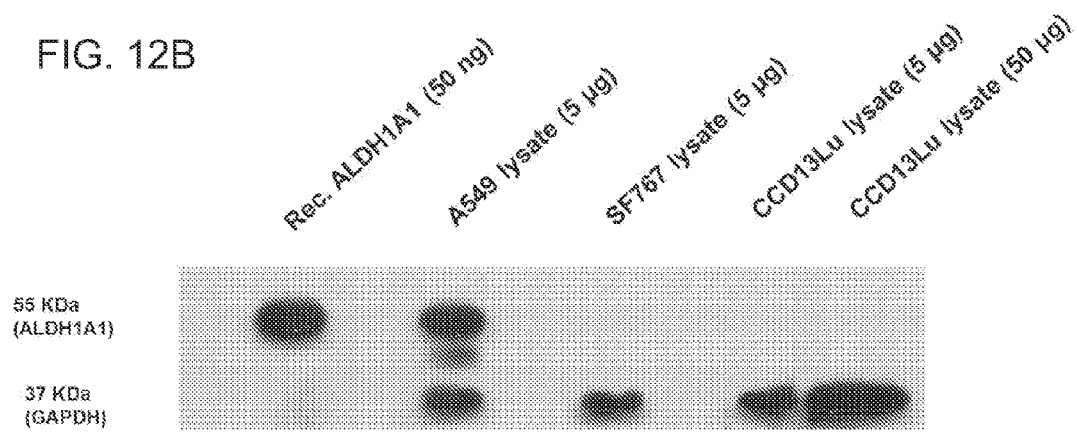
FIG. 12B. Expression and activity of ALDH3A1 and ALDH1A1 in various cell lysates. Lysates from various cancer cell lines (A549, SF767 and CCD13Lu) were examined for ALDH1A1 expression. Recombinantly purified ALDH1A1 and ALDH3A1 were taken as positive control and GAPDH as loading control.
Figure 15:
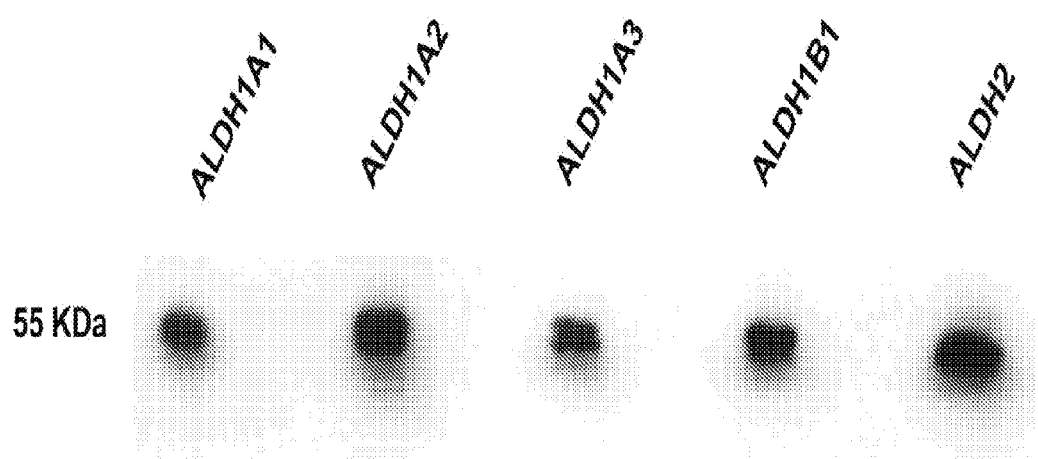
FIG. 15. Cross-Reactivity of ALDH1A1 antibody with ALDH1A2, ALDH1A3, ALDH1B1 and ALDH2. Immunoblotting of purified ALDH1A1, ALDH1A2, ALDH1A3, ALDH1B1, and ALDH2 and probing with an ALDH1A1 antibody shows that this antibody cross-reacts with all of these ALDH protein isoforms.

Lysates from series of cell lines were analyzed for the level of ALDH3A1 and ALDH1A1 protein expression, since these two enzymes are known to contribute to cyclophosphamide metabolism. Three cell lines were chosen as representatives of transformed and non-transformed cells with differential ALDH isozymes expression: A549, SF767 and CCD13Lu. Our western blot analysis confirmed that the A549 cell line (lung adenocarcinoma) expresses both ALDH1A1 and ALDH3A1 (FIGS. 12a and 12b). The SF767 cell line (glioblastoma) expresses only ALDH3A1 (FIGS. 12a and 12b), and the normal lung cell line (CCD13Lu) showed no detectable expression of either ALDH3A1 or ALDH1A1 (FIGS. 12a and 12b)[36]. In fact, as the antibody chosen for the ALDH1A1 western blot cross reacts with ALDH1A2, ALDH1A3, ALDH1B1 and ALDH2 (FIG. 15), this cell line appears devoid of most Class 1 and Class 2 ALDH expression. The normal lung cell line (CCD13Lu) also provides a reasonable control cell line for A549 cells, as both cell lines are derived from lung cells.

Figure 12C:
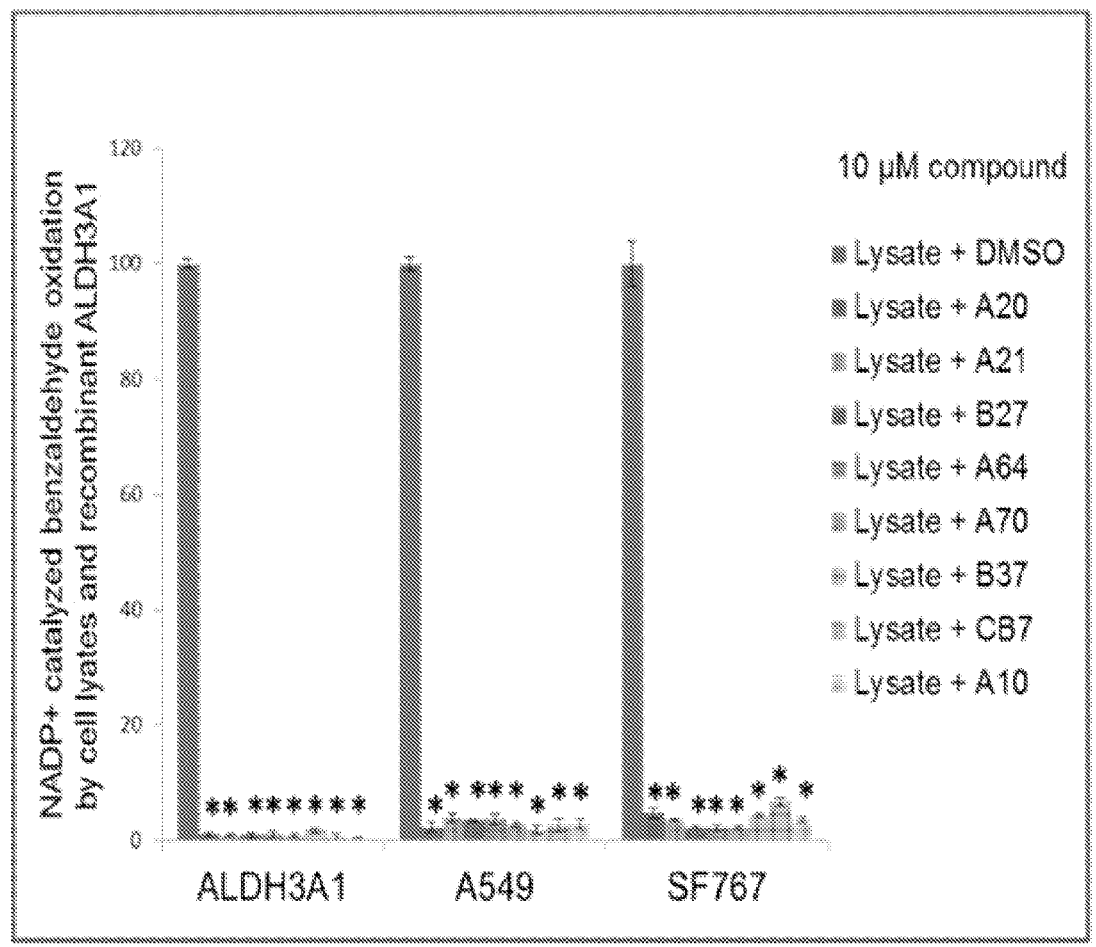
FIG. 12C. A549, SF767 and CCD13Lu cell lysate activity were tested in the presence of 1.5 mM NADP+ and 1 mM Benzaldehyde and in the presence and absence of 10 µM CB7 and its analogs. The p values were calculated using the Student's t test comparing activity in the absence and presence of inhibitor (*, p<0.0001, n=3)

To examine the ability of CB7 and selected analogs to function in a complex milieu, we tested their ability to target ALDH activity in cell lysates using benzaldehyde and NADP$^+$ as ALDH3A1 selective substrates. Benzaldehyde is a substrate for both ALDH1A1 and ALDH3A1, but ALDH1A1 does not use NADP$^+$ as a coenzyme, thus, this assay measures primarily ALDH3A1 activity. Consistent with our immunoblot experiments, A549 and SF767 showed robust benzaldehyde oxidation activity (FIG. 12c). Enzyme activity assays on A549 cell lysates using NADP and benzaldehyde had an activity of 282 nmol/min/mg. Based on the specific activity of recombinantly ALDH3A1 purified in our lab (32 μmol/min/mg), the activity assay confirmed the immunoblot and demonstrated that ALDH3A1 is active and present at ~1% of total lysate protein. Similarly, in SF767 cells, western blot analysis and enzyme assays show that ALDH3A1 is expressed at 1% of total cellular protein while the CCD13Lu cell line had an activity of <2 nmol/min/mg, which was hardly detectable. Presence of CB7 and selected analogs at 10 μM decreased the activity for A549 by >97% and SF767 by >93% cell lysates (FIG. 12C). Activity of recombinant ALDH3A1 also decreased by more than 98% in the presence of 10 μM concentration of CB7 and its analogs (FIG. 12C). These data suggest that CB7 and its analogs can target ALDH3A1 activity in the context of cellular lysates with potencies similar to those observed in purified enzyme preparations.

Sensitization of Tumor Cells to Mafosfamide Through Inhibition of ALDH3A1.

Figure 13A:
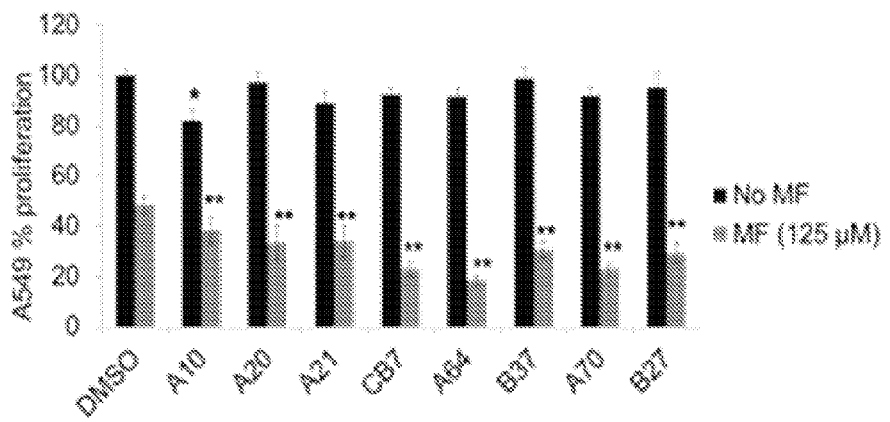
FIG. 13A. CB7 and CB7 analogs Enhance Sensitivity of ALD3H3A1-Expressing Cell Lines to Mafosfamide. A549 (5,000 cells/well)
Figure 13B:
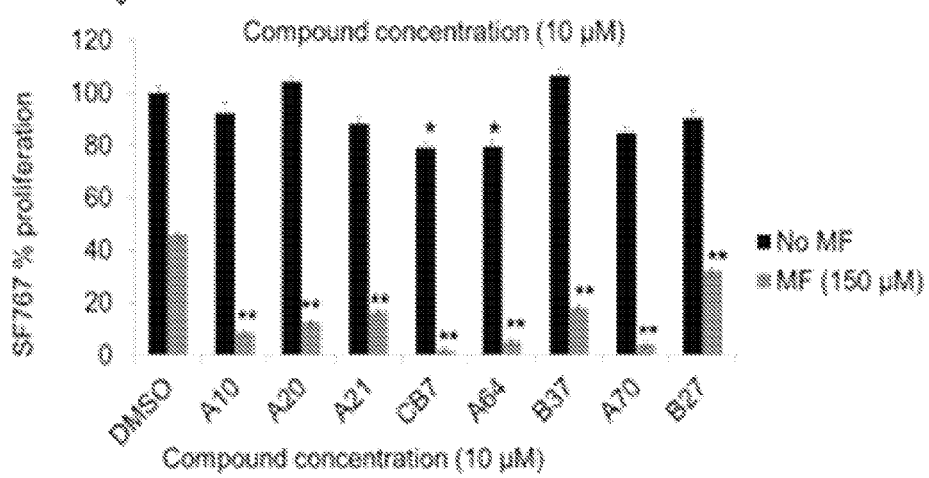
FIG. 13B. CB7 and CB7 analogs Enhance Sensitivity of ALD3H3A1-Expressing Cell Lines to Mafosfamide. SF767 (10,000 cells/well)

Prior work had demonstrated that the level of ALDH activity in tumor cells is correlated with the level of resistance toward cyclophosphamide and its derivatives[23, 24, 26, 27]. However, the extent to which ALDH3A1 contributes to this resistance has been the subject of some debate[15, 22, 24, 37, 38, 39], even though RNA knockdown of both ALDH1A1 and ALDH3A1 was required for maximal sensitization of A549 cells toward aldophosphamide[15]. Since our new ALDH3A1 inhibitors demonstrated both good potency and selectivity, we initiated studies designed to test whether inhibition of ALDH3A1 alone could sensitize cells toward cyclophosphamide derivative. For these studies, we used mafosfamide, since this compound spontaneously generates aldophosphamide in solution without the need for P450 activation. Treatment of A549, CCD13Lu and SF767 cells with mafosfamide decreased cell proliferation of all three cell lines [FIGS. 13a, 13b and 13c, DMSO control vs. mafosfamide, 100% vs. 48±3% (A549), P<0.0001; 100% vs. 46±2% (SF767), p<0.0001; 100% vs. 56±3% (CCD13Lu), p<0.0001].

Except for an analog A10, treatment of A549 cells with CB7 analogs alone at 10 μM concentration had no significant effect on cell proliferation. However, when A549 cells were treated with mafosfamide in the presence of 10 μM compound, we observed decreased cell proliferation. A549 cells showed the lowest levels of cellular proliferation with analogs CB7, A64 and A70 [FIG. 7a, MFM (0.25% DMSO) vs. MFM+Inhibitor (0.25% DMSO); 48±3% vs. 21±2% (CB7), P<0.005; 48±3% vs. 18±1% (A64), P<0.005; 48±3% vs. 20±2% (A70), P<0.005)]. Similar experiments on SF767 cells showed significantly increased chemosensitivity with analogs A10, A20, A21, CB7, A64, A70 and B37. Analogs CB7, A64 and A70 were the most potent analogs in both A549 cells and in SF767 cells, suggesting a common mechanism of action. Although we see some effect on SF767 cells by CB7 and A64 as single agents [FIG. 13b, DMSO (0.25%) vs. Inhibitor (0.25% DMSO); 100±3% vs. 80±3% (CB7), P<0.05; 100±3% vs. 82±3% (A64), P<0.05], in chemosensitivity experiments the effects of these compounds along with mafosfamide were much higher [FIG. 13b, MFM (0.25%

Figure 13C:
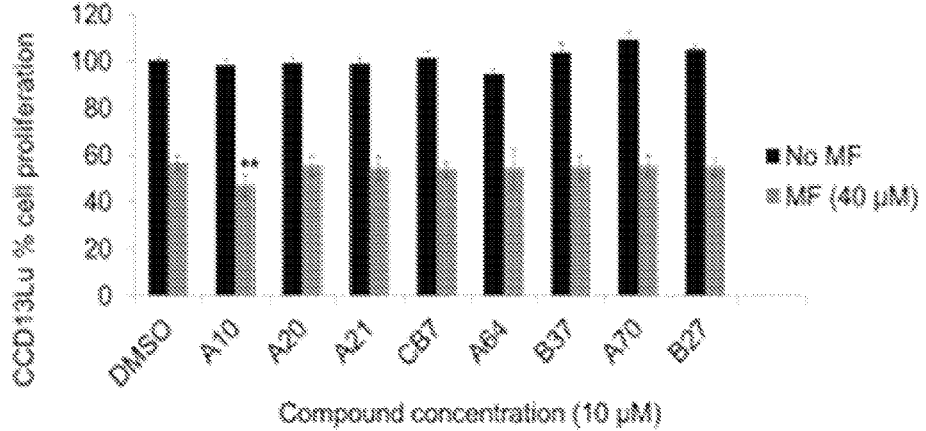
FIG. 13C. CB7 and CB7 analogs Enhance Sensitivity of ALD3H3A1-Expressing Cell Lines to Mafosfamide. CCD13Lu (5,000 cells/well) cells were plated in 96 well plates. Cells were treated with mafosfamide concentration that corresponded to their approximate $ED_{50}$ values 29 hours after cell plating. Treatment was done in the presence and absence of 10 µM inhibitors of ALDH3A1. 19 hours after treatment, cell proliferation was determined using MTT assay. The DMSO concentration was limited to 0.25% (v/v). P values were calculated by comparing the cellular proliferation of DMSO treated cells versus inhibitor treated cells (*, p<0.05, n=15) or mafosfamide (MFM) treated cells versus (MFM+10 µM Inhibitor) treated cells (**, p<0.005, n=15). Black bars represent compound treatment alone and grey bars represent compound and mafosfamide treatment. Each bar represents the mean value with standard error.

DMSO) vs. MFM+Inhibitor (0.25% DMSO); 46±2% vs. 2±1% (CB7), P<0.005; 46±2% vs. 6±1% (A64), P<0.005; 46±2% vs. 3±1% (A70), P<0.005)]. This effect was also cell line specific, since we did not see this pattern in A549 and CCD13Lu cells. In the case of CCD13Lu cells, increased chemosensitization was not observed with CB7 analogs. However, analog A10 decreased cell proliferation when these cells were treated with 10 μM compound along with mafosfamide (FIG. 13c). The SF767 cells were more sensitive to mafosfamide as measured by cell proliferation when treated with ALDH3A1 inhibitors than were A549 cells (Compare FIGS. 13a and 13b), which is consistent with more than one active ALDH isozyme present in A549 cells.

Figure 14A:
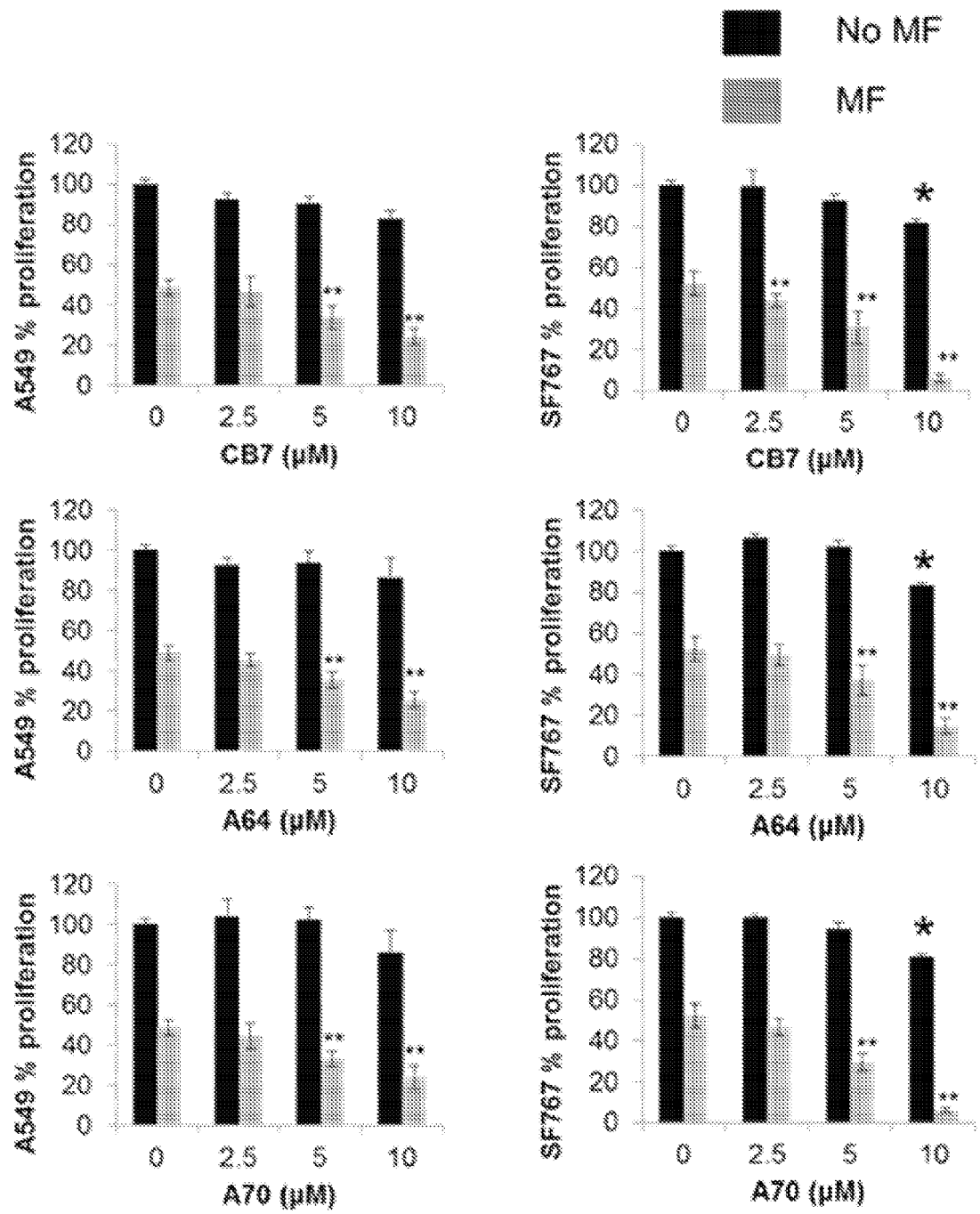
FIG. 14A. Dose-Response Effect of CB7 and CB7 analogs on Proliferation of ALDH3A1-Expressing Cell Lines. A549 (5,000 cells/well) and SF767 (10,000 cells/well) were treated with mafosfamide (corresponding to their approximate ED50 concentration) with increasing concentration (0 µM, 2.5 µM, 5 µM and 10 µM) of analogs CB7, A64 and A70. P values were calculated by comparing the cellular proliferation of DMSO treated cells versus inhibitor treated cells (*, p<0.05, n=15) or mafosfamide (MFM) treated cells versus (MFM+ Inhibitor) treated cells (**, p<0.005, n=15). Black bars represent compound treatment along and grey bars represent compound and mafosfamide treatment. Each bar represents the mean value with standard error.

To confirm targeted binding, we determined the dose-dependency of these three compounds in A549 and SF767 cells (FIG. 13D). We observed a dose-dependent decrease in cell proliferation in both A549 and SF767 cell line. To calculate the shift in $ED_{50}$ value of mafosfamide in the presence of ALDH3A1 inhibitors, we conducted mafosfamide $ED_{50}$ experiment in the presence or absence of CB7, A64 and A70 in SF767 cells. Results showed that in the presence of 10 μM concentration of CB7, A64 and A70, the $ED_{50}$ value of mafosfamide drops from 146±2 μM to 96±6 μM, 75±5 μM, 74±4 μM respectively (FIG. 14). This experiment confirmed that by using ALDH3A1 inhibitors, we can increase mafosfamide chemosensitivity.

Discussion.

Cyclophosphamide is one of the most successful and widely utilized antineoplastic agents. In addition to its antineoplastic property, it is also a potent immunosuppressant and is used during bone marrow transplantation. Varied cellular expression of aldehyde dehydrogenase has an adverse effect in anticancer therapeutics and immunosuppressive properties of cyclophosphamide.

Figure 16:
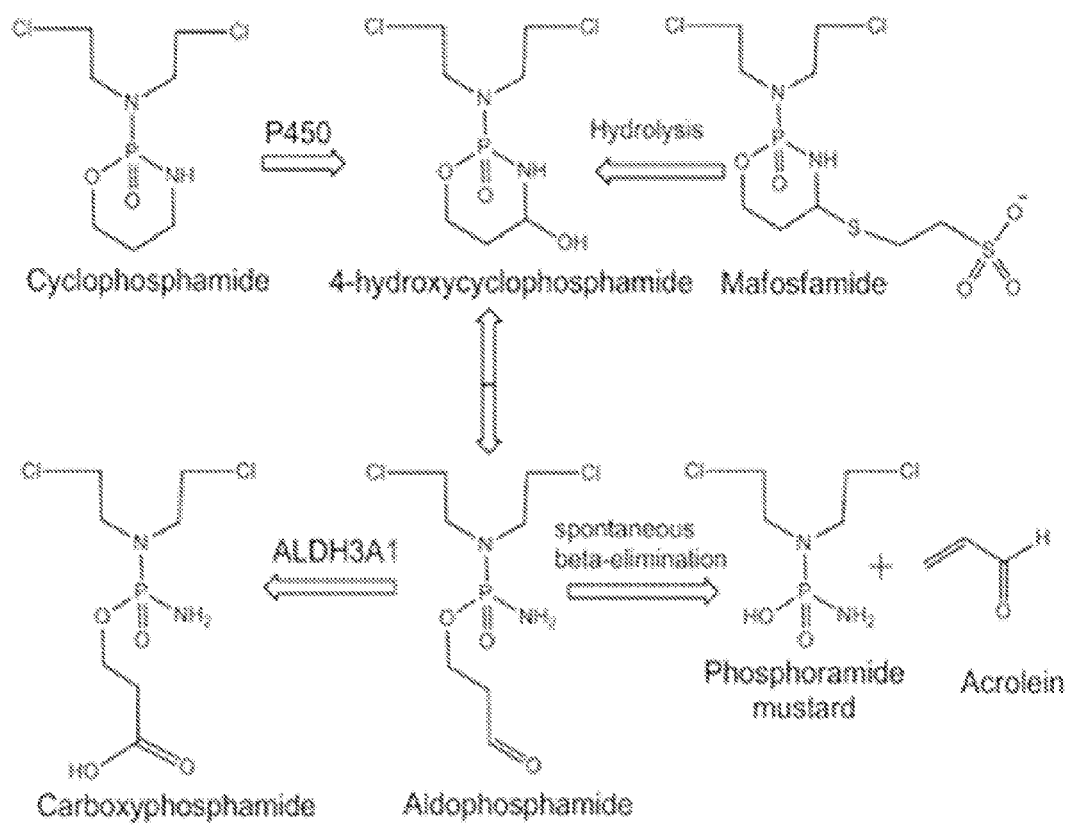
FIG. 16. A schematic overview of cyclophosphamide catabolism.

Cyclophosphamide is activated by cytochrome P450 enzymes to the intermediate 4-hydroxycyclophosphamide (FIG. 16). 4-hydroxycyclophosphamide undergoes spontaneous isomerization to form aldophosphamide. Aldophosphamide can undergo beta-elimination to form acrolein and phosphoramide mustard (FIG. 1), the latter of which forms double-stranded DNA cross-links and stalls replication. Alternatively, aldophosphamide can be metabolized by aldehyde dehydrogenase isozymes to the less toxic carboxyphosphamide metabolite (FIG. 16). As a consequence of their ability to metabolically inactivate aldophosphamide, ALDH isozymes (especially ALDH1A1 and ALDH3A1) are known for their ability to induce resistance toward derivatives of cyclophosphamide[15, 17, 24, 26, 27] To overcome this resistance, increased levels of cyclophosphamide are required, but these higher concentrations lead to severe side effects such as anemia, leukopenia and neutropenia due to bone marrow toxicity[17]. Other effects include cardiac toxicity[40], gonadal failure[41], bladder toxicity[42] and complications such as peripheral neuropathy[43]. Therefore, selective inhibition of the active metabolic pathways present in specific tumors that lead to the inactivation of cyclophosphamide may permit lower effective dosages and potentially reduce the unwanted side effects.

Prior work showed that non-selective inhibition of aldehyde dehydrogenase can sensitize A549 cells to the cytotoxic effects of mafosfamide[31]. Other in vitro and cell-based work demonstrated that both ALDH1A1 and ALDH3A1 contribute to aldophosphamide metabolism, although the contributions of ALDH1A1 is thought to be higher than that of ALDH3A139. This is also consistent with RNAi knockdown studies where reductions in both ALDH1A1 and ALDH3A1 were required for maximal sensitivity to aldophosphamide[15]. Identification of cell permeable selective inhibitors for ALDH3A1 and ALDH1A1 isozymes may therefore help us understand their individual contributions toward aldophosphamide metabolism and could lead to targeted therapies for increasing chemoresistance in selected tumors with specific ALDH isozyme expression.

In our study, we have identified and characterized a very potent and selective inhibitor of ALDH3A1, CB7. Kinetic analysis showed that our inhibitor is competitive with respect to aldehyde substrates and non-competitive with respect to cofactor binding. This is further supported by the crystallographic results that show binding within the aldehyde substrate-binding site. Surprisingly, our SAR studies on analogs of CB7 showed that our original hit compound, CB7, was the most potent analog available. We used the structural information available from CB7•ALDH3A1•NAD+ crystal structure to further illuminate the SAR on this class of compound. The proximity of the benzyl substituent of the benzimidazole moiety to Cys243, Phe401, Leu119 and Tyr115 explains the detrimental effects of adding substituents to the R2 and R3 positions (Table 6 and FIG. 11c).

The nicotinamide carbonyl oxygen is 3.9 Å from the benzimidazole ring such that a methyl group at the R2 position would create steric overlap with this portion of the NAD+ molecule. In addition, the side chain of Tyr65 influences substitutions at the R1 and R4/R8 positions, where larger substituents create a steric clash with Tyr65 (Table 8, FIGS. 11b and 11c). Similarly, the side chain of Tyr115 impacts the available space surrounding the ortho R4/R8 positions. On the other hand, substitutions at the R5 and R6 positions are tolerated because of the small cavity between Trp233 and Tyr65. Our SAR study suggests that smaller substitutions, preferably electron withdrawing halogens, were optimal at the R6 position due to the presence of Trp233 and Met237 at a distances of 4 Å and 3.5 Å from the R6 position, respectively. Overall, our SAR and structural data are fully consistent with CB7 as the most potent compound of the series and that substitutions at various positions were ultimately detrimental to that potency. We also identified Gln122 as a major contributor to the internal topology of ALDH3A1 that accounts for selectivity of CB7 for ALDH3A1 versus ALDH1A1 or ALDH2.

Several compounds reported here enhance the anti-proliferative effects of mafosfamide, but had little if any effects on cellular proliferation themselves. Presumably, this effect is mediated by their ability to inhibit the metabolism of mafosfamide by ALDH3A1. In particular, the SF767 cells used in this work express only ALDH3A1 and demonstrated the greatest level of chemosensitization. However, even the A549 cells, which express both ALDH1A1 and ALDH3A1, could be sensitized by these same compounds. That the action of ALDH3A1 is not the only means by which mafosfamide can be inactivated, is demonstrated by the partial sensitization observed in the A549 cells, relative to the same treatments in SF767 cells. In contrast, these same compounds show neither general toxicity nor enhancement of chemosensitivity in normal lung cells (CCD13Lu), which do not express either ALDH1A1 or ALDH3A1. The high levels of ALDH expression in both SF767 and A549 cells (about 1% of total soluble protein) compared to the undetectable expression in normal lung cells also highlights involvement of these ALDH isoforms as markers of transformed cells.

Figure 14B:
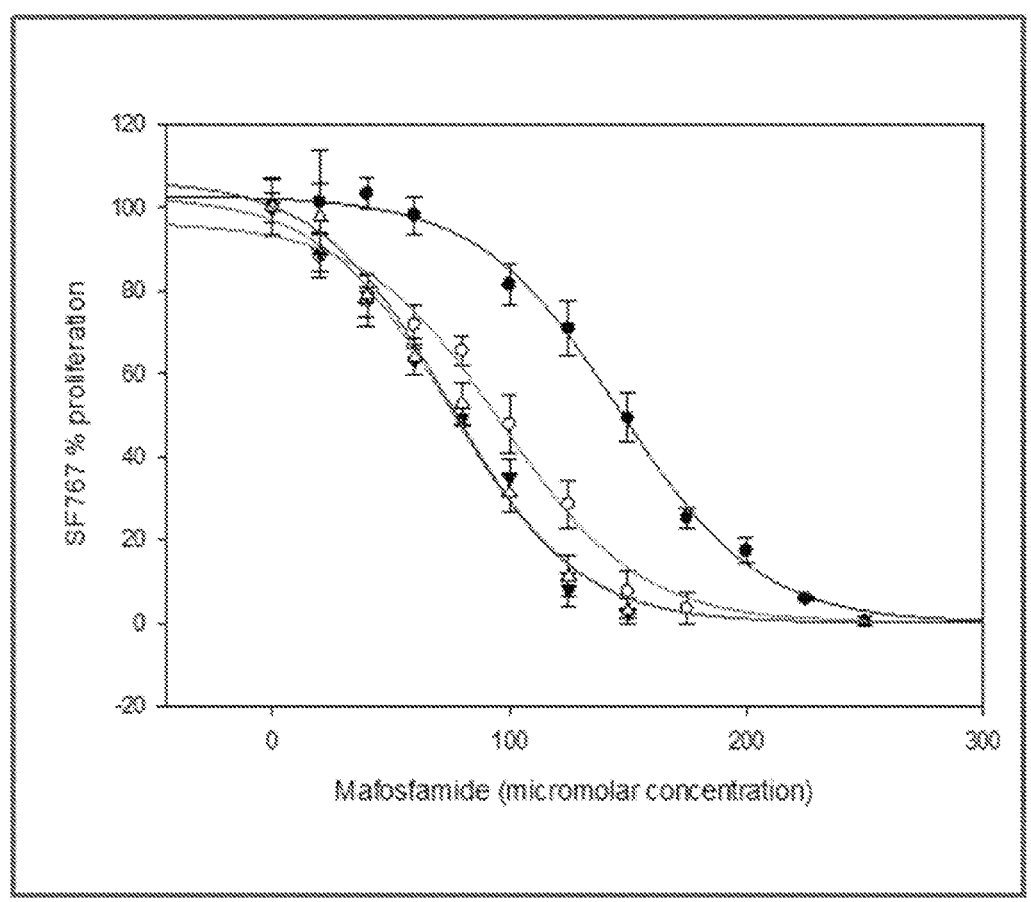
FIG. 14B. Dose-Response Effect of CB7 and CB7 analogs on Proliferation of ALDH3A1-Expressing Cell Lines. SF767 cells (10,000 cells/well) were treated with 10 µM CB7, A64 and A70 with increasing concentration of mafosfamide (0 µM-250 µM). Cell proliferation was determined using MTT assay and plot for percent (%) proliferation was created using the SigmaPlot (v11, StatSys). Shaded circles (●) show SF767 cell proliferation treated with mafosfamide in the absence of inhibitors. Open circles (○), inverted shaded triangles (▼) and open triangles (△) show cell proliferation with mafosfamide in the presence of inhibitors CB7, A64, and A70 respectively. The solid trend lines [MF+DMSO (black), MF+CB7 (pink), MF+A64 (green), MF+A70 (blue)] represent the fits to the 3-parameter logistics equation. DMSO concentration was limited to 0.25% (v/v) (n=15). Figures were generated using SigmaPlot, v 11.0

Whether the general expression of ALDH isozymes is required for the maintenance of the transformed phenotype or is simply a consequence of a change in global gene expression is less clear. However, the involvement of ALDH isoforms in mafosfamide resistance is supported by several lines of evidence[23, 24, 26, 27]. Certainly, the correlation between ALDH expression and sensitivity toward mafosfamide can be seen in the fact that normal lung cells (CCD13Lu) have the lowest ED50 value for mafosfamide at 40 µM, whereas the A549 and SF767 cell lines were considerably more resistant with ED50 values of 125 µM and 146 µM, respectively, for mafosfamide. That ALDH3A1 can be a major contributor to mafosfamide metabolism can be seen in the SF767 glioblastoma cell line. The presence of 10 µM CB7, A64 and A70 lowers the ED50 for mafosfamide to 96±6 µM, 75±5 µM, 74±4 µM respectively (FIG. 14b). In fact, the simultaneous presence of an ALDH3A1 inhibitor and 150 µM mafosfamide reduces cell proliferation to less than 5% of control. Consequently, selective inhibition of ALDH3A1 can provide a means to enhance the anti-proliferative effects of any fixed dose of mafosfamide in selected tumor types and perhaps permit therapies to proceed with reduced marrow toxicity.

TABLE 6

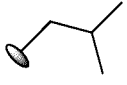

| Cmpd | R1 | R2 | R3 | R4 | R5 | R6 | R7 | R8 | ALDH1A1 | ALDH2 | ALDH3A1 |
|---|---|---|---|---|---|---|---|---|---|---|---|
| A5 | H | H | H | H | H | H | H | H | NI | NI | >50 |
| A3 | H | H | H | H | H | $CH_3$ | H | H | NI | NI | ~50 |
| A16 | H | H | H | H | H | $NHCOCH_3$ | H | H | NI | NI | >100 |
| A67 | H | H | H | H | H | 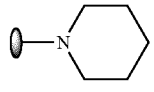 | H | H | NI | NI | >100 |
| A21 | H | H | H | H | H | Cl | H | H | NI | NI | 1.5 (0.5) |
| A24 | H | H | H | H | H | F | H | H | NI(A) | NI | 2.1 (0.4) |
| A10 | $CH_3$ | H | H | H | H | $CH_3$ | H | H | NI | NI | 0.7 (0.2) |
| A20 | $CH_3$ | H | H | H | H | Cl | H | H | NI | NI | 0.3 (0.06) |
| A22 | $CH_3$ | H | H | H | H | $NHCOCH_3$ | H | H | NI | NI | >100 |
| B36 | $NH_2$ | H | H | H | H | Cl | H | H | NI(A) | NI | 1.2 (0.2) |
| B37 | $COCH_3$ | H | H | H | H | Cl | H | H | NI | NI | 1.0 (0.1) |
| A6 | 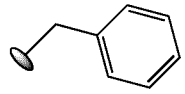 | H | H | H | H | Cl | H | H | NI | NI | >100 |
| A13 | (benzyl) | H | H | H | H | Cl | H | H | NI | NI | >100 |
| A38 | H | $NO_2$ | H | H | H | $OCH_3$ | H | H | NI | NI | >100 |
| A47 | H | $CH_3$ | $CH_3$ | H | H | F | H | H | NI | NI | >100 |
| A39 | H | H | H | OCH3 | H | F | H | H | NI | NI | >100 |
| A30 | $CH_3$ | H | H | H | Br | Cl | H | H | NI | NI | >100 |
| B27 | H | H | H | H | F | F | H | H | NI | NI | 4.2 (1.2) |
| A53 | $CH_3$ | H | H | H | $CH_3$ | Cl | H | H | NI(A) | NI | 0.7 (0.1) |
| A62 | $CH_3$ | H | H | H | $CH_3$ | $OCH_3$ | H | H | NI | NI | 2.0 (0.4) |
| A64 | $CH_3$ | H | H | H | $OCH_3$ | Cl | H | H | NI | NI | 0.9 (0.06) |
| A70 | $CH_3$ | H | H | H | $OCH_3$ | F | H | H | NI | NI | 0.9 (0.2) |
| A40 | $CH_3$ | H | H | H | H | F | H | $OCH_3$ | NI | NI | >100 |
| CB7 | $CH_3$ | H | H | H | H | F | H | H | NI | NI | 0.2 (0.05) |

Table 6 shows an SAR study with analogs of CB7. Values in parentheses represent standard error. NI stands for no inhibition and NI(A) stands for no inhibition but very weak activation (~20% at 100 µM). Residues of ALDH3A1 that are in close contact with CB7 are shown in yellow boxes. None of the compounds tested had any inhibitory effect on ALDH1A2, ALDH1A3 and ALDH1B1. Figure was generated using ChemBioDraw Ultra 12.0.

TABLE 7

X-ray data collection and refinement statistics for ALDH3A1 bound to CB7

| Data collection | ALDH3A1 (CB7 cocrystal) |
|---|---|
| Space group | P21 |
| Cell dimensions | a = 95.2 Å, b = 90.9 Å, and c = 117.9 Å |
| | α = 90°, β = 112.4°, and γ = 90.0° |

TABLE 7-continued

X-ray data collection and refinement statistics for ALDH3A1 bound to CB7

| Data collection | ALDH3A1 (CB7 cocrystal) |
|---|---|
| Resolution (Å) | 108.96 – 1.94 |
| $R_{merge}$ | 0.072 (0.34) |
| $I/\sigma_I$ | 10.9 (4.5) |
| Completeness | 96.3 % |
| Redundancy | 2.8 |
| Refinement | |
| Resolution (Å) | 108.96-1.94 |
| No. of reflections | 125,475 |
| $R_{work}/R_{free}$ | 0.21/0.25 |
| No. of atoms | |
| Protein | 14073 |
| Ligand/Ion | 267 |
| Water | 979 |
| B-factor (overall) | 32.1 |
| RMSD Bond angles (°) | 1.07° |
| RMSD Bond lengths (Å) | 0.005 Å |

TABLE 8

Enzymatic Properties of ALD3H1, and Variants

| | Benzaldehyde $K_m$ (μM) | Benzaldehyde $K_{cat}/K_m$ min$^{-1}$ μM$^{-1}$ | CB7 $K_i$ (μM) | Propionaldehyde $K_m$ (μM) | Propionaldehyde $K_{cat}/K_m$ min$^{-1}$ μM$^{-1}$ |
|---|---|---|---|---|---|
| wt | 279 ± 23 | 4.91 ± 0.25 | 0.2 | 20541 ± 272 | 0.05 ± 0.003 |
| q122a | 425 ± 38 | 3.2 ± 0.13 | 0.2 | 23930 ± 1989 | 0.049 ± 0.003 |
| q122w | 257 ± 35 | 1.73 ± 0.27 | NI (250 μM) | 5357 ± 590 | 0.039 ± 0.005 |

Example 2 References Cited:

(1) Vasiliou, V.; Nerbert, D. W. Analysis and update of the human aldehyde dehydrogenase (ALDH) gene family. *Human Genomics* 2005, 2, 138-143.

(2) Harada, S.; Okubo, T.; Nakamura, T.; Fujii, C.; Nomura, F.; Higuchi, S.; Tsutsumi, M. A novel polymorphism (−357 G/A) of the ALDH2 gene: linkage disequilibrium and an association with alcoholism. *Alcohol Clinical and Experimental Research* 1999, 23, 958-962.

(3) Larson, H. N.; Zhou, J.; Chen, Z.; Stamler, J. S.; Weiner, H.; Hurley, T. D. Structural and functional consequences of coenzyme binding to the inactive asian variant of mitochondrial aldehyde dehydrogenase: roles of residues 475 and 487. *Journal of Biological Chemistry* 2007, 282 (17), 12940-19950.

(4) Chen, Z.; Zhang, J.; Stamler, J. S. Identification of the enzymatic mechanism of nitroglycerin bioactivation. *Proceedings of National Academy of Sciences* 2002, 99, 8306-8311.

(5) Chen, Z.; Foster, M. W.; Zhang, J.; Mao, L.; Rockman, H. A.; Kawamoto, T.; Kitagawa, K.; Nakayama, K. I.; Hess, D. T.; Stamler, J. S. An essential role for mitochondrial aldehyde dehydrogenase in nitroglycerin bioactivation. *Proceedings of National Academy of Sciences* 2005, 102, 12159-12164.

(6) Yao, L.; Fan, P.; Arolfo, M.; Jiang, Z.; Olive, M. F.; Zablocki, J.; Sun, H. L.; Chu, N.; Lee, J.; Kim, H. Y.; Leung, K.; Shryock, J.; Blackburn, B.; Diamond, I. Inhibition of aldehyde dehydrogenase-2 suppresses cocaine seeking by generating THP, a cocaine use-dependent inhibitor of dopamine synthesis. *Nature Medicine* 2010, 16, 1024-1028.

(7) Chen, C. H.; Budas, G. R.; Churchill, E. N.; Disatnik, M. H.; Hurley, T. D.; Rosen, D. M. Activation of aldehyde dehydrogenase-2 reduces ischemic damage to the heart. *Science* 2008, 321, 1493-1495.

(8) Churchill, E. N.; Disatnik, M. H.; Mochly-Rosen, D. Time-dependent and ethanol-induced cardiac protection from ischemia mediated by mitochondrial translocation of varepsilon PKC and activation of aldehyde dehydrogenase 2. *Journal of Molecular and Cellular Cardiology* 2009, 46, 278-284.

(9) Budas, G. R.; Disatnik, M. H.; Chen, C. H.; Mochly-Rosen, D. Activation of aldehyde dehydrogenase 2 (ALDH2) confers cardioprotection in protein kinase C epsilon (PKC varepsilon) knockout mice. *J. of Molecular and Cellular Cardiology* 2010, 48, 757-764.

(10) De, L. V.; Rogers, G. R.; Hamrock, D. J.; Marekov, L. N.; Steinert, P. M.; Compton, J. G.; Markova, N.; Rizzo, W. B. Sjögren-Larsson syndrome is caused by mutations in the fatty aldehyde dehydrogenase gene. *Nature Genetics* 1996, 12, 52-57.

(11) Valle, D.; Goodman, S. I.; Applegarth, D. A.; Shih, V. E.; Phang, J. M. Type II hyperprolinemia. Delta1-pyrroline-5-carboxylic acid dehydrogenase deficiency in cultured skin fibroblasts and circulating lymphocytes. *Journal of Clinical Investigation* 1976, 58, 598-603.

(12) Geraghty, M. T.; Vaughn, D.; Nicholson, A. J.; Lin, W. W.; Jimenez-Sanchez, G.; Obie, C.; Flynn, M. P.; Valle, D.; Hu, C. A. Mutations in the Delta1-pyrroline 5-carboxylate dehydrogenase gene cause type II hyperprolinemia. *Human Molecular Genetics* 1998, 7(9), 1411-1415.

(13) Marcato, P.; Dean, C. A.; Giacomantonio, C. A.; Lee, P. W. Aldehyde dehydrogenase: its role as a cancer stem cell marker comes down to the specific isoform. *Cell Cycle* 2011, 10 (9), 1378-84.

(14) Moreb, J. S. Aldehyde dehydrogenase as a marker for stem cells. *Current Stem Cell Research and Therapy* 2008, 3 (4), 237-246.

(15) Moreb, J. S.; Mohuczy, D.; Ostamark, B.; Zucali, J. R. RNAi-mediated knockdown of aldehyde dehydrogenase class-1A1 and class-3A1 is specific and reveals that each contributes equally to the resistance against 4-hydroperoxycyclophosphamide. *Cancer Chemotherapy and Pharmacology* 2007, 59, 127-136.

(16) Muzio, G.; Maggiora, M.; Paiuzzi, E.; Oraldi, M.; Canuto, R. A. Aldehyde dehydrogenases and cell proliferation. *Free Radical Biology and Medicine* 2012, 52(4), 735-746.

(17) Emadi, A.; Jones, R. J.; Brodsky, R. A. Cyclophosphamide and cancer: golden anniversary. *Nature Reviews in Clinical Oncology* 2009, 6(11), 638-647.

(18) Estey, T.; Cantore, M.; Weston, P. A.; Carpenter, J. F.; Petrash, J. M.; Vasiliou, V. Mechanisms involved in the protection of UV-induced protein inactivation by the corneal crystallin ALDH3A1. *Journal of Biological Chemistry* 2007, 282, 4382-92.

(19) Boesch, J. S.; Lee, C.; Lindahl, R. G. Constitutive expression of class 3 aldehyde dehydrogenase in cultured rat corneal epithelium. *Journal of Biological Chemistry* 1996, 271, 5150-5157.

(20) Abedinia, M.; Pain, T.; Algar, E. M.; Holmes, R. S. Bovine corneal aldehyde dehydrogenase: the major soluble corneal protein with a possible dual protective role for the eye. *Experimental Eye Research* 1990, 51(4), 419-426.

(21) Lassen, N.; Bateman, J. B.; Estey, T.; Kuszak, J. R.; Nees, D. W.; Piatigorsky, J.; Duester, G.; Day, B. J.; Huang, J.; Hines, L. M.; Vasiliou, V. Multiple and additive functions of ALDH3A1 and ALDH1A1: cataract phenotype and ocular oxidative damage in Aldh3a1 (−/−) and Aldh1a1 (−/−) knockout mice. *Journal of Biological Chemistry* 2007, 282(35), 25668-25676.

(22) Sreerama, L.; Rekha, G. K.; Sládek, N. E. Phenolic antioxidant-induced overexpression of class-3 aldehyde dehydrogenase and oxazaphosphorine-specific resistance. *Biochemical Pharmacology* 1995, 49, 669-675.

(23) Sreerama, L.; Sladek, N. E. Cellular levels of class 1 and class 3 aldehyde dehydrogenases and certain other drug-metabolizing enzymes in human breast malignancies. *Clinical Cancer Research* 1997, 3, 1901-1914.

(24) Rekha, G. K.; Sreerama, L.; Sladek, N. E. Intrinsic cellular resistance to oxazaphosphorines exhibited by a human colon carcinoma cell line expressing relatively large amounts of a class-3 aldehyde dehydrogenase. *Biochemical Pharmacology* 1994, 48(10), 1943-52.

(25) Rekha, G. K.; Devaraj, V. R.; Sreerama, L.; Lee, M. J.; Nagasawa, H. T.; Sladek, N. E. Inhibition of human class 3 aldehyde dehydrogenase, and sensitization of tumor cells that express significant amounts of this enzyme to oxazaphosphorines, by chlorpropamide analogues. *Biochemical Pharmacology* 1998, 55(4), 465-474.

(26) Sreerama, L.; Sladek, N. E. Identification and characterization of a novel class 3 aldehyde dehydrogenase overexpressed in a human breast adenocarcinoma cell line exhibiting oxazaphosphorine-specific acquired resistance. *Biochemical Pharmacology* 1993, 45(12), 2487-2505.

(27) Sladek, N. E.; Kollander, R.; Sreerama, L.; Kiang, D. T. Cellular levels of aldehyde dehydrogenases (ALDH1A1 and ALDH3A1) as predictors of therapeutic responses to cyclophosphamide-based chemotherapy of breast cancer: a retrospective study. Rational individualization of oxazaphosphorine-based cancer chemotherapeutic regimens. *Cancer Chemotherapy Pharmacology* 2002, 49, 309-21.

(28) Wang, J. S.; Fang, Q.; Sun, D. J.; Chen, J.; Zhou, X. L.; Lin, G. W.; Lu, H. J.; Fei, J. Genetic modification of hematopoietic progenitor cells for combined resistance to 4-hydroperoxycyclophosphamide, vincristine, and daunorubicin. *Acta Pharmacol. Sinica* 2001, 22, 949-55.

(29) Sreerama, L.; Sladek, N. E. Human breast adenocarcinoma MCF-7/0 cells electroporated with cytosolic class 3 aldehyde dehydrogenases obtained from tumor cells and a normal tissue exhibit differential sensitivity to mafosfamide. *Drug Metabolism and Disposition* 1995, 23(10), 1080-1084

(30) Devaraj, V. R.; Sreerama, L.; Lee, M. J.; Nagasawa, H. T.; Sladek, N. E. Yeast aldehyde dehydrogenase sensitivity to inhibition by chlorpropamide analogues as an indicator of human aldehyde dehydrogenase sensitivity to these agents. *Advances in Experimental Medicine and Biology* 1997, 414, 155-169.

(31) Khanna, M.; Chen, C. H.; Kimble-Hill, A.; Parajuli, B.; Perez-Miller, S.; Baskaran, S.; Kim, J.; Vasiliou, V.; Mochly-Rosen, D.; Hurley, T. D. Discovery of a novel class of covalent inhibitor for aldehyde dehydrogenases. *Journal of Biological Chemistry* 2011, 286 (50), 43486-94.

(32) Hu, G.; Chong, R. A.; Yang, Q.; Wei, Y.; Blanco, M. A.; Li, F.; Reiss, M.; Au, J. L.; Haffty, B. G.; Kang, Y. MTDH activation by 8q22 genomic gain promotes chemoresistance and metastasis of poor-prognosis breast cancer. *Cancer Cell* 2009, 15, 9-20.

(33) Parajuli, B.; Kimble-Hill, A. C.; Khanna, M.; Ivanova, Y.; Meroueh, S.; Hurley, T. D. Discovery of novel regulators of aldehyde dehydrogenase isoenzymes. *Chemico-Biological Interactions* 2011, 191, 153-158.

(34) Liu, Z. J.; Sun, Y. J.; Rose, J.; Chung, Y. J.; Hsiao, C. D.; Chang, W. R.; Kuo, I.; Perozich, J.; Lindahl, R.; Hempel, J.; Wang, B. C. The first structure of an aldehyde dehydrogenase reveals novel interactions between NAD and Rossmann fold. *Nature Structural Biology* 1997, 4(4), 317-26.

(35) Perez-Miller, S.; Hurley, T. D. Coenzyme isomerization is integral to catalysis in aldehyde dehydrogenase. *Biochemistry* 2003, 42, 7100-7109.

(36) Parajuli, B. P.; Georgiadis, T. M.; Fishel, M. L.; Hurley, T. D. Development of Selective Inhibitors for Human Aldehyde Dehydrogenase 3A1 (ALDH3A1) for the Enhancement of Cyclophosphamide Cytotoxicity. 2013, *Submitted to ChemBioChem*

(37) Sladek, N. E. Aldehyde dehydrogenase mediated cellular relative insensitivity to the oxazaphosphorines. *Current Pharm. Design* 1999, 5, 607-625.

(38) Moreb, J. S.; Gabr, A.; Vartikar, G. R.; Gowda, S.; Zucali, J. R.; Mohuczy, D. Retinoic acid down-regulates aldehyde dehydrogenase and increases cytotoxicity of 4-hydroperoxycyclophosphamide and acetaldehyde. *Journal of Pharmacol Exp Therapy* 2005, 312, 339-345.

(39) Giorgianni, F.; Bridson, P. K.; Sorrentino, B. P.; Blakley, R. L. Inactivation of aldophosphamide by human aldehyde dehydrogenase isozyme 3. *Biochemical Pharmacology* 2000, 60(3), 325-38.

(40) Hertenstein, B.; Stefanic, M.; Schemiser, T.; Scholz, M.; Goller, V.; Clausen, M.; Bunjes, D.; Wiesneth, M.; Novotny, J.; Kochs, M. Cardiac toxicity of bone marrow transplantation: predictive value of cardiologic evaluation before transplantation. *Journal of Clinical Oncology* 1994, 12(5), 998-1004.

(41) Boumpas, D. T; Austin, H. A. 3rd.; Vaughan, E. M.; Yarboro, C. H.; Klippel, J. H.; Balow, J. E. Risk for sustained amenorrhea in patients with systemic lupus erythematous receiving intermittent pulse cyclophosphamide therapy. *Annals of Internal Medicine* 1993, 119(5), 366-9.

(42) Stillwell, T. J.; Benson, R. C. Jr.; DeRemee, R. A.; McDonald, T. J.; Weiland, L. H. Cyclophosphamide-induced bladder toxicity in Wegener's granulomatosis. *Arthritis and Rheumatism* 1988, 31(4), 465-70.

(43) Tschöp, K.; Rommel, F.; Schmidkonz, P.; Emmerich, B.; Schulze, J. Neuropathy after cyclophosphamide high dose chemotherapy in a Morbus Werlhof patient. *Deutsche Medizinische Wochenschrift* 2001, 126(12), T17-T20.

(44) Hammen, P. K.; Allali-Hassani, A.; Hallenga, K.; Hurley, T. D.; Weiner, H. Multiple conformations of NAD and NADH when bound to human cytosolic and mitochondrial aldehyde dehydrogenase. *Biochemistry* 2002, 41, 7156-7168.

(45) Weiner, H.; Hu, J. H.; Sanny, C. G. Rate-limiting steps for the esterase and dehydrogenase reaction catalyzed by horse liver aldehyde dehydrogenase. *Journal of Biological Chemistry* 1976, 251 (13), 3853-3855.

(46) Segel, I. H. Simple inhibition systems. *Enzyme Kinetics: Behavior and Analysis of Rapid Equilibrium and Steady-State Enzyme Systems* 1993, John Wiley and Sons, Inc. 100-159.

(47) Minor, W.; Cymborowski, M.; Otwinowski, Z.; Chruszcz, M. HKL-3000: the integration of data reduction and structure solution—from diffraction images to an initial model in minutes. *Acta Crystallogr. D. Biol. Crystallography* 2006, 62, 859-866.

(48) Emsley, P.; Cowtan, K. Coot: model-building tools for molecular graphics. *Acta Crystallogr. D. Biol. Crystallography* 2004, 60, 2126-2132.

(49) Blaney, S. M.; Balis, F. M.; Berg, S.; Arndt, C. A. S.; Heideman, R.; Geyer, J. R.; Packer, R.; Adamson, P. C.; Jaeckle, K.; Klenke, R.; Aikin, A.; Murphy, R.; McCully, C.; Poplack, D. G. Intrathecal Mafosfamide: A Clinical Pharmacology and Phase I trial. *Journal of Clinical Oncology* 2005, 23(7), 1555-1563.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

I claim:

1. A pharmaceutical composition for cancer treatment comprising a pharmaceutically acceptable excipient and a therapeutically effective amount of a compound having a structure selected from the group consisting of:

(a) Formula (I):

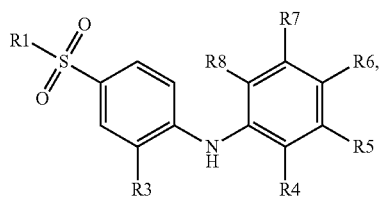

wherein:
R1 is selected from the group consisting of —CH$_3$, —CF$_3$, —NHCH$_3$, and —NHCH(CH$_3$)$_2$;
R3 is selected from the group consisting of —NO$_2$, —F, Cl, —OH, and —OCH$_3$;
R4 is —H;
R5 is selected from the group consisting of —H, —F, and —NH-cyclopropyl;
R6 is selected from the group consisting of —NHCOCH$_3$, —N(CH$_3$)$_2$, —CH$_3$, —OCH$_3$, and —OCHF$_2$;
R7 is —H; and
R8 is —H.

2. The pharmaceutical composition of claim 1, wherein the compound has the structure of Formula (I):

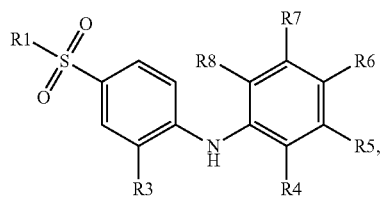

wherein:
R1 is selected from the group consisting of —CH$_3$, —CF$_3$, —NHCH$_3$, and —NHCH(CH$_3$)$_2$;
R3 is selected from the group consisting of —NO$_2$, —F, —Cl, —OH, and —OCH$_3$;
R4 is —H;
R5 is selected from the group consisting of —H, —F, and —NH-cyclopropyl;
R6 is selected from the group consisting of —NHCOCH$_3$, —N(CH$_3$)$_2$, —CH$_3$, —OCH$_3$, and —OCHF$_2$;
R7 is —H; and
R8 is —H.

3. The pharmaceutical composition of claim 2, wherein the compound has the structure of Formula (Ia) (Compound CB29):

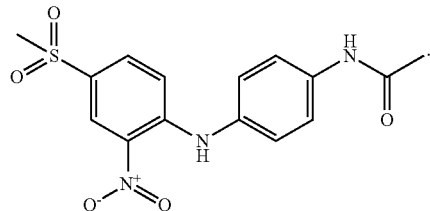 [SMILES: CC(=O)Nc1ccc(Nc2ccc(S(C)(=O)=O)cc2[N+](=O)[O-])cc1]

4. The pharmaceutical composition of claim 1, further comprising one or more chemotherapeutic agents that are substrates for ALDH3A1.

5. The pharmaceutical composition of claim 4, wherein the one or more chemotherapeutic agent comprise paclitaxel, doxorubicin, or 4-hydroxycyclophosphamide.

6. A method for treating cancer comprising administering to a subject in need thereof a pharmaceutical composition comprising a therapeutically effective amount of a compound having a structure selected from the group consisting of:

(a) Formula (I):

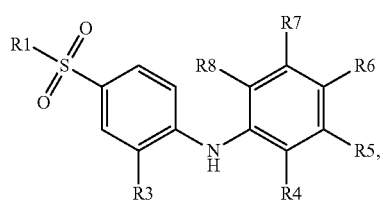

wherein:
R1 is selected from the group consisting of —CH$_3$, —CF$_3$, —NHCH$_3$, and —NHCH(CH$_3$)$_2$;
R3 is selected from the group consisting of —NO$_2$, —F, —Cl, —OH, and —OCH$_3$;
R4 is —H;
R5 is selected from the group consisting of —H, —F, and —NH-cyclopropyl;

R6 is selected from the group consisting of —NHCOCH$_3$, —N(CH$_3$)$_2$, —CH$_3$, —OCH$_3$, and —OCHF$_2$;

R7 is —H; and

R8 is —H;

and wherein the subject is treated with one or more chemotherapeutic agents that are substrates for ALDH3A1.

7. The method of claim 6, wherein the compound has the structure of Formula (I):

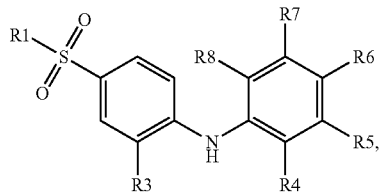

wherein:

R1 is selected from the group consisting of —CH$_3$, —CF$_3$, —NHCH$_3$, and —NHCH(CH$_3$)$_2$;

R3 is selected from the group consisting of —NO$_2$, —F, —Cl, —OH, and —OCH$_3$;

R4 is —H;

R5 is selected from the group consisting of —H, —F, and —NH-cyclopropyl;

R6 is selected from the group consisting of —NHCOCH$_3$, —N(CH$_3$)$_2$, —CH$_3$, —OCH$_3$, and —OCHF$_2$;

R7 is —H; and

R8 is —H.

8. The method of claim 7, wherein the compound has the structure of Formula (Ia) (Compound CB29):

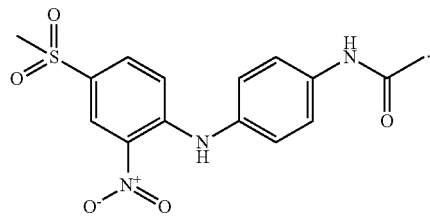

9. The method of claim 6, wherein the one or more chemotherapeutic agents comprise paclitaxel, doxorubicin, or 4-hydroxycyclophosphamide.

10. The method of claim 6, wherein the one or more chemotherapeutic agents are administered to the subject before the administration of the pharmaceutical composition.

11. The method of claim 6, wherein the one or more chemotherapeutic agents are administered to the subject after the administration of the pharmaceutical composition.

12. The method of claim 6, wherein the one or more chemotherapeutic agents are co-administered with the pharmaceutical composition.

13. The method of claim 12, wherein the pharmaceutical composition comprises in combination the therapeutically effective amount of the compound and the one or more chemotherapeutic agents.

14. The method of claim 6, wherein the subject to be treated is suffering from a cancer characterized by overexpression of ALDH3A1.

15. The method of claim 14, wherein the subject is suffering from hepatoma, lung adenocarcinoma, myeloma, breast cancer, colon cancer, or glioblastoma.

16. The method of claim 6, further comprising obtaining from the subject a biological sample comprising cancer cells, and determining an ALDH3A1 mRNA, protein expression, or enzymatic activity level before, during, or after treatment with the pharmaceutical composition.

* * * * *